US008557830B2

(12) United States Patent
Smith et al.

(10) Patent No.: US 8,557,830 B2
(45) Date of Patent: Oct. 15, 2013

(54) RAF KINASE MODULATORS AND METHODS OF USE

(75) Inventors: Adrian L. Smith, Simi Valley, CA (US); Elizabeth M. Doherty, Thousand Oaks, CA (US); Qi Huang, Moorpark, CA (US); Gang Liu, Oak Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 147 days.

(21) Appl. No.: 12/663,504

(22) PCT Filed: Jun. 5, 2008

(86) PCT No.: PCT/US2008/007132
§ 371 (c)(1),
(2), (4) Date: Jul. 28, 2010

(87) PCT Pub. No.: WO2008/153947
PCT Pub. Date: Dec. 18, 2008

(65) Prior Publication Data
US 2010/0324047 A1    Dec. 23, 2010

Related U.S. Application Data

(60) Provisional application No. 60/933,911, filed on Jun. 7, 2007.

(51) Int. Cl.
A01N 43/90    (2006.01)
A61K 31/52    (2006.01)
C07D 473/00   (2006.01)

(52) U.S. Cl.
USPC ..................... 514/263.22; 544/264

(58) Field of Classification Search
None
See application file for complete search history.

(56) References Cited

U.S. PATENT DOCUMENTS

| 6,187,799 B1 | 2/2001 | Wood et al. |
| 7,880,000 B2 | 2/2011 | Geuns-Meyer et al. |
| 7,989,461 B2 | 8/2011 | DeMorin et al. |
| 2001/0006975 A1 | 7/2001 | Wood et al. |

FOREIGN PATENT DOCUMENTS

| WO | 99/32106 A1 | 7/1999 |
| WO | 00/42012 A3 | 7/2000 |
| WO | 01/38324 A3 | 5/2001 |
| WO | 03/047523 A2 | 6/2003 |
| WO | 2004/005281 A1 | 1/2004 |
| WO | 2005/033086 A1 | 4/2005 |

Primary Examiner — Jeffrey Murray
(74) Attorney, Agent, or Firm — G. Prabhakar Reddy

(57) ABSTRACT

The present invention comprises a new class of compounds capable of modulating the activity of Raf kinase and, accordingly, useful for treatment of Raf kinase mediated diseases, including melanomas, tumors and other cancer-related conditions. The compounds have a general Formula (I) wherein each of $A^1, A^2, A^3, A^4, A^5, A^6, A^7, A^8, A^9$, bond B, X, rings $Z^1$ and $Z^2$, $R^1$ and $R^3$ are defined herein. The invention further comprises pharmaceutical compositions, methods for treatment of Raf kinase mediated diseases, and intermediates and processes useful for the preparation of compounds of the invention.

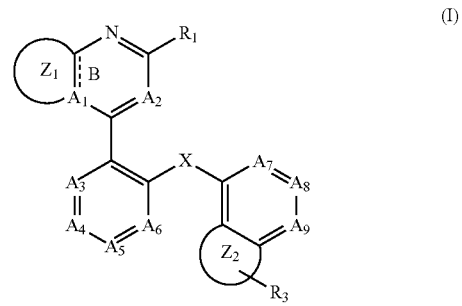

13 Claims, No Drawings

RAF KINASE MODULATORS AND METHODS OF USE

This application is a US national stage application via 35 USC §371(c) of PCT/US2008/007132, filed on May 6, 2008, which PCT application claims the benefit of U.S. Provisional Application No. 60/933,911, filed Jun. 7, 2007, both specifications of which are hereby incorporated herein by reference in their entireties.

FIELD OF THE INVENTION

The invention generally relates to the field of pharmaceutical agents and, specifically to novel compounds, intermediates and pharmaceutical compositions capable of modulating Raf protein kinase(s) activity and useful for cancer.

BACKGROUND OF THE INVENTION

Cancer is one of the most widespread diseases of mankind and a major cause of death worldwide. In an effort to find an effective treatment or a cure for one or more of the many different forms of cancers and cancerous disease, over the last couple of decades, numerous research groups have invested a tremendous amount of time, effort and financial resources. However, to date, of the available cancer treatments and therapies, only a few offer any considerable degree of success.

Cancer is caused in many cases by the effects of oncoproteins. These are proteins having different structures as compared to their counterpart proteins in normal, healthy organisms. These oncoproteins are capable of transforming a normal cell into an uncontrollable, proliferating cell i.e., a cancerous cell, leading to the formation and growth of cancerous tumors. Oncoproteins are formed and expressed in an organism as a product of onco-genes, whose nucleotides sequence encodes the oncoprotein. Oncogenes occur as a result of a mutation of a "normal", healthy gene, typically referred to as the "proto-oncogene." Such mutations in proto-oncogenes produce protein products, which alter the normal programs of cell proliferation, differentiation and death. In a human cancer cell, one cell-signaling pathway in in which a proto-oncogene is mutated is the RAS-RAF-MEK-ERK-MAP kinase-signaling pathway. This pathway has been found to mediate cellular responses to growth signals. (Peyssonnaux et al., Biol. Cell, 93:53-62 (2001)).

The cell-signaling pathway involves the binding of a RAS substrate to activate a Raf kinase enzyme, which in turn activates the MEK kinase and so forth. There are three cytoplasmic serine/threonine RAF kinase proteins, which are polypeptides encoded by the nucleotide sequence of three Raf genes. The three Raf proteins found in mammals are A-raf, B-raf and C-raf (C-raf is also known as Raf-1). (Biol. Cell, 93:53-62 (2001)). One feature in common among the three proteins is that they all share highly conserved regions, called CR1, CR2 and CR3. The CR1 domain is rich in cysteine residues, while the CR2 region contains many serines and threonine residues. The CR3 domain contains the kinase activity. The three naturally occurring Raf proteins also feature size differences. On average, B-raf proteins are larger than the other two, having a molecular weight of about 90 kDa, while the A-raf and C-raf have an average molecular weight of about 70 kDa. All three RAF proteins function by phosphorylating MEK-1/2, which in turn phosphorylates Erk-1/2, thereby activating the MEK-ERK MAP kinase portion of the signaling pathway described above. Structure, activity and function of the members of the Raf kinase family are further described in detail in Morrison and Cutler, Current Opinion in Cell Biology, 9:174-179 (1997) and U.S. Pat. Nos. 5,618,670, 5,156,841, and 6,566,581.

The B-raf protein has been found to be more capable of phosphorylating the MEK-I and MEK-2 proteins than either of the A-raf and C-raf proteins. The B-raf phosphorylating activity is about 500× stronger than that of A-raf and about 10× stronger than that of C-raf. (Mol. Cell. Biol., 15 (1997)). Accordingly, B-raf has become a potential target for regulating the RAS-RAF-MEK-ERK-MAP signaling pathway and, in turn, regulating programmed cell proliferation, cell differentiation and cell death.

B-raf kinase is commonly activated by somatic point mutations in cancerous cells. For example, B-raf somatic missense mutations occur in about 66% of malignant melanomas and at lower frequency in a wide range of human cancers. B-raf mutations have been found in 28 primary cancers/STC's, including 6 of 9 primary melanomas, 12 of 15 melanoma STC's, 4 of 33 colorectal carcinomas, 5 or 35 ovarian neoplasms, and 1 of 182 sarcomas. Although B-raf mutations occur in a wide range of cancers, there is a trend towards the occurance of mutations in cancer types in which a substantial portion of cases are known to harbor RAS mutations (for example, malignant melanomas, colorectal cancer, and borderline ovarian cancers). Mutated B-raf proteins have elevated kinase activity and are transforming in NIH3T3 cells. All mutations of B-raf have been found to be within the kinase domain, with a single substitution (V600E) accounting for about 80% of the mutated B-raf proteins discovered to date. It is worth noting that Ras function is not required for the growth of cancer cell lines with the V599E mutation. The high frequency of B-raf mutations in melanomas and the relative lack of effective therapies for advanced stages of this disease suggest that inhibition of wild-type B-raf and/or mutated B-raf activity may provide new therapeutic opportunities for metastatic and/or malignant melanomas.

Various groups have proposed different classes of compounds to generally modulate, or specifically inhibit, Raf kinase activity, for use to treat Raf-mediated disorders. For example, the PCT publication, WO 99/32106, describes substituted heterocyclic ureas for the inhibition of Raf kinase, WO 03/047523, describes methods for treating cancers resulting from the up-regulation of the RAF-MEK-ERK pathway using Gleevec® and "Gleevec®-like" compounds, WO 00/42012, describes delta-carboxyaryl substituted diphenyl ureas as Raf kinase inhibitors, WO 01/38324, describes substituted heteroaryl compounds for the inhibition of B-Raf kinase, U.S. Publication No. 2001/006975, describes methods of treating tumors mediated by raf kinase using substituted urea compounds, and U.S. Pat. No. 6,187,799, describes methods of treating tumors mediated by raf kinase using aryl urea compounds.

BRIEF DESCRIPTION OF THE INVENTION

The present invention provides a novel class of nitrogen-containing bicyclic heteroaryl compounds useful for modulating the activity of Raf kinase proteins and, thereby, useful for treating Raf kinase-mediated diseases and conditions. Particularly, the compounds are useful for treating tumors, melanomas and other forms of cancer. The compounds provided by the invention, including stereoisomers, tautomers, solvates, pharmaceutically acceptable salts, derivatives or prodrugs thereof, are defined by general Formula I

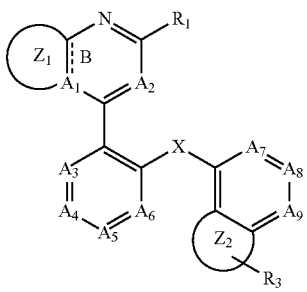

wherein each of $A^1, A^2, A^3, A^4, A^5, A^6, A^7, A^8, A^9$, bond B, X, rings $Z^1$ and $Z^2$, $R^1$ and $R^3$ are as described below.

In another embodiment, the invention provides compounds defined generally by Formula II

II wherein $Z^1, Z^2, A^3, A^4, X, R^1, R^2, R^5$ and $R^6$ are as defined and described below.

The invention also provides procedures for making compounds of Formulas I-II, as well as intermediates useful in such procedures.

The compounds provided by the invention are capable of modulating Raf kinase activity, and more particularly of modulating B-raf kinase activity. To this end, the invention further provides for the use of these compounds for therapeutic, prophylactic, acute and/or chronic treatment of Raf kinase-mediated diseases, such as those described herein. For example, the invention provides the use and preparation of a medicament, containing one or more of the compounds, useful to attenuate, alleviate, or treat disorders through inhibition of B-raf. These compounds are also useful in the treatment of a cancerous disease or condition. Accordingly, these compounds are useful in the manufacture of anti-cancer medicaments. In one embodiment, the invention provides a pharmaceutical composition comprising an effective dosage amount of a compound of any of Formulas I-II in association with a least one pharmaceutically acceptable carrier, adjuvant or diluent.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

The invention provides novel nitrogen-containing fused heterocyclic compounds, which are useful for treating cell proliferation-related disorders, including cancer. In one embodiment of the invention, the compounds, including stereoisomers, tautomers, solvates, pharmaceutically acceptable salts, derivatives or prodrugs thereof, are defined by general Formula I:

I wherein $A^1$ is C, $CR^2$ or N, provided that when $A^1$ is $CR^2$ or N, then the bond B is a single bond, and when $A^1$ is C then bond B is a double bond;

each of $A^2, A^3, A^4, A^5, A^6, A^7, A^8$ and $A^9$, independently, is $CR^2$ or N, provided that (1) no more than two of $A^3, A^4, A^5$ and $A^6$ is N, and (2) no more than two of $A^7, A^8$ and $A^9$ is N;

X is $CR^2R^2$, C(O), $NR^2$, O or $S(O)_p$ wherein p is 0, 1, or 2;

$Z^1$, together with the carbon atoms or carbon and nitrogen atoms to which it is attached, is a fully saturated or partially or fully unsaturated 5- or 6-membered ring of carbon atoms optionally including 1-3 heteroatoms selected from O, N, or S, and optionally substituted independently with 1-5 substituents of $R^4$;

$Z^2$ is

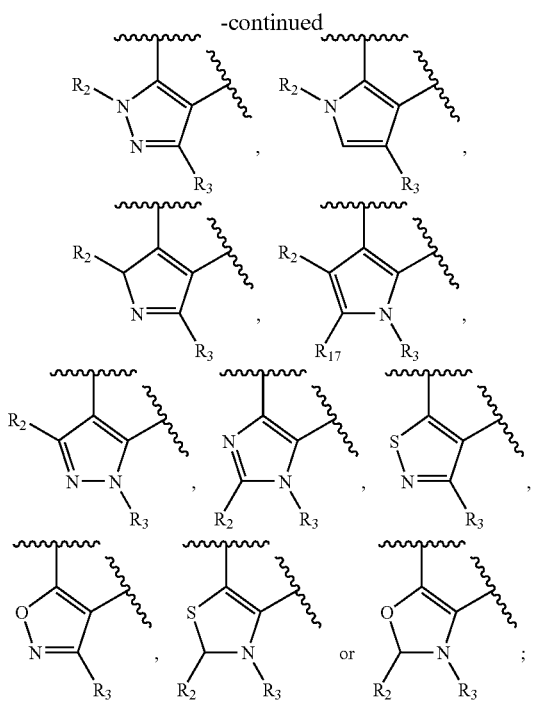

R[1] is H, halo, haloalkyl, NO$_2$, CN, OR[7], SR[7], NR[7]R[7], NR[7]R[8], C(O)R[7], C$_{1-6}$-alkyl, C$_{2-6}$-alkenyl, C$_{2-6}$-alkynyl or C$_{3-6}$-cycloalkyl;

each R[2] independently, is H, halo, haloalkyl, NO$_2$, CN, C$_{1-6}$-alkyl, C$_{2-6}$-alkenyl, C$_{2-6}$-alkynyl, C$_{3-6}$-cycloalkyl, NR[7]R[7], NR[7]R[8], OR[7], SR[7], C(O)R[7], OC(O)NR[7]R[7], COOR[7], C(O)NR[7]R[7], C(S)NR[7]R[7], NR[7]C(O)R[7], NR[7]C(O)NR[7]R[7], NR[7](COOR[7]), OC(O)NR[7]R[7], S(O)$_2$R[7], S(O)$_2$NR[7]R[7], NR[7]S(O)$_2$NR[7]R[7] or NR[7]S(O)$_2$R[7];

R[3] is NR[5]R[5], NR[5]R[6], OR[5], SR[5], OR[6], SR[6], C(O)R[5], C(S)R[5], C(NCN)R[5], C(O)R[6], C(S)R[6], C(NCN)R[6], OC(O)R[5], COOR[5], C(O)NR[5]R[5], C(O)NR[5]R[6], NR[5]C(O)R[5], NR[5]C(O)R[6], NR[5]C(O)NR[5]R[5], NR[5]C(O)NR[5]R[6], NR[5](COOR[5]), NR[5](COOR[6]), S(O)$_2$R[5], S(O)$_2$R[6], S(O)$_2$NR[5]R[5], S(O)$_2$NR[5]R[6], NR[5]S(O)$_2$NR[5]R[6], NR[5]S(O)$_2$R[5] or NR[5]S(O)$_2$R[6];

each R[4], independently, is H, halo, haloalkyl, oxo, OH, NO$_2$, NH$_2$, C$_{1-8}$-alkyl, —O—C$_{1-8}$-alkyl, —S—C$_{1-8}$-alkyl, —NH—C$_{1-8}$-alkyl, —N-di-C$_{1-8}$-alkyl, —C$_{1-6}$-alkyl-NH—C$_{1-6}$-alkyl, C$_{2-8}$-alkenyl, C$_{2-8}$-alkynyl, C$_{3-6}$-cycloalkyl, or a partially or fully saturated or unsaturated 5-8 membered monocyclic ring formed of carbon atoms optionally including 1-3 heteroatoms, wherein each of said C$_{1-8}$-alkyl, C$_{1-8}$-alkenyl, C$_{1-8}$-alkynyl and ring is optionally substituted independently with 1-5 substituents of R[7];

each R[5] independently, is H, C$_{1-8}$-alkyl, C$_{2-8}$-alkenyl, C$_{2-8}$-alkynyl, C$_{3-6}$-cycloalkyl or C$_{4-8}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of R[6] or R[7], NR[6]R[7], NR[7]R[7], OR[6], SR[6], OR[7], SR[7], C(O)R[7], OC(O)R[6], COOR[6], C(O)R[7], OC(O)R[7], COOR[7], C(O)NR[6]R[7], NR[7]C(O)R[6], C(O)NR[7]R[7], NR[7]C(O)R[7], NR[7]C(O)NR[6]R[7], NR[7]C(O)NR[7]R[7], NR[7](COOR[6]), NR[7](COOR[7]), OC(O)NR[6]R[7], OC(O)NR[7]R[7], S(O)$_2$R[6], S(O)$_2$R[7], S(O)$_2$NR[6]R[7], S(O)$_2$NR[7]R[7], NR[7]S(O)$_2$NR[6]R[7], NR[7]S(O)$_2$NR[7]R[7], NR[7]S(O)$_2$R[6], NR[7]S(O)$_2$R[7], NR[7]S(O)$_2$R[6] or NR[7]S(O)$_2$R[7];

R[6] is a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of R[7];

alternatively, R[5] and R[6] taken together form a partially or fully saturated or unsaturated 5-6 membered ring of carbon atoms optionally including 1-3 heteroatoms selected from O, N, or S, and the ring optionally substituted independently with 1-5 substituents of R[7]; and each R[7], independently, is H, F, Cl, Br, I, haloalkyl, CN, OH, NO$_2$, NH$_2$, C$_{1-8}$-alkyl, —O—C$_{1-8}$-alkyl, —C$_{1-6}$-alkyl-O—C$_{1-6}$-alkyl, —S—C$_{1-8}$-alkyl, —C$_{1-6}$-alkyl-S—C$_{1-6}$-alkyl, —NH—C$_{1-8}$-alkyl, —N-di-C$_{1-8}$-alkyl, —C$_{1-6}$-alkyl-NH—C$_{1-6}$alkyl, C$_{2-8}$-alkenyl, C$_{2-8}$-alkynyl, C$_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said C$_{1-8}$-alkyl, C$_{1-8}$-alkenyl, C$_{1-8}$-alkynyl and ring of said ring system is optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided the compound is not N5-(3-(7H-pyrrolo[2,3-d]pyrimidin-4-yl)pyridin-2-yl)-6-methyl-N1-(2-methyl-5-(trifluoromethyl)phenyl)isoquinoline-1,5-diamine and 4-(5-(3-(7H-pyrrolo[2,3-d]pyrimidin-4-yl)pyridin-2-ylamino)-6-methylisoquinolin-1-ylamino)benzonitrile.

In another embodiment, the compounds of Formula I include compounds wherein Z[1] is a ring selected from

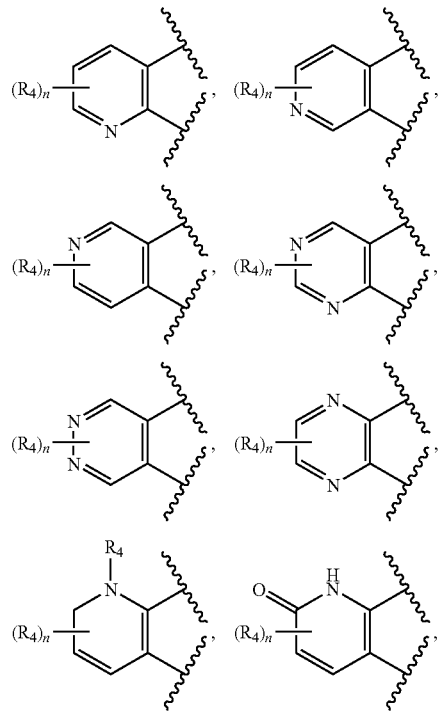

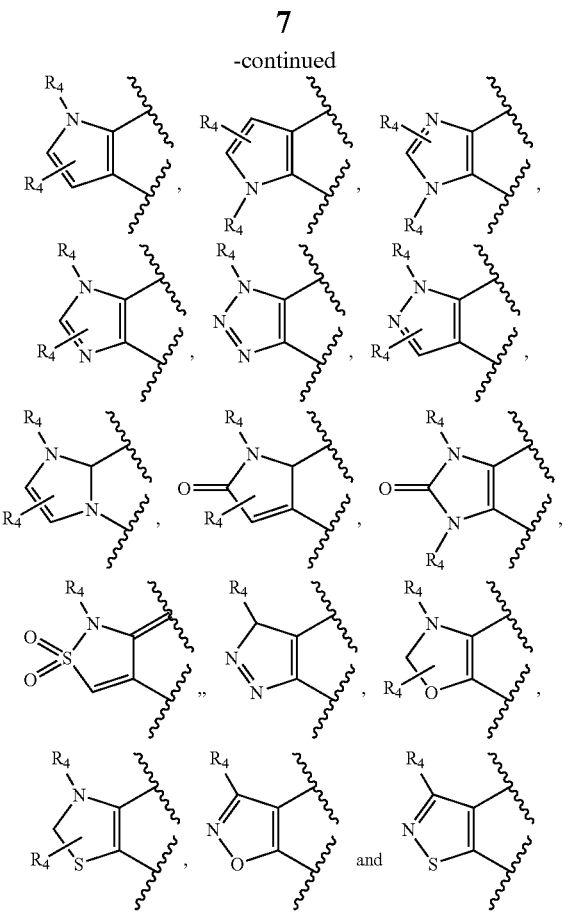

wherein $R^4$ is as defined in claim 1 and n is 1, 2 or 3, in conjunction with any of the above or below embodiments.

In another embodiment, the compounds of Formula I include compounds wherein $Z^1$ is a phenyl, pyridyl, pyrimidinyl, triazinyl, pyridazinyl, thiophenyl, furyl, pyrrolyl, pyrazolyl, triazolyl, thiazolyl, thiadiazolyl, oxazolyl, oxadiazolyl, isoxazolyl or isothiazolyl ring, in conjunction with any of the above or below embodiments.

In another embodiment, the compounds of Formula I include compounds wherein $Z^1$ is a phenyl, pyridyl, pyrrolyl, imidazolyl), triazolyl or tetrazolyl ring, in conjunction with any of the above or below embodiments.

In another embodiment, the compounds of Formula I include compounds wherein $A^1$ is C, $A^2$ is N and bond B is a double bond, in conjunction with any of the above or below embodiments.

In another embodiment, the compounds of Formula I include compounds wherein each of $A^3$, $A^4$ and $A^5$, independently, is CH and $A^6$ is N, in conjunction with any of the above or below embodiments.

In another embodiment, the compounds of Formula I include compounds wherein each of $A^7$, $A^8$ and $A^9$, independently, is $CR^2$ wherein each $R^2$, independently, is H, halo, haloalkyl, $NO_2$, CN, $C_{1-6}$-alkyl, $C_{2-6}$-alkenyl, $C_{2-6}$-alkynyl, $C_{3-6}$-cycloalkyl, $NR^7R^7$, $OR^7$, $SR^7$ or $C(O)R^7$ and $R^7$ is H, —$C_{1-6}$-alkyl or $C_{1-6}$-haloalkyl, in conjunction with any of the above or below embodiments.

In another embodiment, the compounds or a stereoisomer, tautomer or pharmaceutically acceptable salt thereof, are defined by a general Formula II

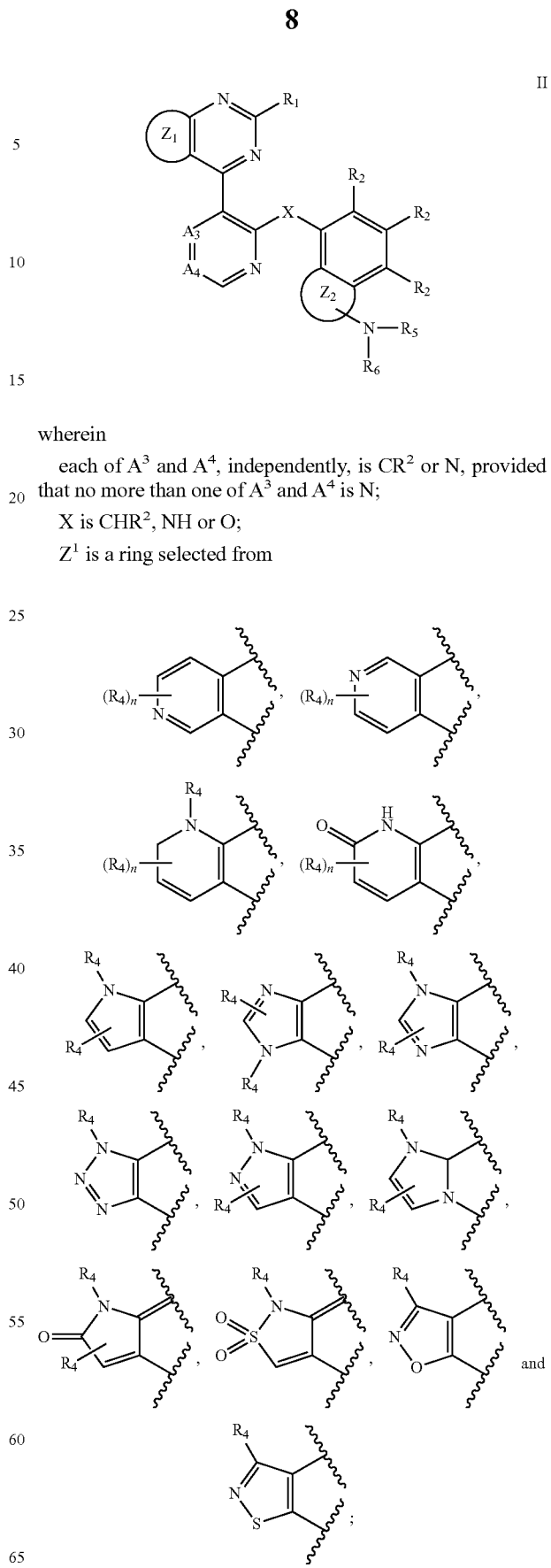

wherein each of $A^3$ and $A^4$, independently, is $CR^2$ or N, provided that no more than one of $A^3$ and $A^4$ is N;

X is $CHR^2$, NH or O;

$Z^1$ is a ring selected from $Z^2$ is a ring selected from

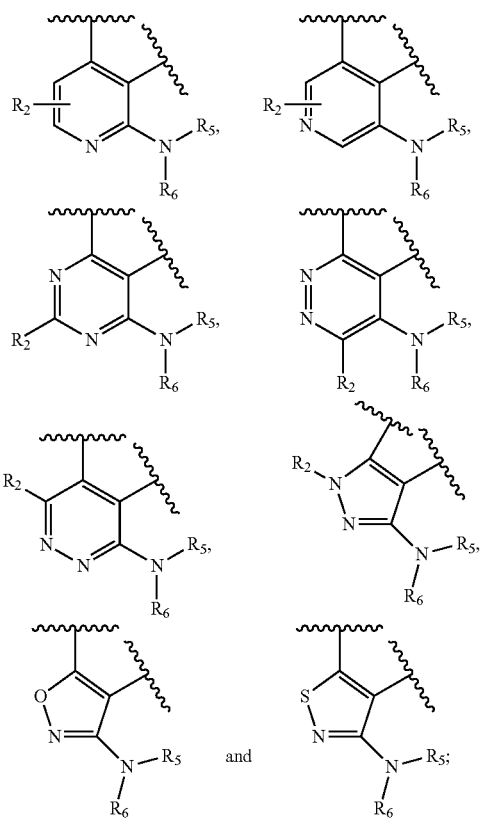

$R^1$ is H, halo, haloalkyl, CN, $OR^7$, $SR^7$, $NR^7R^7$, $C(O)R^7$ or $C_{1-6}$-alkyl;

each $R^2$ independently, is H, halo, haloalkyl, CN, $OR^7$, $SR^7$, $NR^7R^7$, $C(O)R^7$ or $C_{1-6}$-alkyl;

each $R^4$, independently, is H, halo, haloalkyl, CN, $OR^7$, $SR^7$, $NR^7R^7$, $C(O)R^7$ or $C_{1-6}$-alkyl;

$R^5$ is H, $C_{1-6}$-alkyl or $C_{3-6}$-cycloalkyl optionally substituted with 1-3 substituents of $R^7$;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and each $R^7$, independently, is H, F, Cl, Br, I, haloalkyl, CN, OH, $NO_2$, $NH_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided the compound is not N5-(3-(7H-pyrrolo[2,3-d]pyrimidin-4-yl)pyridin-2-yl)-6-methyl-N1-(2-methyl-5-(trifluoromethyl)phenyl)isoquinoline-1,5-diamine and 4-(5-(3-(7H-pyrrolo[2,3-d]pyrimidin-4-yl)pyridin-2-ylamino)-6-methylisoquinolin-1-ylamino)benzonitrile.

In another embodiment the compounds of Formulas I or II include compounds wherein $Z^1$ is a ring selected from

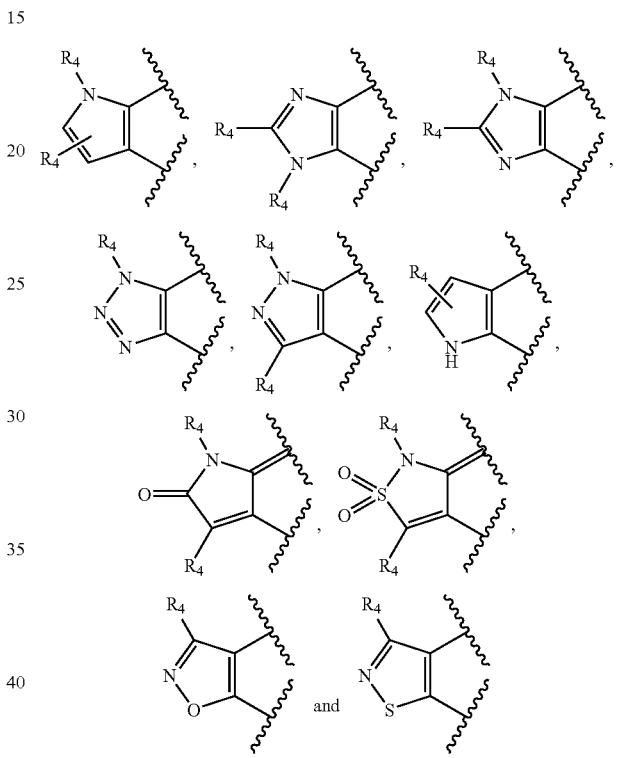

wherein $R^4$ is as defined hereinbove, in conjunction with any of the above or below embodiments.

In another embodiment, the compounds of Formulas I or II include compounds wherein $Z^1$ is a ring selected from

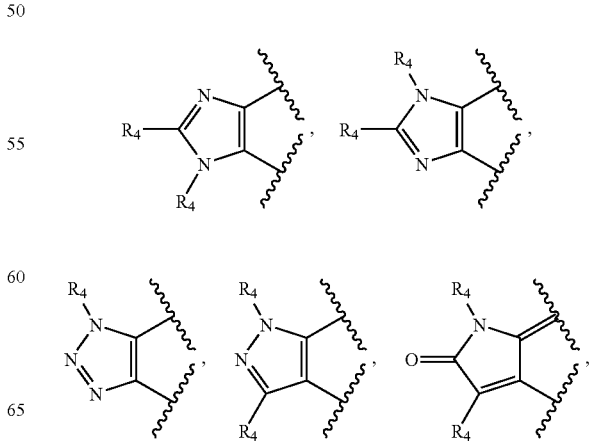

-continued

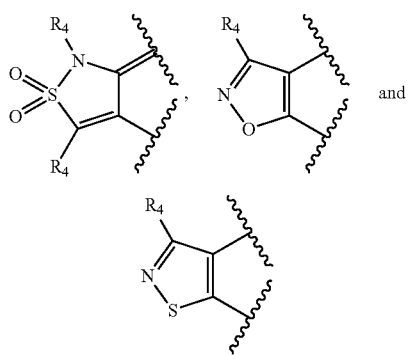

wherein R⁴ is as defined hereinbove, in conjunction with any of the above or below embodiments.

In another embodiment, the compounds of Formulas I or II include compounds wherein $Z^1$ is a ring selected from

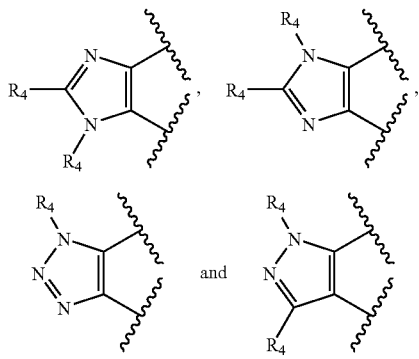

wherein R⁴ is as defined hereinbove, in conjunction with any of the above or below embodiments.

In another embodiment, the compounds of Formula I or II include compounds wherein $Z^2$ is

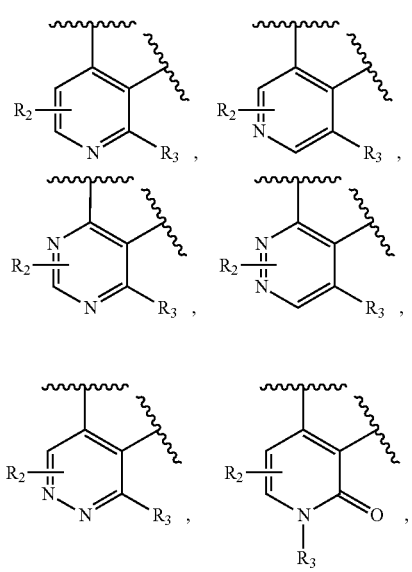

-continued

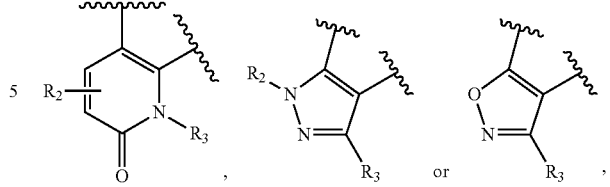

in conjunction with any of the above or below embodiments.

In another embodiment, the compounds of Formula I or II include compounds wherein $Z^2$ is

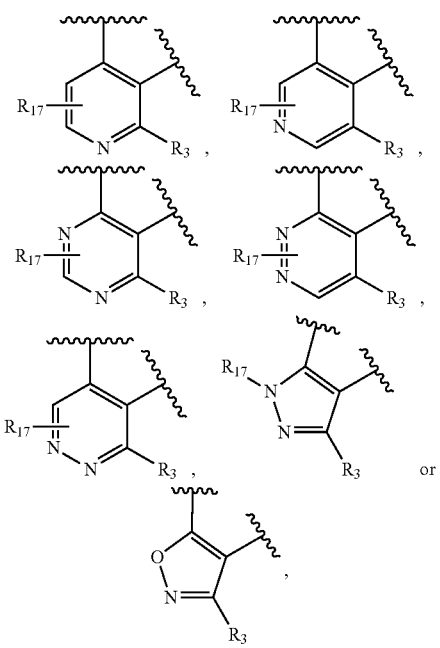

in conjunction with any of the above or below embodiments.

In another embodiment, the compounds of Formula I or II include compounds wherein X is CH₂, NH, O or S, in conjunction with any of the above or below embodiments.

In another embodiment, the compounds of Formula I or II include compounds wherein $R^3$ is $NR^5R^5$, $NR^5R^6$, $NR^5C(O)R^5$, $NR^5C(O)R^6$, $NR^5S(O)_2R^6$ or $NR^5S(O)_2R^6$;

$R^5$ is H, $C_{1-6}$-alkyl or $C_{3-6}$-cycloalkyl optionally substituted with 1-3 substituents of $R^7$; and $R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$, in conjunction with any of the above or below embodiments.

In another embodiment, the compounds of Formula I or II include compounds wherein each $R^2$, independently, is H, halo, haloalkyl or $C_{1-6}$-alkyl; and each $R^4$, independently, is H, halo, haloalkyl or $C_{1-6}$-alkyl, in conjunction with any of the above or below embodiments.

In another embodiment, the compounds of Formula I or II include compounds wherein each of $A^3$ and $A^4$ is $CR^2$, in conjunction with any of the above or below embodiments.

In another embodiment, the compounds of Formula II include compounds wherein at least one of the three $R^2$ substitutions is other than H, in conjunction with any of the above or below embodiments.

In another embodiment, the compounds of Formula I or II include compounds wherein $R^4$ is H, halo, haloalkyl, $NO_2$, CN, $C_{1-10}$-alkyl, $NR^7R^7$, $NR^7R^8$, $OR^7$, $SR^7$, $OR^8$, $SR^8$, $C(O)R^7$ or $C(O)R^8$, in conjunction with any of the above or below embodiments.

In another embodiment, the compounds of Formula I or II include compounds wherein each of $R^5$ and $R^6$, respectively, is H, halo, haloalkyl, $NO_2$, CN, —$OC_{1-10}$-alkyl, —$SC_{1-10}$-alkyl, $NH_2$, —$NHC_{1-10}$-alkyl, —$NHC_{3-7}$-cycloalkyl, —$C(O)C_{1-10}$-alkyl or —$S(O)_2C_{1-10}$-alkyl as, independently, in conjunction with any of the above or below embodiments.

In another embodiment, the compounds or a stereoisomer, tautomer or pharmaceutically acceptable salt thereof, are defined by a general Formula II

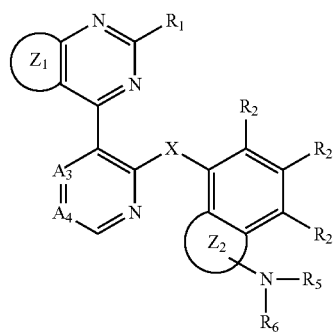

wherein each of $A^3$ and $A^4$, independently, is $CR^2$ or N, provided that no more than one of $A^3$ and $A^4$ is N;

X is $CHR^2$, NH or O;

$Z^1$ is a ring selected from

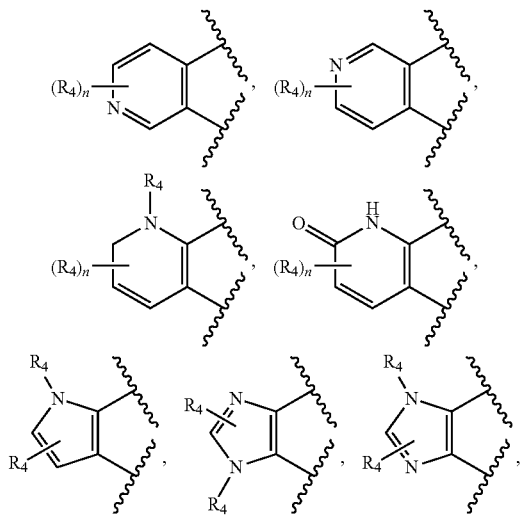

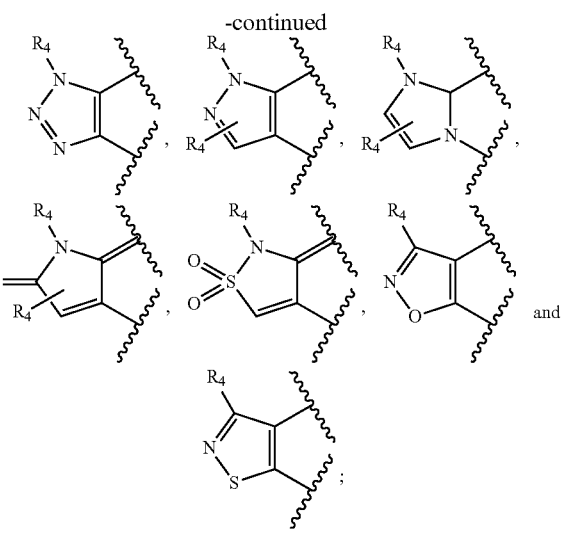

$Z^2$ is a ring selected from

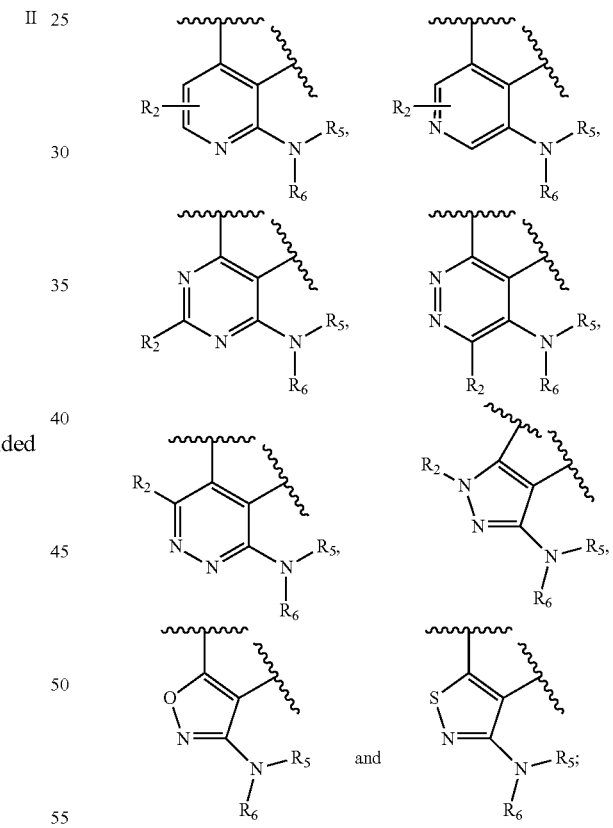

$R^1$ is H, halo, haloalkyl, CN, $OR^7$, $SR^7$, $NR^7R^7$, $C(O)R^7$ or $C_{1-6}$-alkyl;

each $R^2$ independently, is H, halo, haloalkyl, CN, $OR^7$, $SR^7$, $NR^7R^7$, $C(O)R^7$ or $C_{1-6}$-alkyl;

each $R^4$, independently, is H, halo, haloalkyl, CN, $OR^7$, $SR^7$, $NR^7R^7$, $C(O)R^7$ or $C_{1-6}$-alkyl;

$R^5$ is H, $C_{1-6}$-alkyl or $C_{3-6}$-cycloalkyl optionally substituted with 1-3 substituents of $R^7$;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and each $R^7$, independently, is H, F, Cl, Br, I, haloalkyl, CN, OH, $NO_2$, $NH_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided the compound is not N5-(3-(7H-pyrrolo[2,3-d]pyrimidin-4-yl)pyridin-2-yl)-6-methyl-N1-(2-methyl-5-(trifluoromethyl)phenyl)isoquinoline-1,5-diamine and 4-(5-(3-(7H-pyrrolo[2,3-d]pyrimidin-4-yl)pyridin-2-ylamino)-6-methylisoquinolin-1-ylamino)benzonitrile.

In another embodiment, the compounds or a stereoisomer, tautomer or pharmaceutically acceptable salt thereof, are defined by a general Formula II-A

II-A

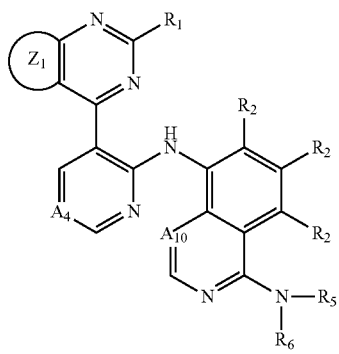

wherein $A^4$ is $CR^2$ or N;

$A^{16}$ is CH or N;

$Z^1$ is a ring selected from

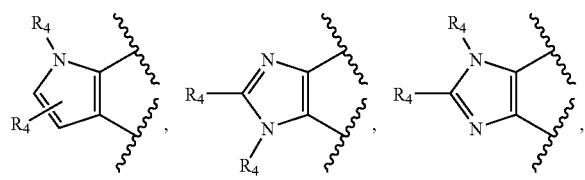

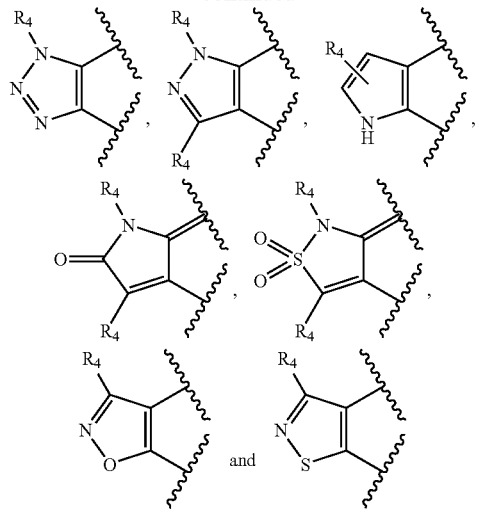

$R^1$ is H, halo, haloalkyl, CN, $OR^7$, $SR^7$, $NR^7R^7$, $C(O)R^7$ or $C_{1-6}$-alkyl;

each $R^2$ independently, is H, halo, haloalkyl, CN, $OR^7$, $SR^7$, $NR^7R^7$, $C(O)R^7$ or $C_{1-6}$-alkyl;

each $R^4$, independently, is H, halo, haloalkyl, CN, $OR^7$, $SR^7$, $NR^7R^7$, $C(O)R^7$ or $C_{1-6}$-alkyl;

$R^5$ is H, $C_{1-6}$-alkyl or $C_{3-6}$-cycloalkyl optionally substituted with 1-3 substituents of $R^7$;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and each $R^7$, independently, is H, F, Cl, Br, I, haloalkyl, CN, OH, $NO_2$, $NH_2$, $C_{1-8}$-alkyl; —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$"cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl, provided the compound is not N5-(3-(7H-pyrrolo[2,3-d]pyrimidin-4-yl)pyridin-2-yl)-6-methyl-N1-(2-methyl-5-(trifluoromethyl)phenyl)isoquinoline-1,5-diamine and 445-(3-(7H-pyrrolo[2,3-d]pyrimidin-4-yl)pyridin-2-ylamino)-6-methylisoquinolin-1-ylamino)benzonitrile.

In another embodiment, the compounds or a stereoisomer, tautomer or pharmaceutically acceptable salt thereof, are defined by a general Formula II-B

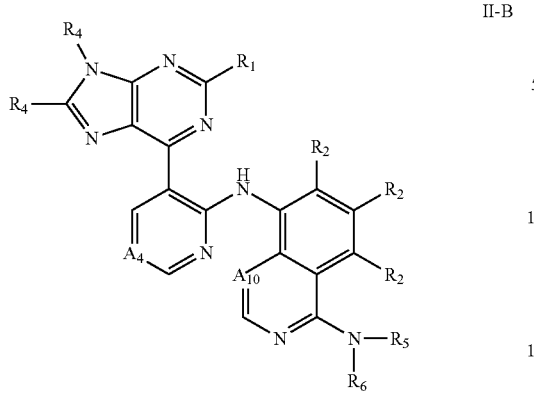

II-B

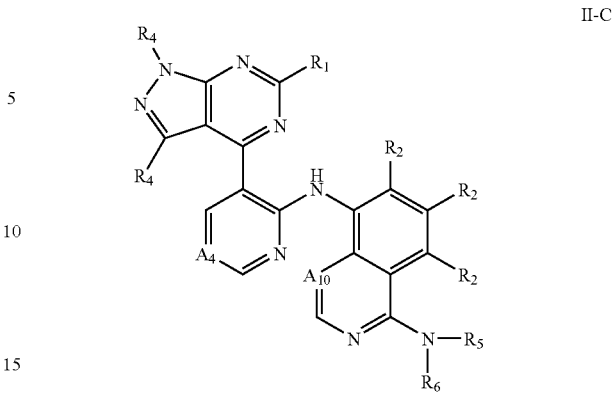

II-C wherein $A^4$ is $CR^2$ or N;

$A^{10}$ is CH or N;

$R^1$ is H, halo, haloalkyl, CN, $OR^7$, $SR^7$, $NR^7R^7$, $C(O)R^7$ or $C_{1-6}$-alkyl;

each $R^2$ independently, is H, halo, haloalkyl, CN, $OR^7$, $SR^7$, $NR^7R^7$, $C(O)R^7$ or $C_{1-6}$-alkyl;

each $R^4$, independently, is H, halo, haloalkyl, CN, $OR^7$, $SR^7$, $NR^7R^7$, $C(O)R^7$ or $C_{1-6}$-alkyl;

$R^5$ is H, $C_{1-6}$-alkyl or $C_{3-6}$-cycloalkyl optionally substituted with 1-3 substituents of $R^7$;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and each $R^7$, independently, is H, F, Cl, Br, I, haloalkyl, CN, OH, $NO_2$, $NH_2$, $C_{1-8}$-alkyl, —O—$C_{1-8}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds or a stereoisomer, tautomer or pharmaceutically acceptable salt thereof, are defined by a general Formula II-C wherein $A^4$ is $CR^2$ or N;

$A^{10}$ is CH or N;

$R^1$ is H, halo, haloalkyl, CN, $OR^7$, $SR^7$, $NR^7R^7$, $C(O)R^7$ or $C_{1-6}$-alkyl;

each $R^2$ independently, is H, halo, haloalkyl, CN, $OR^7$, $SR^7$, $NR^7R^7$, $C(O)R^7$ or $C_{1-6}$-alkyl;

each $R^4$, independently, is H, halo, haloalkyl, CN, $OR^7$, $SR^7$, $NR^7R^7$, $C(O)R^7$ or $R^5$ is H, $C_{1-6}$-alkyl or $C_{3-6}$-cycloalkyl optionally substituted with 1-3 substituents of $R^7$;

$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and each $R^7$, independently, is H, F, Cl, Br, I, haloalkyl, CN, OH, $NO_2$, $NH_2$, $C_{1-8}$-alkyl, —O—$C_{1-8}$-alkyl, —$C_{1-6}$-alkyl-O—$C_{1-6}$-alkyl, —$C_{1-6}$-alkyl-S—$C_{1-6}$-alkyl, $C_{1-8}$-alkyl, —N-di-$C_{1-8}$-alkyl, —$C_{1-6}$-alkyl-NH—$C_{1-6}$alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of Formula I include compounds wherein one of $A^1$ and $A^2$ is N, in conjunction with any of the above or below embodiments.

In another embodiment, the compounds of Formula I include compounds wherein $A^1$ is N, in conjunction with any of the above or below embodiments.

In another embodiment, the compounds of Formula I include compounds wherein $A^2$ is N, in conjunction with any of the above or below embodiments.

In another embodiment, the compounds of Formula I include compounds wherein $A^5$ is N, in conjunction with any of the above or below embodiments.

In another embodiment, the compounds of Formula I include compounds wherein $A^6$ is N, in conjunction with any of the above or below embodiments.

In another embodiment, the compounds of Formula I or II include compounds wherein $A^3$ is N, in conjunction with any of the above or below embodiments.

In another embodiment, the compounds of Formula I or II include compounds wherein $A^4$ is N, in conjunction with any of the above or below embodiments.

In another embodiment, the compounds of Formula I or II include compounds wherein one of $A^7$, $A^8$ and $A^9$ is N, in conjunction with any of the above or below embodiments.

In another embodiment, the compounds of Formula I or II include compounds wherein each $R^2$, independently, is halo, haloalkyl, $NO_2$, CN, $NR^7R^7$, $OR^7$, $SR^7$, $C(O)R^7$, $S(O)_2R^7$, $C_{1-10}$-alkyl or $C_{3-10}$-cycloalkyl, in conjunction with any of the above or below embodiments.

In another embodiment, the compounds of Formula I or II include compounds wherein each $R^2$, independently, is halo, haloalkyl, $NO_2$, CN, $NR^7R^7$, $OR^7$ or $C_{1-10}$-alkyl, in conjunction with any of the above or below embodiments.

In another embodiment, the compounds of Formula I or II include compounds wherein each $R^2$, independently, is H, halo, haloalkyl, or $C_{1-10}$-alkyl, in conjunction with any of the above or below embodiments.

In another embodiment, the compounds of Formula I or II include compounds wherein $R^3$ is $NR^5R^6$, $NR^5C(O)R^6$, $NR^5C(S)R^6$, $NR^5C(O)NR^5R^6$, $NR^5(COOR^6)$, $NR^5S(O)_2NR^5R^6$ or $NR^5S(O)_2R^6$, in conjunction with any of the above or below embodiments.

In another embodiment, the compounds of Formula I or II include compounds wherein $R^3$ is $NR^5R^6$, $NR^5C(O)R^6$ or $NR^5S(O)_2R^6$, in conjunction with any of the above or below embodiments.

In another embodiment, the compounds of Formula I or II include compounds wherein $R^3$ is $NR^5R^6$, in conjunction with any of the above or below embodiments.

In another embodiment, the compounds of Formula I or II include compounds wherein $R^4$ is H, $NO_2$, $C_{1-10}$-alkyl, $NR^7R^7$, $NR^5R^6$, $C(O)R^7$ or $C(O)R^6$, in conjunction with any of the above or below embodiments.

In another embodiment, the compounds of Formula II include the compounds of any sub-Formulas, such as compounds of Formula II-A, and II-C. In other embodiments, Formulas I and II and II-A-II-C include each and every exemplary compound, and pharmaceutically acceptable salts thereof, which are described in the Experimentals Methods section hereinbelow (for instance, see Examples 40-78 in Tables I and II).

The invention also provides methods of synthesizing compounds of Formulas I-II. For example, in one embodiment, there is provided a process for synthesizing a compound of Formula I, the process comprising the step of reacting a compound of Formula A

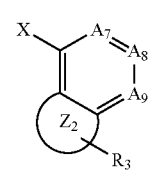

wherein X is a nucleophilic species selected from an amine, an alcohol, a thiol and a carbon nucleophile, and wherein $A^{7-9}$, $Z^2$ and $R^3$ are as described herein, with a compound of Formula B

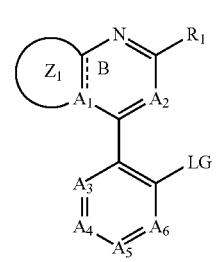

wherein LG is a leaving group selected from a halogen, a metallic species, a boronic acid and a Grignard reagent, and wherein $A^{1-6}$, bond B, $Z^1$ and $R^1$ are as described herein, to synthesize the compound of Formula I. The boronic acid LG may be a borinate ester species, such as those shown herein.

The invention also provides methods of synthesizing compounds of Formulas I-II. For example, in one embodiment, there is provided a process for synthesizing a compound of Formula II-A, the process comprising the step of reacting a compound of Formula II-A-a

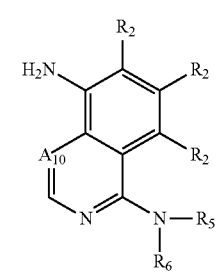

wherein $A^{10}$, $R^2$, $R^5$ and $R^6$ are as described herein, with a compound of Formula II-A-b

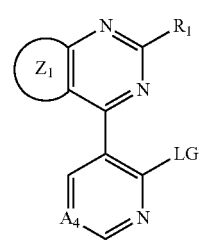

wherein LG is a leaving group selected from a halogen, a metallic species, a boronic acid and a Grignard reagent, and wherein $A^4$, $Z^1$ and $R^1$ are as described herein, to synthesize the compound of Formula II-A. The boronic acid LG may be a borinate ester species, such as those shown herein.

The invention also provides methods of synthesizing compounds of Formulas I-II. For example, in one embodiment, there is provided A process for synthesizing a compound of Formula II-B, the process comprising the step of reacting a compound of Formula II-A-a

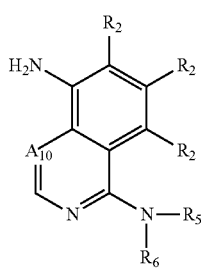

II-A-a wherein $A^{10}$, $R^2$, $R^5$ and $R^6$ are as described herein, with a compound of Formula II-B-b

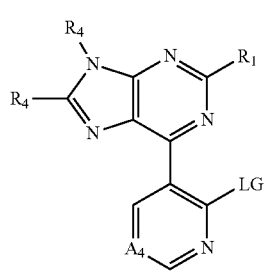

II-B-b wherein LG is a leaving group selected from a halogen, a metallic species, a boronic acid and a Grignard reagent, and wherein $A^4$, $R^4$ and $R^1$ are as described herein, to synthesize the compound of Formula II-B. The boronic acid LG may be a borinate ester species, such as those shown herein.

DEFINITIONS

The following definitions should assist in understanding the invention described herein.

The terms "agonist" and "agonistic" when used herein refer to or describe a molecule which is capable of, directly or indirectly, substantially inducing, promoting or enhancing biological activity of a biological molecule, such as an enzyme or receptor, including B-raf kinase.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$). The term "alkyl" radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl(propargyl), butynyl, and the like.

The term "alkoxy" or "alkoxyl", when used alone or in combination, embraces linear or branched oxygen-containing radicals, each having alkyl portions of one or more carbon atoms. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "fused" when used alone or in reference to a "ring" or "ring system" refers to a bicyclic ring having 2 common atoms. For example, as shown in Formula the two common atoms are both carbon, when Z' is phenyl and is fused to ring Z.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzothiazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —C(=O)—.

The term "aminocarbonyl" denotes an amide group of the formula —C(=O)NH$_2$.

The term "alkylthio" embraces radicals containing a linear or branched alkyl radical, of one to ten carbon atoms, attached to a divalent sulfur atom. An example of "alkylthio" is methylthio, (CH$_3$S—).

The term "haloalkylthio" embraces radicals containing a haloalkyl radical, of one to ten carbon atoms, attached to a divalent sulfur atom. An example of "haloalkylthio" is trifluoromethylthio.

The term "aminoalkyl" embraces linear or branched alkyl radicals having one to about ten carbon atoms any one of which may be substituted with one or more amino radicals. Examples of aminoalkyl radicals include "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the term "Formula II" includes any sub formulas.

The term "pharmaceutically-acceptable" when used with reference to a compound of Formulas I-II is intended to refer to a form of the compound that is safe for administration. For example, a salt form, a solvate, a hydrate or derivative form of a compound of Formula I or of Formula II, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-II are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-II may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I or II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I or II. A "pharmaceutically-acceptable prodrug" as used herein, denotes a prodrug which is pharmaceutically acceptable. Pharmaceutically acceptable modifications to the compounds of Formulas I and II are readily appreciated by those of ordinary skill in the art.

The compound(s) of Formulas I or II may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels Raf kinases in the mammal.

General Synthetic Procedures

The present invention further comprises procedures for the preparation of a compound of Formulas I and II. The compounds of Formulas I, II and II-A-C can be synthesized according to the procedures described in the following exemplary schematic methods 1-5j, wherein the substituents are as defined for Formulas I, II, II-A, II-B and II-C above, except where further noted. The synthetic methods described below are merely exemplary, and the compounds of the invention may be synthesized by alternate routes as appreciated by persons of ordinary skill in the art.

The following list of abbreviations used throughout the specification represent the following and should assist in understanding the invention:

| | |
|---|---|
| ACN, MeCN | acetonitrile |
| BSA | bovine serum albumin |
| $Cs_2CO_3$ | cesium carbonate |
| $CHCl_3$ | chloroform |
| $CH_2Cl_2$, DCM | dichloromethane, methylene chloride |
| mCPBA | meta-chloro peroxybenzoic acid |
| DIBAL | diisobutylaluminum hydride |
| DIC | 1,3-diisopropylcarbodiimide |
| DIEA,$(iPr)_2$NEt | diisopropylethylamine |
| DME | dimethoxyethane |
| DMF | dimethylformamide |
| DMSO | dimethylsulfoxide |
| EDC | 1-(3-dimethylaminopropyl)-3-ethylcarbodiimide |
| $Et_2O$ | diethyl ether |
| EtOAc | ethyl acetate |
| FBS | fetal bovine serum |
| G, gm | gram |
| h, hr | hour |
| $H_2$ | hydrogen |
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HPLC | high pressure liquid chromatography |
| IPA, IpOH | isopropyl alcohol |
| $K_2CO_3$ | potassium carbonate |
| KI | potassium iodide |
| $MgSO_4$ | magnesium sulfate |
| MeOH | methanol |
| $N_2$ | nitrogen |
| $NaBH_4$ | sodium borohydride |
| $NaHCO_3$ | sodium bicarbonate |
| $NaOCH_3$ | sodium methoxide |
| NaOH | sodium hydroxide |
| $Na_2SO_4$ | sodium sulfate |
| PBS | phospate buffered saline |
| Pd/C | palladium on carbon |
| $Pd(PPh_3)_4$ | palladium(0)triphenylphosphine tetrakis |
| Pd(dppf)Cl2 | palladium(1,1-bisdiphenylphosphinoferrocene) II chloride |
| Pd2(dba)3 | bis(dibenzylideneacetone) palladium |
| POCl3 | phosphorus oxychloride |
| PyBop | benzotriazol-1-yl-oxy-tripyrrolidino-phosphonium hexafluorophosphate |
| RT | room temperature |
| TBTU | O-benzotriazol-1-yl-N,N,N',N'-tetramethyluronium tetrafluoroborate |
| TEA, Et3N | triethylamine |
| TFA | trifluoroacetic acid |
| THF | tetrahydrofuran |

Scheme 1a

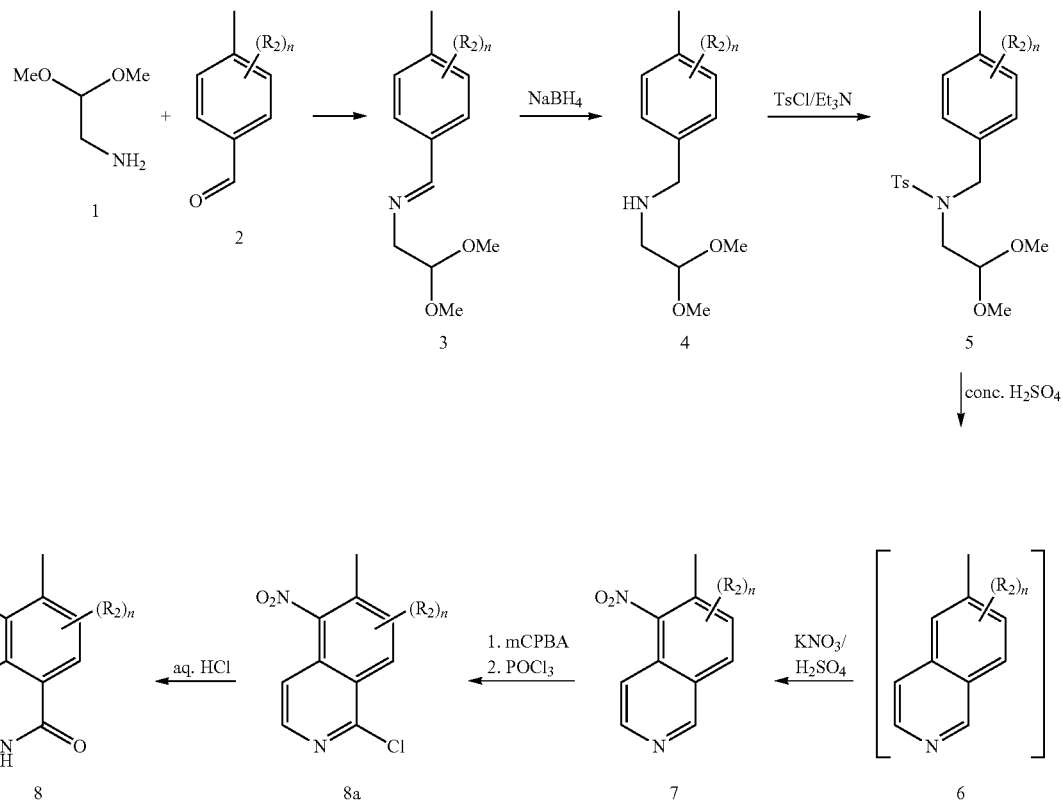

A method for making intermediates 8, which are useful for making various of the compounds of Formulas I-II (where fused ring $Z^2$ is a pyridine ring; this fused ring system is commonly referred to herein as the "B" ring), is described in scheme 1. As shown, a ketone-protected amine 1 can be condensed with a benzaldehyde 2 to form the corresponding imine 3. Imine 3 can be reduced with known reducing reagents, such as $NaBH_4$, under suitable conditions to provide the corresponding amine adduct 4. The amino functionality of compound 4 may be protected with a suitable protecting group, such as a tosylate as shown, under suitable conditions to provide the protected amine compound 5. Compound 5 can be cyclized by treatment with a suitable acid, such as conc. $H_2SO_4$, which deprotects the amine and carbonyl groups in situ to yield an isoquinoline compound 6. The isoquinoline compound 6 may be nitrated using $KNO_3$ under known acidic conditions to form the nitro-compound 7. As shown, a nitro-substituted isoquinoline 7 can be halogenated with a chlorine atom by known methods, such as with an oxidant (mCPBA) in the presence of a known chlorinating reagent such as $POCl_3$, to form the chloro-adduct compound 8a. The chloring of compound 8a can subsequently be converted to the corresponding ketone using conventional methods, such as with aqueous acidic conditions, as shown above in Scheme 1, to yield the corresponding, useful nitro-lactam intermediate 8.

Scheme 1b

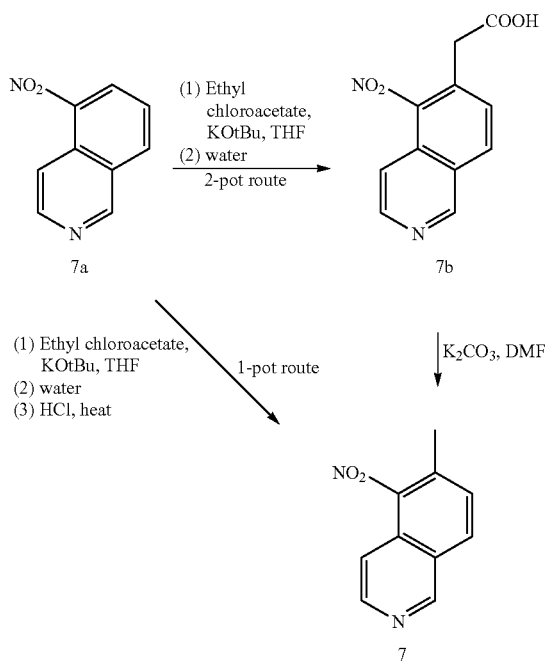

A more efficient, time and cost effective method for making useful intermediates 7, shown in scheme 1a, which are useful for making various of the compounds of Formulas I-II, is described in scheme 1b. As shown, 5-nitroisoquinoline 7a can be reacted with ethyl chloroacete in the presence of a suitable base, such as potassium t-butoxide and a stuiable solvent to afford the in-situ ethyl acetate ester adduct (not shown). Particularly, the reaction can be run at temperatures of about −40° C. to 0° C. and is complete within minutes. Water is then added, and the reaction is stirred at RT for about 10-20 hrs, which soponifies the ester to the corresponding acid 7b, as shown. The acid 7b can be isolated, by washing the ester with isopropyl acetate, treating the aqueous layer with charcoal to remove any colored impurities. HCl is then added and the pH is adjusted to about 0.5 and the mixture is heated at about 90° C. for about 6 hrs. In a 1-pot process, the in-situ acid can be treated again with charcoal to remove impurities, and pH can be adjusted to about 4.0 with NaOH and the precipitated product 7 can be isolated by simple filtration. In this fashion, the product compound 7 can be obtained in good yields, if about 70% to about 80% yield, with >97% purity by HPLC.

Alternatively, in a 2-step process, the acid may be isolated and purified, and then treated with a suitable base, such as potassium carbonate, to eliminate $CO_2$ and afford the corresponding 6-methyl-5-nitroisoquinoline 7 in good yields. Such a process also works on various other compounds, such as those where the nitrogen atom is located in a different point, including 5-methyl-6-nitroquinoline, 7-methyl-8-nitroquinoline, and 2-methyl-1-nitronaphthalene compounds. It is envisioned herein that this one or two-step process may be applicable for other nitro-aromatic rings we all, including without limitation, nitrophenyl ring, benzofused heteroaromatic rings containing nitro groups, and the like.

This 1- or 2-pot process is more efficient than what was previously known in the art. For example, 5-nitroisoquinoline is commercially available, and relatively inexpensive (about 1 kg costs less than $500). Previous synthesis of 6-methyl-5-nitroisoquinoline was accessible in a 3-step sequence through a Pomeranz-Fritsch isoquinoline synthesis starting from 4-methyl benzaldehyde. The transformations involved excess amounts of several reagents (especially titanium tetrachloride) and require time consuming and tedious work-ups. The intermediate can then be nitrated in good selectivity to afford the targeted compound. The nitration step is carried out under strongly acidic conditions and it leads to the formation of large amounts of inorganic salts during the work-up. A more economic approach is therefore desirable. Further, selective ortho-functionalization of nitro aromatic compounds with alkyl chloroacetates have been described in Tomioka et al, *J. Heterocyclic Chem,* 2003, 40, pg 1051; Makoska et al, *Synthesis,* 1988, 1007. The products have been soponified and decarboxylated to afford the desired methyl isoquinolines, as described in Bull et al, *Synlett,* 1996, 647.

Scheme 2a

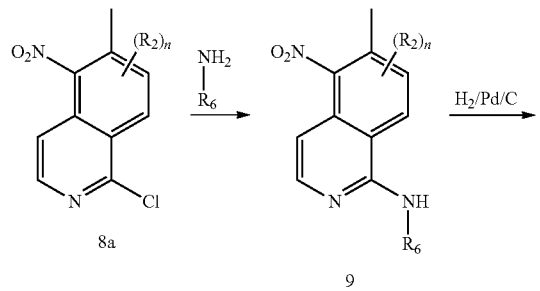

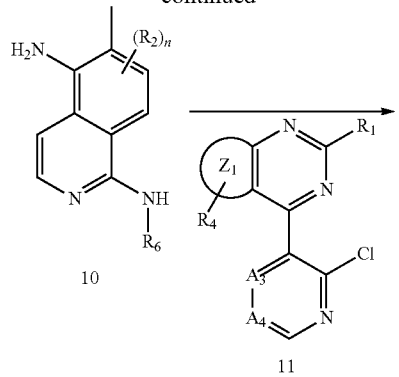

10

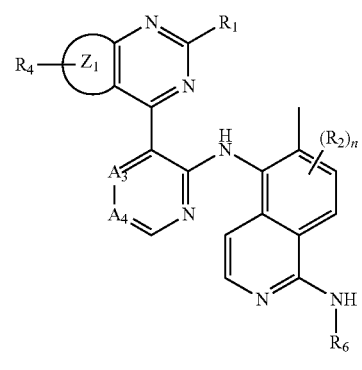

12

A method for making a compound 12 of Formulas I-II (where $Z^2$ is a pyridine ring and X is —NH—, $A^1$ is C, $A^2$ is N, $A^6$ is N and $A^{7-9}$ are each, independently, CH or $CR^2$, and $R^3$ is —$NR^5R^6$ wherein $R^5$ is H and $R^6$ is a ring moiety including, without limitation, an aryl group; $R^6$ is often referred to herein as the "A" ring) is described in scheme 2a. As shown, the chlorine of compound 8a can be displaced by an aryl amine under suitable conditions to generate an aryl amine-linked isoquinoline 9. The nitro group of compound 9 can be reduced to compound 10 using traditional methods, such as by hydrogenation in the presence of a suitable palladium catalyst as shown in scheme 2 above. The amino functionality of compound 10 (wherein X of compounds of Formulas I and II is NH or NR) may be reacted with a desirable leaving group ("LG") substituted pyridine compound 11, such as the chloro-pyridine 11 to provide the final compound 12, of Formula I or II.

Scheme 2b

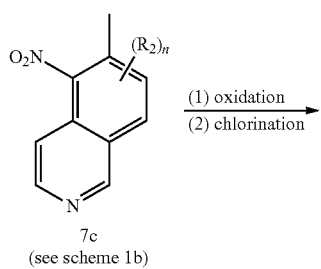

7c
(see scheme 1b)

(1) oxidation
(2) chlorination

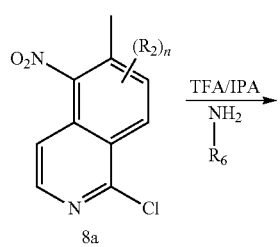

8a

TFA/IPA
NH$_2$
R$_6$

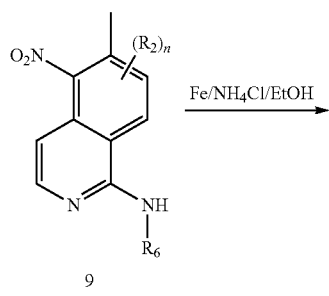

9

Fe/NH$_4$Cl/EtOH

-continued

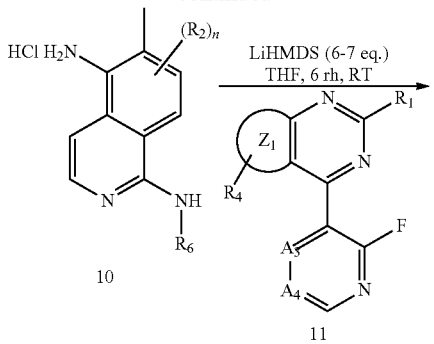

10

LiHMDS (6-7 eq.)
THF, 6 rh, RT

11

12

A method for making a compound 12 of Formulas I-II (where $Z^2$ is a pyridine ring and X is —NH—, $A^1$ is C, $A^2$ is N, $A^6$ is N and $A^{7-9}$ are each, independently, CH or $CR^2$, and $R^3$ is —$NR^5R^6$ wherein $R^5$ is H and $R^6$ is a ring moiety including, without limitation, an aryl group; $R^6$ is often referred to herein as the "A" ring) is described in scheme 2b. As shown, a compound 7c, similar to compound 7 in scheme 1b, can be oxidized followed by chlorination with POCl$_3$ to afford compound 8a. The chlorine of compound 8a can be displaced by an aryl amine under suitable conditions to generate an aryl amine-linked isoquinoline 9. The nitro group of compound 9 can be reduced to compound 10 using traditional methods, such as by hydrogenation in the presence of a suitable palladium catalyst as shown in scheme 2a above. The amino functionality of compound 10 (wherein X of compounds of Formulas I and II is NH or NR) may be reacted with a desirable leaving group ("LG") substituted pyridine compound 11, such as the chloro-pyridine 11 to provide the final compound 12, of Formula I or II. Note that scheme 2b illustrates compounds comprising a fused $Z^1$ ring. However, the process is not so limited, and may be extended to compounds sans or without a fused $Z^1$ ring, and having desirably substituted pyridine or pyrimidine D rings (not shown), as described in co-pending PCT patent application serial no. 2006049187.

Scheme 3

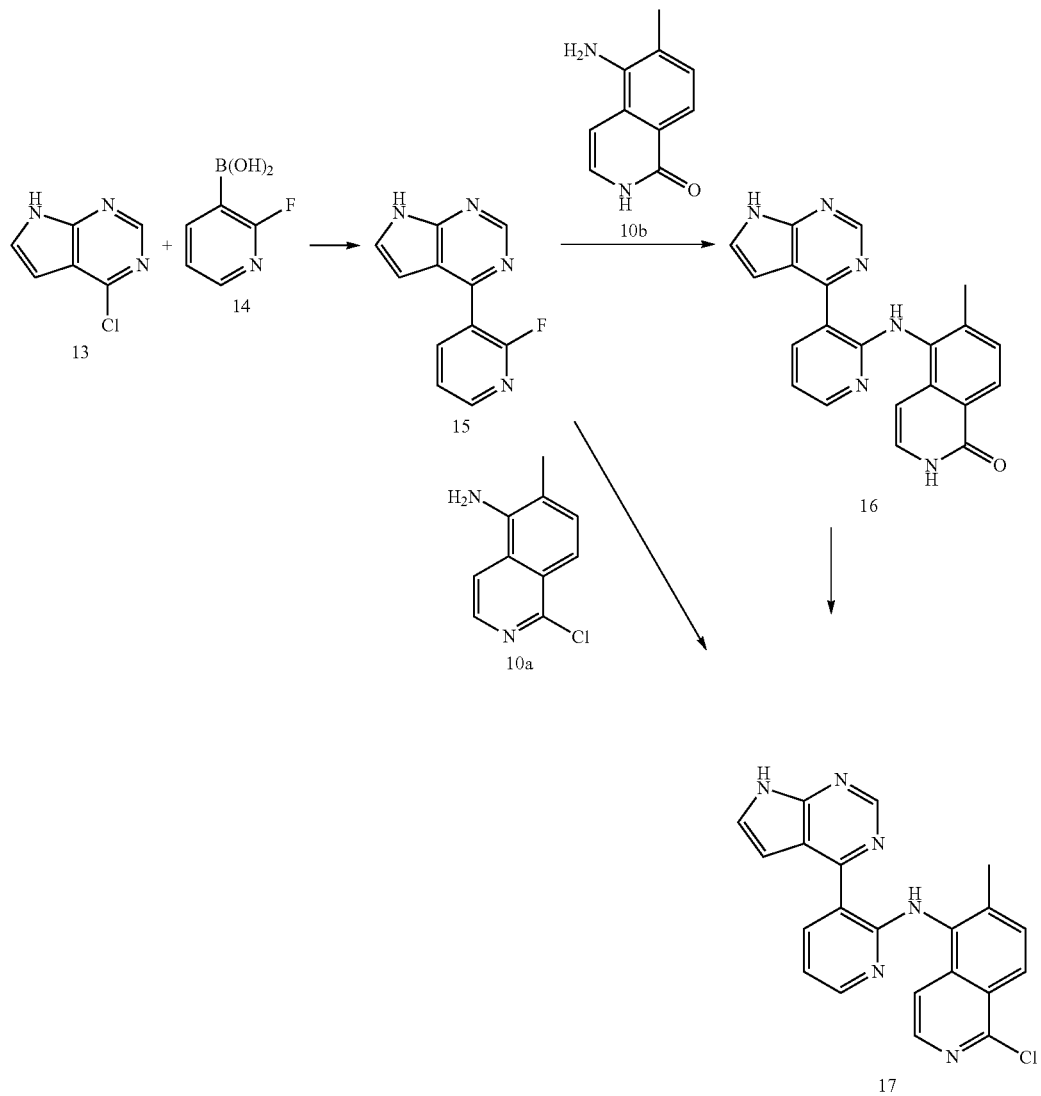

A method for making a compound 17 of Formulas I-II (where $Z^1$ is a pyrrole, $Z^2$ is a pyridine, X is —NH—, $A^1$ is C, $A^2$ is N, $A^6$ is N and $A^{7-9}$ are each, independently, CH or $CR^2$) is described in scheme 3. For the purposes of the exemplary compounds described hereinbelow, this method or general synthetic strategy is designated as Method A. As shown, the chlorine of compound 13 can be reacted with a fluoro-pyridine boronic acid 14 under suitable conditions, such as Suzuki or Suzuki-like conditions, to generate the aryl couple adduct 15. Suzuki conditions are described hereinbelow. The fluoro group of compound 15 can be displaced either by the amine of compound 10b using traditional methods to form the amino-coupled adduct compound 16, or by the amine of compound 10a using traditional methods to form the amino-coupled adduct compound 17. The carbonyl of compound 16 can be converted to the corresponding chloride compound 17, using $POCl_3$, which chlorine can then be displaced by a suitable nucleophile, such as an aryl amine, under suitable conditions to generate an aryl amine-linked isoquinoline compounds of Formulas I and II (not shown in scheme 3).

The Suzuki method of forming compound 15 is a reaction using a borane reagent, such as a dioxaborolane intermediate (not shown) or a boronic acid 14 and a suitable leaving group containing reagent, such as the halo-substituted compound 13. As appreciated to one of ordinary skill in the art, Suzuki reactions also use palladium as a catalyst, in the presence of a suitable base, such as a carbonate base, bicarbonate or an acetate base, in a suitable solvent, such as toluene, acetonitrile, DMF or an aqueous-organic solvent combination (such as dioxanes/water) or a biphasic system of solvents (such as toluene/aq. $NaCO_3$). Suitable palladium reagents include $Pd(PPh_3)_4$, $Pd(OAc)_2$ or $Pd(dppf)Cl_2$. Where LG is a halide, the halide may be an iodide, a bromide or even a chloride (chloro-pyridyl or chloro-picolinyl B rings undergo suzuki reactions in the presence of $Pd(OAc)_2$). In addition, a corresponding halo intermediate, the C-D ring piece or the B-A ring piece, may be converted to the borane, such as the dioxaborolane as described in Scheme 6. Other LGs are also suitable. For example, Suzuki couplings are known to occur with a sulfonate, such as trifluoromethanesulfonate, as the leaving group.

Scheme 3a

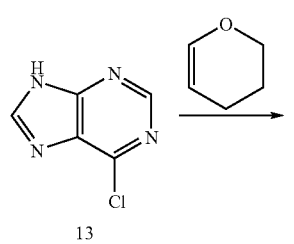
13

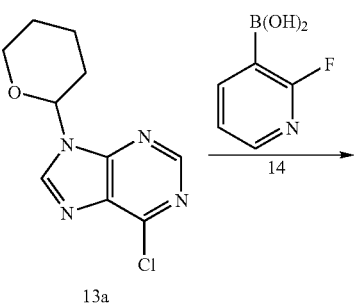
13a

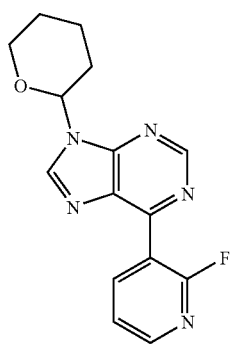
15

Scheme 3a describes a method for making a protected form of compound 15 of scheme 3 above. As shown, the amine of compound 13 can be reacted with a dihydro-2H-pyran under suitable conditions to generate the protected adduct 13a, as shown. The nitrogen-protected purine compound 13a can be reacted in a Suzuki-like fashion, as described above, with a desired boronic acid 14 to prepare the coupled adduct compound 15.

Scheme 3b

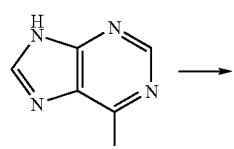
16

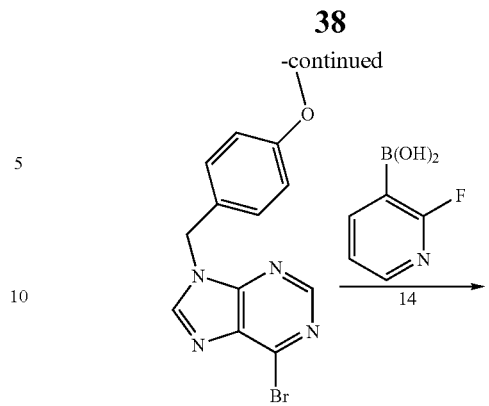
17

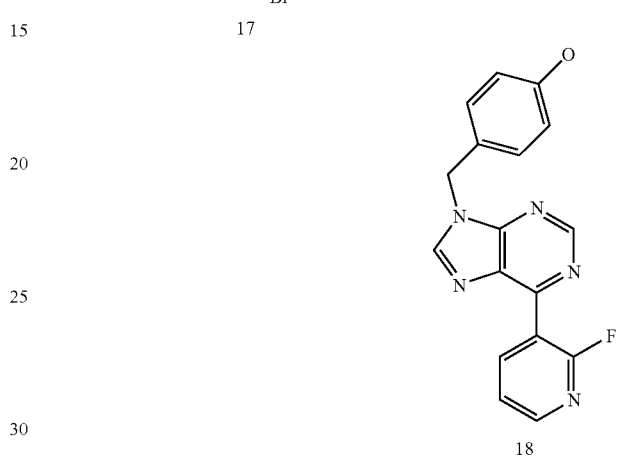
18

Alternatively, Scheme 3b illustrates a method for making another protected form of compound 15 of scheme 3 above, i.e. a compound 18. As shown, the amine of a bromo-purine compound 16 can be reacted with methoxy-benzyl chloride under suitable basic conditions to generate the protected adduct 17, as shown. The nitrogen-protected purine compound 17 can be reacted in a Suzuki-like fashion, as described above with a desired boronic acid 14 to prepare the coupled adduct compound 18.

Scheme 3c

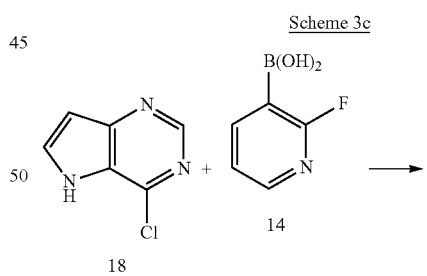
18

19

Scheme 3c illustrates a method for making a fluoro-substituted pyridine compound 19. As shown, the amine of a chloro-pyrrolo-pyrimidine compound 18 can be reacted in a Suzuki-like fashion, as described above with a desired boronic acid 14 to prepare the coupled adduct compound 19. See the Examples described in more details herein for specific conditions.

Scheme 3d

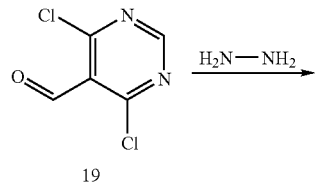

19

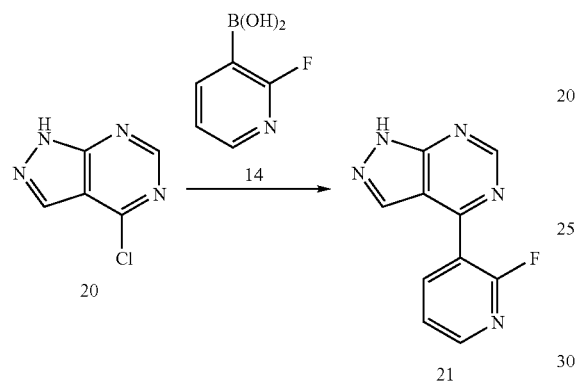

Scheme 3d illustrates a method for making yet another halo-substituted pyrido-$Z^1$-fused pyrimidine compound 21. As shown, a chloro-pyrimidine aldehyde 19 can be condensed with hydrazine to effectively close the ring and form compound 20. Compound 20 can then be reacted in a Suzuki-like fashion, as described above with a desired boronic acid 14 to prepare the coupled adduct compound 21. See the Examples described in more details herein for specific conditions for each step.

Scheme 4

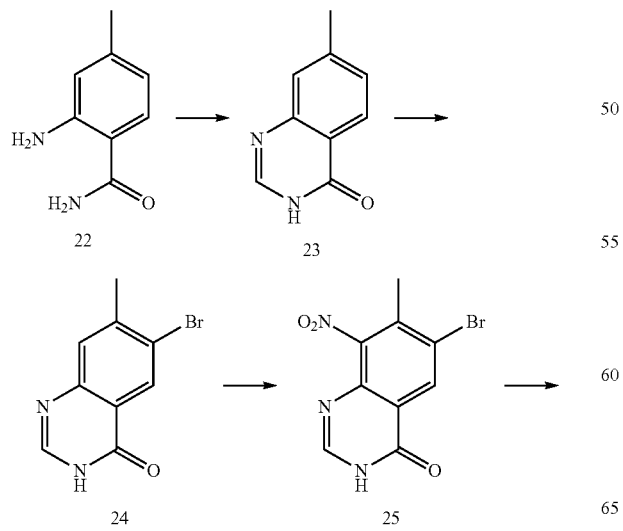

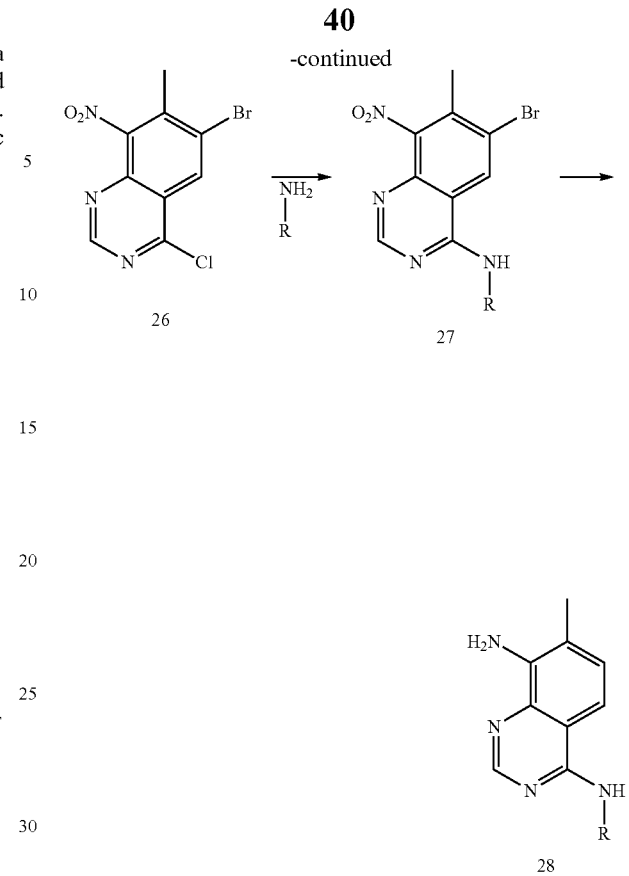

Scheme 4 illustrates a method for making yet another amino-substituted quinazoline (wherein fused $Z^2$ ring is a pyrimidine) compound 28. As shown, a para-amido-m-amino toluene 22 can be cyclized with formic acid or formaldehyde to form ring-closed compound 23. Compound 23 can then be brominated, under standard conditions, with a suitable bromine source to prepare the brominated compound 25. Compound 25 can then be nitrated, under known conditions, with a suitable nitrate source to prepare the corresponding nitro-compound 26. The chloride of compound 26 can be displaced with a suitable nucleophile, such as the substituted amine (see also scheme 1) to prepare the amino-substituted compound 27. Compound 27 can be reduced, under known conditions, to reduce the nitro group to the corresponding amine group and eliminate the bromine, prepare the corresponding compound 28. See the Examples described in more details herein for specific conditions for each step.

Scheme 5a (Method A)

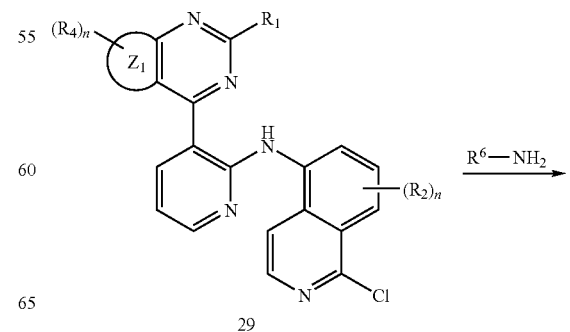

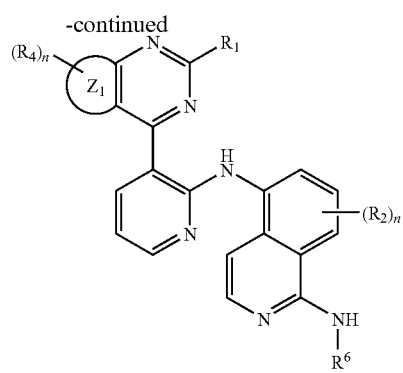

30

Scheme 5a illustrates a method for preparing compounds of Formulas I and II, wherein X is NH, $Z^2$ is a pyridine ring, and $R^3$ is an amino-linked ring moiety (see also schemes 2 and 3a). For the purposes of the exemplary compounds described hereinbelow, this method or general synthetic strategy is designated as Method A. As shown, the chlorine of compound 29 can be displaced by an aryl amine under suitable conditions to generate an aryl amine-linked isoquinoline 30. The amino group is not the only nucleophile which may be used here. Other suitable nucleophilic species may be used to displace the chloride, as desired and appreciated by those skilled in the art. Scheme 5a thus illustrates a nice method for varying the $R^5$ and/or $R^6$ groups.

Similarly, $R^3$ groups may be amide linked groups, urea-linked groups and others, as defined herein. Amides may be made from the chloride or other LG pre-cursor (not shown). The LG can be displaced by a carbon nucleophile and then oxidized up to the corresponding carboxylic acid. The acid functional group can be activated with known activating groups, such as an acid chloride, and erected with desired species to form the desired compounds of Formulas I and II. For example, to form an amide bond, an ester, a carbamate, a urea, and the like, each of the two starting materials must possess one or the other of an electrophilic ($E^+$) and a nucleophile (Nu). The acid may be the $E^+$ by activating it with a component "X". X refers generally to a "leaving group" such as a halide (bromine, chlorine, iodine or fluorine), alkylsulfonate and other known groups (also see definitions herein). Nu⁻ refers generally to a nucleophilic species such as a primary or secondary amine, an oxygen, a sulfur or a anionic carbon species. Examples of nucleophiles include, without limitation, amines, hydroxides, alkoxides and the like. $E^+$ refers generally to an electrophilic species, such as the carbon atom of a carbonyl, which is susceptible to nucleophilic attack or readily eliminates. Examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP and carbodiimides (DCC, EDC and the like), and other electrophilic species including halides, isocyanates, daizonium ions and the like.

The coupling of rings B and A (not shown) can be brought about using various conventional methods. For example, an amide or a sulfonamide linkage where the Nu- is an amine can be made utilizing an amine on either the B or A rings and an acid chloride or sulfonyl chloride on the other of either the B or A rings. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates where Nu- is an amine, anhydrides where Nu- is an oxygen, reverse amides where Nu- is an amine and E+ is an acid chloride, ureas, thioamides and thioureas where the respective carbonyl oxygen is a sulfur, thiocarbamates where the respective carbonyl oxygen and/or carbamate oxygen is a sulfur, and the like, can be made utilizing similar methods as described for the amide or sulfonamide bond above. While the above methods are so described, they are not exhaustive, and other methods for linking rings A and B together may be utilized as appreciated by those skilled in the art.

The amide may be converted to the corresponding thioamide with a suitable reagent, such as Lawesson's Reagent, as appreciated by those skilled in the art.

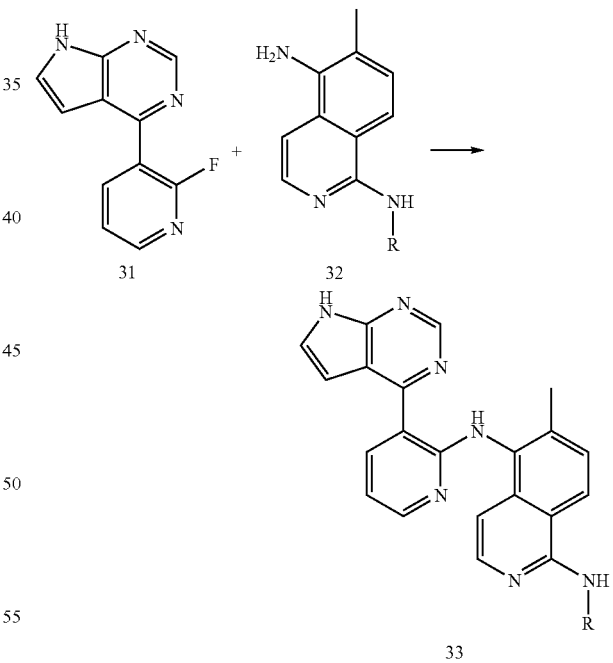

Scheme 5b illustrates an alternative method for preparing compounds of Formulas I and II, wherein X is NH, $Z^2$ is a pyridine ring, and $R^3$ is an amino-linked ring moiety (see also schemes 2 and 3a). For the purposes of the exemplary compounds described hereinbelow, this method or general synthetic strategy is designated as Method A'. As shown, the flourine of compound 31 can be displaced by the amino group of compound 32 under suitable conditions to generate an aryl amine-linked isoquinoline 33. Similarly, an alcohol group may also be used to form compounds of Formulas I and II wherein X is O, Scheme 5b thus illustrates a nice method for keeping constant the $R^5$ and/or $R^6$ groups.

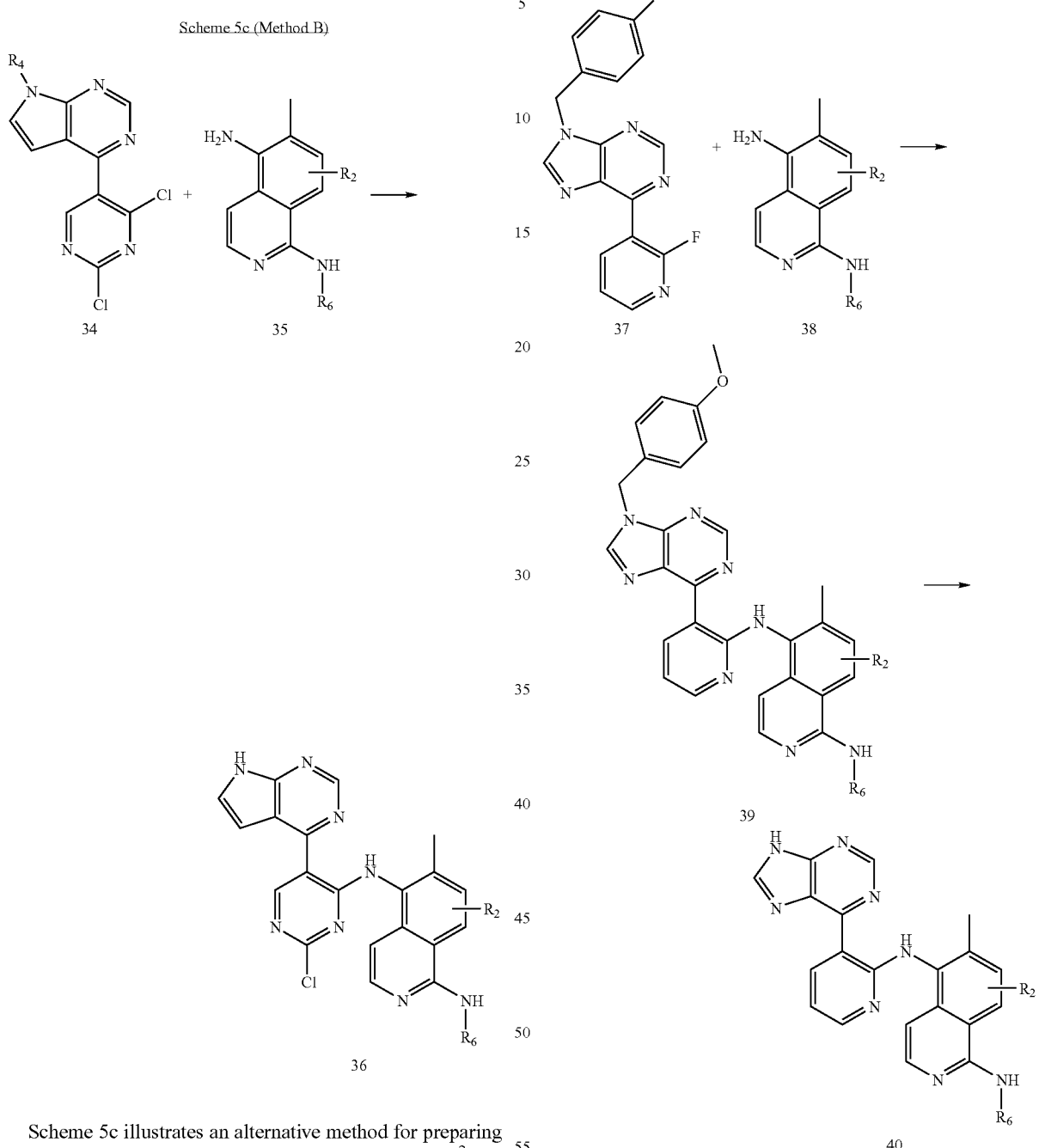

Scheme 5c illustrates an alternative method for preparing compounds of Formulas I and II, wherein X is NH, $Z^2$ is a pyridine ring, $A^4$ is N (a pyrimidine C ring) and $R^3$ is an amino-linked ring moiety (see also schemes 2 and 3a). For the purposes of the exemplary compounds described hereinbelow, this method or general synthetic strategy is designated as Method B. As shown, the chlorine of compound 34 can be displaced by the amino group of compound 35 under suitable conditions to generate an aryl amine-linked isoquinoline 36. Similarly, an alcohol group may also be used to form compounds of Formulas I and II wherein X is O, Scheme 5c thus illustrates a method for having desired $R^2$ substituents in the C ring of compounds of Formulas I and II.

Scheme 5d illustrates an alternative method for preparing compounds of Formulas I and II, wherein X is NH, $Z^1$ is an imidazole fused ring, $Z^2$ is a pyridine ring, $A^4$ is N (a pyrimidine C ring) and $R^3$ is an amino-linked ring moiety (see also schemes 2 and 3a). For the purposes of the exemplary compounds described hereinbelow, this method or general synthetic strategy is designated as Method C. As shown, the chlorine of protected imidazole fused compound 37 can be displaced by the amino group of compound 38 under suitable conditions to generate an aryl amine-linked isoquinoline 39.

Similarly, an alcohol group may also be used to form compounds of Formulas I and II wherein X is O. Compound 39 can then be deprotected to afford the desired compound of Formulas I and II. Compound 39 may then be functionalized, for example, it may be alkylated using a suitable base and alkylating agent, to install desired $R^2$ substituents in the imidazole fused ring.

displaced by the amino group of compound 42 under suitable conditions to generate an aryl amine-linked isoquinoline 43. Similarly, an alcohol group may also be used to form compounds of Formulas I and II wherein X is O. Compound 43 can then be deprotected to afford the desired compounds 44 of Formulas I and II. Compound 43 may then be functionalized, for example, it may be alkylated using a suitable base and alkylating agent, to install desired $R^2$ substituents in the imidazole fused ring.

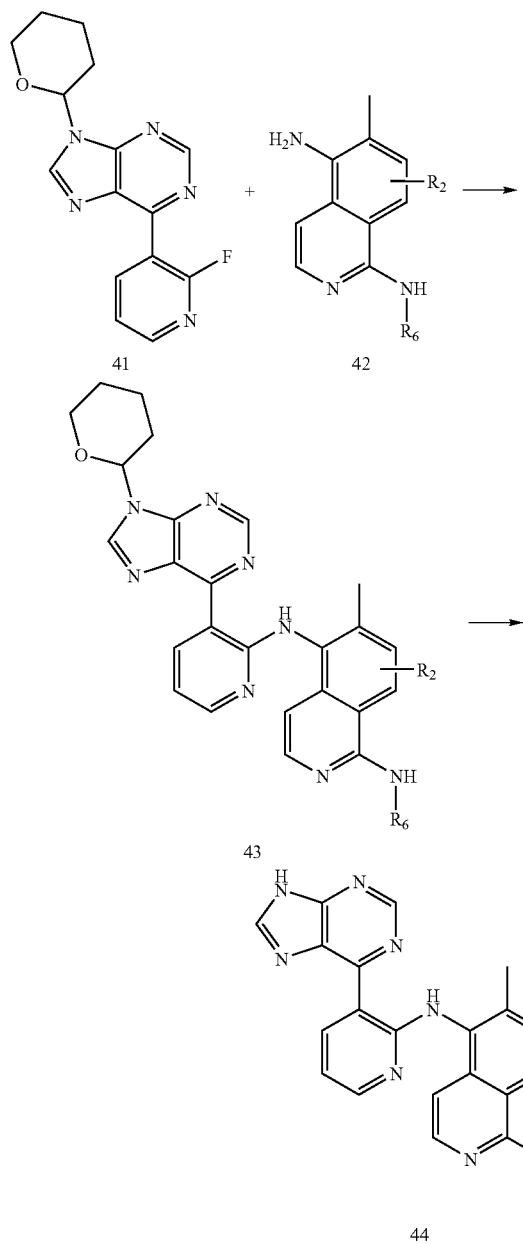

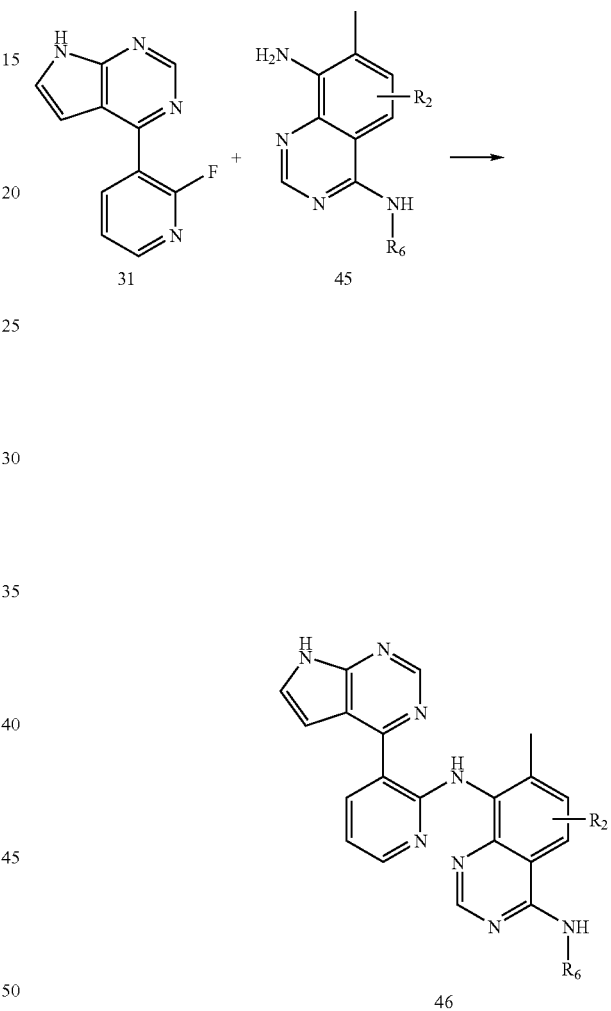

Scheme 5e illustrates an alternative method for preparing compounds of Formulas I and II, wherein X is NH, $Z^1$ is an imidazole fused ring, $Z^2$ is a pyridine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method D. As shown, the chlorine of protected imidazole fused compound 41 can be displaced by the amino group of compound 42 under suitable Scheme 5f illustrates an alternative method for preparing compounds of Formulas I and II, wherein X is NH, $Z^1$ is a pyrrole fused ring, $Z^2$ is a pyridine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method E. As shown, the flourine of compound 31 can be displaced by the amino group of compound 45 under suitable conditions to generate an aryl amine-linked isoquinoline 46. Similarly, an alcohol group may also be used to form compounds of Formulas I and II wherein X is O. Compound 46 may then be functionalized, for example, it may be alkylated using a suitable base and alkylating agent, to install desired $R^4$ substituents in the pyrrole fused ring.

Scheme 5g (Method F)

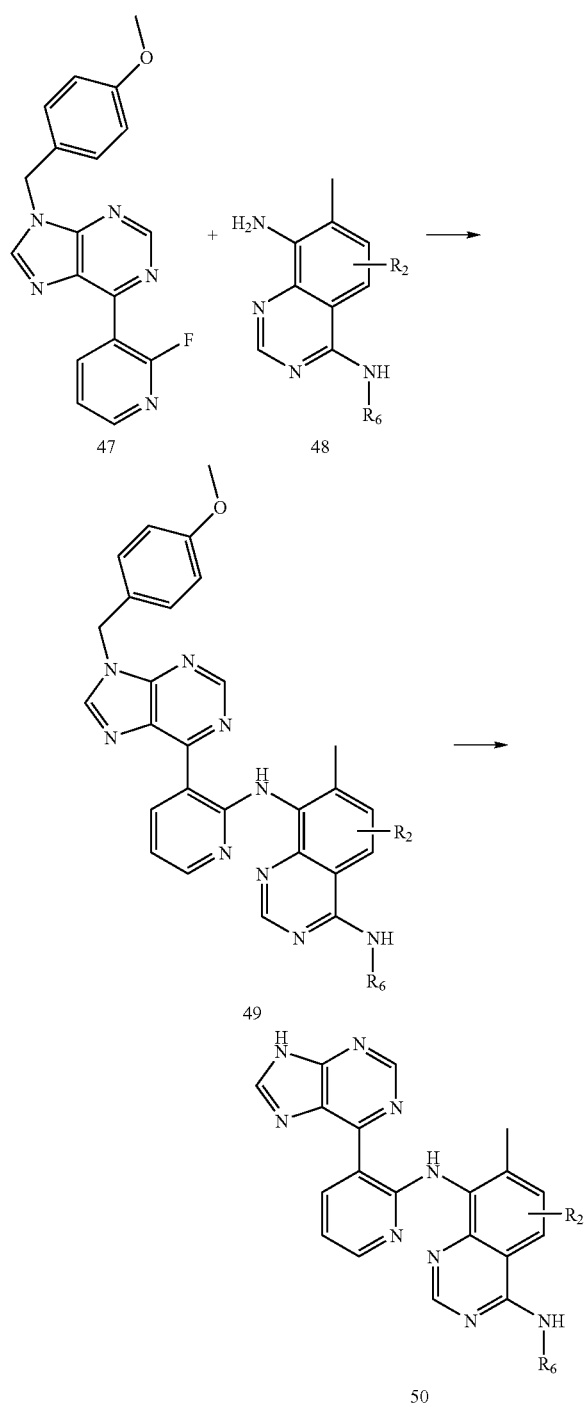

may also be used to form compounds of Formulas I and II wherein X is O. Compound 49 can then be deprotected to afford the desired compounds 50 of Formulas I and II. Compound 49 may then be functionalized, for example, it may be alkylated using a suitable base and alkylating agent, to install desired $R^4$ substituents in the imidazole fused ring.

Scheme 5h (Method G)

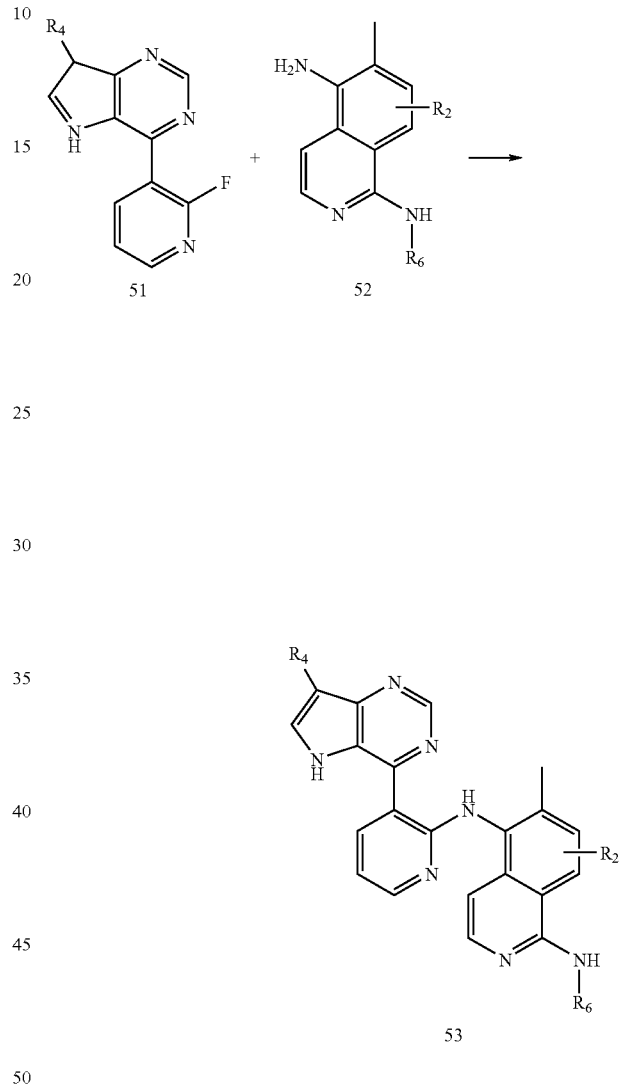

Scheme 5g illustrates an alternative method for preparing compounds of Formulas I and II, wherein X is NH, $Z^1$ is a fused imidazole ring, $Z^2$ is a pyrimidine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method F. As shown, the flourine of compound 47 can be displaced by the amino group of compound 48 under suitable conditions to generate an aryl amine-linked isoquinoline 49. Similarly, an alcohol group Scheme 5h (similar to scheme 50 illustrates an alternative method for preparing compounds of Formulas I and II, wherein X is NH, $Z^1$ is a pyrrole fused ring, $Z^2$ is a pyridine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method G. As shown, the flourine of compound 51 can be displaced by the amino group of compound 52 under suitable conditions to generate an aryl amine-linked isoquinoline 53. Similarly, an alcohol group may also be used to form compounds of Formulas I and II wherein X is O. Compound 53 may then be functionalized (not shown), for example, the nitrogen of the pyrrole ring may be alkylated using a suitable base and alkylating agent, to install desired $R^4$ substituents in the pyrrole fused ring.

Scheme 5i (Method H)

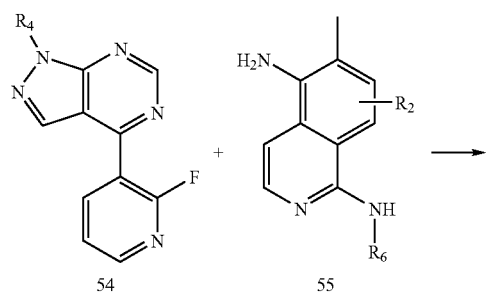

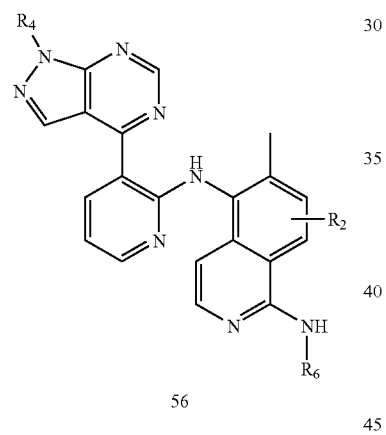

Scheme 5j (Method J)

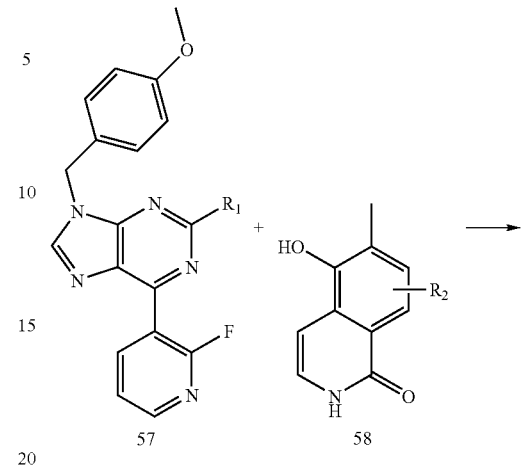

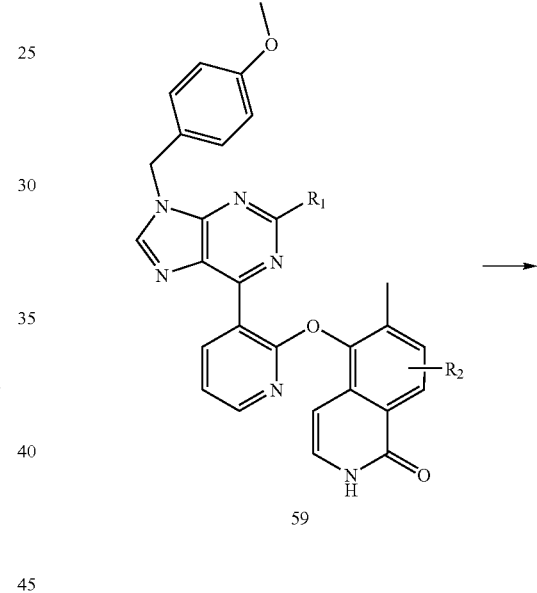

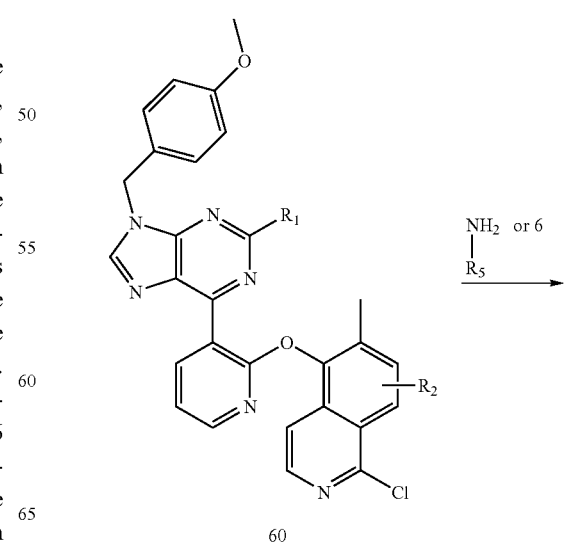

Scheme 5i (similar to scheme 5g) illustrates an alternative method for preparing compounds of Formulas I and II, wherein X is NH, $Z^1$ is a pyrazole fused ring wherein $R^4$ is H, $Z^2$ is a pyridine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method H. As shown, the flourine of compound 54 can be displaced by the amino group of compound 55 under suitable conditions to generate an aryl amine-linked isoquinoline 56. Similarly, an alcohol group may also be used to form compounds of Formulas I and II wherein X is O. Compound 56 may then be functionalized ($R^4$ group), for example, the nitrogen of the pyrazole ring may be alkylated using a suitable base and alkylating agent, to install desired $R^4$ substituents in the pyrazole fused ring.

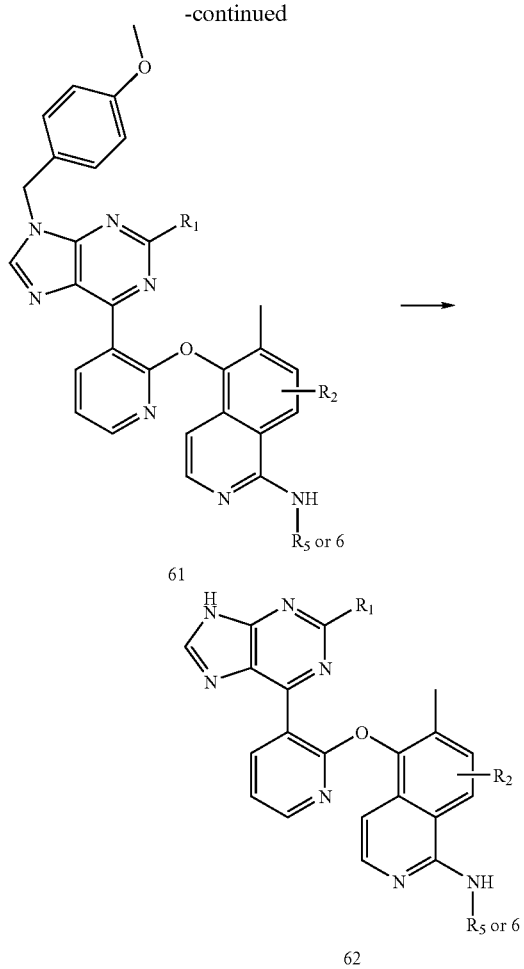

Scheme 5j illustrates an alternative method (see scheme 5g) for preparing compounds of Formulas I and II, wherein X is O, $Z^1$ is a fused imidazole ring, $Z^2$ is a pyridine ring, $A^4$ is CH (a pyridine C ring) and $R^3$ is an amino-linked ring moiety (see also schemes 2 and 3a). For the purposes of the exemplary compounds described hereinbelow, this method or general synthetic strategy is designated as Method J. As shown, the flourine of compound 57 can be displaced by the alcohol group of compound 58 under suitable conditions to generate an ether-linked adduct 59. Similarly, an amine or thiol group may also be used to form compounds of Formulas I and II wherein X is NH or S respectively (see above schemes). The carbonyl group of compound 59 can then be converted to the corresponding chloride 60 using $POCl_3$, as shown herein, and the resultant chloride compound 60 may then be displaced with a desirably substituted amine, as shown, to afford the protected imidazole-amine-linked compound 61. Compound 61 may then be deprotected to afford the desired compounds 62 of Formulas I and II. Compound 62 may then be functionalized, for example, it may be alkylated using a suitable base and alkylating agent, to install desired $R^4$ substituents in the imidazole fused ring.

While the above Schemes 1, 2a-2c, 3,3a-3d, 4, and 5a-5j (schemes 1-5j) describe methods of making compounds as shown, the strategy employed may be utilized to make compounds of Formulas I and II, as appreciated by those of ordinary skill in the art. For example, while the schemes describe methods for making a pyrazole, pyrrole or imidazole fused $Z^1$ ring and a pyridine or pyrimidine fused $Z^2$ ring compound, the methods used may also be applied to make other 5-membered and 6-membered heteroaryl fused $Z^1$ and/or $Z^2$ rings, such as those described herein. It is appreciated and understood by persons of ordinary skill in the art that certain conditions will not be universal and may not be used to make every fused $Z^1$ and/or $Z^2$ ring contemplated herein. Similarly, the methods teaching how to make the $R^2$, $R^3$ and $R^4$ groups above, may be applicable in making other $R^2$, $R^3$ and $R^4$ groups contemplated herein.

Further, while many compounds illustrated in schemes 1-5j show one $R^2$ group (methyl), similar compounds with no $R^2$ groups or compounds having more than one $R^2$ groups may also be made using similar methods.

The following analytical methods were used, unless otherwise noted, to identify the intermediates and compounds exemplified herein.

Analytical Methods:

Unless otherwise indicated, all HPLC analyses were run on a Agilent Model 1100 system with an Agilent Technologies Zorbax SB-$C_8$ (5μ) reverse phase column (4.6×150 mm; Part no. 883975-906) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods:

(A) Using a 50×100 mm column (Waters, Exterra, C18, 5μ) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 mM flow of 100% solvent B. The gradient was followed by a 2 min return to 40% solvent B .

(B) Using a 20×50 mm column at 20 mL/min. The mobile phase used was a mixture of solvent A ($H_2O$/0.1% TFA) and solvent B (ACN/0.1% TFA) with a 10 mM gradient from 5% to 100% solvent B. The gradient is followed by a 2 mM return to 5% ACN.

Proton NMR Spectra:

Unless otherwise indicated, all $^1H$ NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds

Example 1

Preparation of 6-methyl-5-nitroisoquinoline

Step 1: Preparation of 6-Methylisoquinoline

Aminoacetaldehyde dimethyl acetal (8.83 mL, 81.1 mmol) was added over 1 min to a stirred solution of p-tolualdehyde (9.88 mL, 81.1 mmol) in chloroform (150 mL) at 22° C. An exotherm was noted. The reaction was heated to reflux (65° C.) and half the solvent was removed (azeotropically to remove water). The heat was removed and the yellow solution was cooled to r.t. NMR showed the imine was formed smoothly, however, a trace of aldehyde was observed. The yellow solution was diluted with chloroform to bring the volume back to ~100 mL, cooled to −3° C. and ethyl chloroformate (7.99 mL, 81.1 mmol) was added dropwise over 5 min followed by triethyl phosphite (17.4 mL, 97.3 mmol) over 10 minutes. The clear yellow solution was then allowed to warm to RT. A reflux condenser added to reaction vessel. After 23 h, titanium tetrachloride (35.6 mL, 324 mmol) was added very slowly (strong exotherm and white fumes observed) and the reaction began to gently reflux (50° C.). Color changed from yellow to dark red to dark brown. Once addition was complete, the dark brown solution was heated to reflux (52° C.) for 10.5 h. After allowing to cool to RT overnight, the dark brown solution was poured onto ice (filled a 2 L beaker with approximately 1 L of ice), the organic layer was separated off, and the aqueous layer was washed with DCM (2×100 mL). The aqueous layer (now orange in color) was poured into a solution of potassium sodium tartrate tetrahydrate (183 g, 648 mmol) in water (300 mL), basified to pH 9 with 28-30% ammonium hydroxide (a white ppt crashed out) and then extracted with DCM (3×200 mL). The organic layer was separated, dried over sodium sulfate, filtered and the solvent was evaporated in vacuo to yield 6-methylisoquinoline (9.02 g, 78% yield) as a light tan amorphous solid. Found MS (ESI, pos. ion) m/z: 144.1 [M+H]$^+$ Step 2: Preparation of 6-Methyl-5-nitroisoquinoline 6-Methylisoquinoline (2.00 g, 14 mmol) was taken up in sulfuric acid (25.0 mL) and the mixture cooled down to 0° C. The reaction was treated with potassium nitrate (2.8 g, 28 mmol) which was added in portions. After addition was complete, the reaction was stirred for about 1.5 h at 0° C. The reaction was poured onto crushed ice and basified with 5N NaOH. The solid that precipitated was collected by suction filtration, washed with water and dried to give the product (2.5 g, 95%) as a tan solid. MS (ESI, pos. ion) m/z: 189.1 [M+H]$^+$

Example 2

Preparation of 6-methyl-5-nitroisoquinoline-N-oxide

6-Methyl-5-nitroisoquinoline (32 g, 170 mmol) was dissolved in DCM (500 mL) and cooled in an ice-acetone bath to 0° C. 3-Chloroperoxybenzoic acid (49.9 g, 289 mmol) (73%) was added in portions while stirring the reaction mixture vigorously. After the addition, the reaction mixture was stirred at 0° C. for 4 h. Upon being warmed to RT, the reaction mixture was partitioned in DCM/NaOH (aq., 1 N). After multiple extractions, the organic layers were combined and washed with brine then dried over $Na_2SO_4$. Removal of the solvent in vacuo gave 6-methyl-5-nitroisoquinoline N-oxide as a yellow solid (23 g). MS (M+H)$^+$205.

Example 3

Preparation of 1-chloro-6-methyl-5-nitroisoquinoline

Phosphorous oxychloride (2.15 mL, 23.0 mmol) was added dropwise to a solution of 6-methyl-5-nitroisoquinoline N-oxide (0.940 g, 4.60 mmol) in 1,2-dichloroethane (40.0 mL). The mixture was heated to 70° C. for 3 h to afford an off-white suspension. The mixture was concentrated and the residue was partitioned between dichloromethane and water. The aqueous phase was separated and extracted with dichloromethane. The combined organic phases were washed with saturated aqueous sodium bicarbonate solution, brine, dried over anhydrous sodium sulfate, filtered, and concentrated to afford 1-chloro-6-methyl-5-nitroisoquinoline (0.880 g, 86% yield) as an off-white solid. MS (ESI, pos. ion) m/z: 223.0 [M+H]$^+$

Example 4

Preparation of 6-methyl-5-nitroisoquinolin-1(2H)-one

1-Chloro-6-methyl-5-nitroisoquinoline (50 g, 225 mmol) was suspended in THF (500 mL, 10 mL/g) and treated with 5N aq HCl (500 mL, 10 mL/g). The suspension was stirred vigorously in a 2 L Morton Flask under a reflux condenser and heated with a heating mantle to reflux overnight (14 h). The resulting suspension was allowed to cool to RT (22° C.). The solid was removed by suction filtration and the filtrate set aside. The solid was washed with water (100 mL), $Et_2O$ (2×100 mL) and hexane (100 mL), then air-dried to afford about 40 g of a light yellow powder. The reserved filtrate was concentrated in vacuo to a volume of ~500 mL to afford a second crop of the title compound. The second crop was washed with water (100 mL), $Et_2O$ (2×100 mL) and hexane (100 mL), then air-dried to afford 4 g of an orange powder. A total of 44 g (87% yield) of the 6-methyl-5-nitroisoquinolin-1(2H)-one was isolated in this fashion. MS (ESI, pos. ion) m/z: (M+H)$^+$205.

Example 5

Preparation of 5-amino-6-methylisoquinolin-1(2H)-one

A suspension of 6-methyl-5-nitroisoquinolin-1(2H)-one (40 g, 196 mmol) in glacial acetic acid (1 L) was purged with $N_2$. The suspension was treated with 10% Pd/C (10 g) and the reaction vessel was purged with $H_2$. The mixture was stirred at RT under $H_2$ (1 atm) until starting material was consumed (approximately 100 h). The reaction mixture was purged with $N_2$, then filtered through a pad of celite. The pad was washed with MeOH (400 mL) and the combined filtrate was treated with water (80 mL) and concentrated in vacuo to ~200 mL. The dark mixture was diluted with 200 mL MeOH and added in a thin stream to ice water (1.5 L) stirred in a large beaker.

The resulting fine precipitate was collected by suction filtration. The greenish-grey powder was suspended in water (500 mL) and saturated NaHCO$_3$ (100 mL) and sonicated for 1 min. The solid was collected by suction filtration, washed with water (2×100 mL), Et$_2$O (100 mL), and air-dried overnight to afford about 28 g of a grey powder. The powder was dissolved in hot DMF (200 mL) and treated with decolorizing carbon (~10 g). The hot suspension was filtered through celite. The filter cake was washed with MeOH (200 mL) and the filtrate was concentrated in vacuo to ~200 mL. The dark brown solution was added to water (1.2 L) to afford a fine crystalline precipitate. The solid was collected by suction filtration on a medium-sintered glass frit and washed with water (500 mL). A second crop precipitated in the filtrate and was collected by suction filtration, washed with water (100 mL) and added to the first crop. The combined material was washed with Et$_2$O (400 mL), and dried on the sintered glass funnel under a stream of N$_2$, with suction, for 16 h to afford 5-amino-6-methylisoquinolin-1(2H)-one (22 g, 64% yield) as a tan crystalline solid. MS (ESI, pos. ion) m/z: 175 [M+H]$^+$ Example 6

Preparation of 5-hydroxy-6-methylisoquinolin-1(2H)-one

5-Amino-6-methylisoquinolin-1(2H)-one (2.00 g, 11.48 mmol) was dissolved in sulfuric acid (24.3 mL, 287 mmol) (75%, 35 mL). The solution was cooled to 0° C. then a solution of sodium nitrite (12.1 mmol) in sulfuric acid (5 mL) was added dropwise over 15 min. The resulting solution was stirred at 0° C. for 45 min and then the reaction mixture was heated to 70° C. and stirred for 16 h. The reaction mixture was cooled in an ice bath for 15 min, then 100 g of ice was added. The mixture was filtered. The filter cake was washed with water for 4 times until the filtrate became neutral by pH paper. The filter cake was air dried to give 5-hydroxy-6-methylisoquinolin-1(2H)-one as a dark gray solid (1.39 g, 69% yield). MS (ESI, pos. ion) m/z: 176 [M+H]$^+$ Example 7

Preparation of 1-chloro-6-methylisoquinolin-5-amine

Tin (II) chloride (0.43 g, 2.2 mmol) was added to a solution of 1-chloro-6-methyl-5-nitroisoquinoline (0.100 g, 0.45 mmol) in ethanol/DCM (10.0 mL, 4:1). The solution was heated at 70° C. for 16 h. The reaction mixture was diluted with DCM and the organic phase was washed with saturated aqueous sodium bicarbonate solution and brine, dried over anhydrous sodium sulfate, filtered, and concentrated to afford a brown solid which was purified via column chromatography on silica gel (RediSep 40 g column, gradient elution with 0-50% ethyl acetate-hexane) to afford 1-chloro-6-methylisoquinolin-5-amine (0.035 g, 40% yield) as a brown solid. MS (ESI, pos. ion) m/z: 193 [M+H]$^+$ Example 8

Preparation of 4-(6-methyl-5-nitroisoquinolin-1-ylamino)benzonitrile

A mixture of 4-aminobenzonitrile (4.0 g, 34 mmol), isopropanol (50 mL) and 1-chloro-6-methyl-5-nitroisoquinoline (5.0 g, 22 mmol) was stirred at RT (22° C.) and treated with TFA (5.0 mL, 67 mmol). The reaction mixture was stirred at 80° C. for 17 h, and allowed to cool to RT. The thick slurry was diluted with isopropanol (100 mL) and the solid precipitate was collected by suction filtration. The solid was washed with saturated NaHCO$_3$ (2×100 mL), water (50 mL), Et$_2$O (50 mL), and hexane (100 mL) and dried in a vacuum oven at 70° C. overnight to provide 4-(6-methyl-5-nitroisoquinolin-1-ylamino)benzonitrile (6.0 g, 88% yield) as a yellow solid. MS (ESI, pos. ion) m/z: 305 [M+H]$^+$.

Example 9

Preparation of 4-(5-amino-6-methylisoquinolin-1-ylamino)benzonitrile

A mixture of 4-(6-methyl-5-nitroisoquinolin-1-ylamino) benzonitrile (0.47 g, 1.5 mmol), tin(II) chloride dihydrate (1.8 g, 7.7 mmol) and absolute EtOH (50 mL) was stirred under N$_2$ at 70° C. for 17 h. The crude reaction mixture was poured onto ~100 mL ice. The resulting solution was treated with solid Na$_2$CO$_3$ to pH 10. The milky yellow suspension was extracted with EtOAc (3×150 mL). The combined EtOAc extracts were washed with saturated NaCl (100 mL), dried over Na$_2$SO$_4$, filtered and concentrated in vacuo to give 510 mg as a red solid. The crude product was adsorbed onto a plug of silica gel and chromatographed through a Redi-Sep® prepacked silica gel column (40 g), eluting with a gradient of 1% to 5% MeOH in CH$_2$Cl$_2$, to provide 4-(5-amino-6-methylisoquinolin-1-ylamino)benzonitrile (0.29 g, 68% yield) as a red solid. MS (ESI, pos. ion) m/z: 275 [M+H]$^+$.

Example 10

Preparation of 6-methyl-5-nitro-N-(3-(trifluoromethyl)phenyl)isoquinolin-1-amine 1-Chloro-6-methyl-5-nitroisoquinoline (0.25 g, 1.1 mmol) and 3-(trifluoromethyl)benzenamine (0.17 mL, 1.3 mmol) were added to a microwave tube containing 3 mL of isopropanol. The tube was capped and heated at 180° C. for 1500 seconds. The volatiles were removed in vacuo. The residue was taken up in DCM and washed with saturated NaHCO$_3$. The organic layer was dried with sodium sulfate and purified by column chromatography on silica gel using a gradient of 10 to 40% of ethyl acetate in hexanes to give the product as an orange solid (0.31 g, 79%). MS (M+H)$^+$348.

Example 11

Preparation of 6-methyl-N'-(3-(trifluoromethyl)phenyl)isoquinoline-1,5-diamine

6-Methyl-5-nitro-N-(3-(trifluoromethyl)phenyl)isoquinolin-1-amine (0.28 g, 0.81 mmol) was dissolved in ethanol (20 mL) and 10% palladium on carbon (0.086 g, 0.81 mmol) was added to the solution. The reaction stirred overnight at RT under a hydrogen atmosphere. The reaction was filtered through celite and concentrated to give the title compound as a pink film (0.25 g, 98%). MS (M+H)$^+$318.

Example 12

Preparation of 7-methylquinazolin-4(3H)-one

A mixture of 2-amino-4-methylbenzamide (20 g, 133 mmol) and formic acid (120 ml, 3129 mmol) was heated to 100° C. for 6 h. The reaction was cooled to RT and the volatiles were removed under reduced pressure. The residue was then washed carefully with aqueous saturated sodium bicarbonate and then with water. The tan solid was then dried in a vacuum oven at 45° C. overnight to give 7-methylquinazolin-4(3H)-one (18.00 g, 84% yield). MS (ESI, pos. ion) m/z: 161 [M+H]+

Example 13

Preparation of 6-bromo-7-methylquinazolin-4(3H)-one 7-methylquinazolin-4(3H)-one (14.56 g, 91 mmol) was added to methanol (70 ml, 91 mmol) and glacial acetic acid (70 ml, 1212 mmol). The mixture was stirred at RT for 5 min followed by the slow addition of bromine (9.3 mL, 182 mmol). The reaction was stirred at RT for 3 h. Volatiles were evaporated under reduced pressure and the resulting crude residue washed with aqueous sodium thiosulfate to remove excess bromine and HBr, then oven dried to give 6-bromo-7-methylquinazolin-4(3H)-one (18.35 g, 84% yield) as light yellow amorphous solid. MS (ESI, pos. ion) m/z: 239 [M+H]+

Example 14

Preparation of 6-bromo-7-methyl-8-nitroquinazolin-4(3H)-one

6-Bromo-7-methylquinazolin-4(3H)-one (1.0 g, 4.2 mmol) was added to $H_2SO_4$ (98%, 15 mL) and the mixture was stirred at it until dissolution was complete. The mixture was cooled to 0° C. and then nitric acid (fuming) (0.26 g, 4.2 mmol) was added dropwise at 0° C. and stirred for 10 min, and then stirred at it for 5 h. The mixture was poured onto ice (300 g) and extracted with EtOAc (3×80 mL). The combined organic layers were washed with brine (100 mL), dried over $MgSO_4$ and concentrated in vacuo. The product was recrystallized from MeOH (~15 mL). MS (ESI, pos. ion) m/z: 284 [M+H]+

Example 15

Preparation of 6-bromo-4-chloro-7-methyl-8-nitroquinazoline

A mixture of phosphorous oxychloride (5 mL) and 6-bromo-7-methyl-8-nitroquinazolin-4(3H)-one (800 mg, 2.82 mmol) was refluxed at 130° C. for 4 h. On cooling, $POCl_3$ was removed under reduced pressure. The resulting crude product residue was diluted with ice-water and extracted out of the aqueous layer with DCM (3×20 mL). The combined organic extracts were dried over anhydrous sodium sulfate and concentrated to give 6-bromo-4-chloro-7-methyl-8-nitroquinazoline (595 mg, 70% yield) as an amorphous light yellow solid. MS (ESI, pos. ion) m/z: 302 [M+H]+

Example 16

Preparation of 4-(6-bromo-7-methyl-8-nitroquinazolin-4-ylamino)benzonitrile

A mixture of 6-bromo-4-chloro-7-methyl-8-nitroquinazoline (211 mg, 0.70 mmol) and 4-aminobenzonitrile (208 mg, 1.76 mmol) in toluene (25 mL) was refluxed overnight. i-PrOH (25 mL) was added and the mixture was refluxed for 5 h. After cooling to rt the precipitate was filtered and washed with i-PrOH to give 4-(6-bromo-7-methyl-8-nitroquinazolin-4-ylamino)benzonitrile (195 mg, 72%). MS (ESI, pos. ion) m/z: 384 [M+H]+

Example 17

Preparation of 4-(8-amino-7-methylquinazolin-4-ylamino)benzonitrile

A mixture of 4-(6-bromo-7-methyl-8-nitroquinazolin-4-ylamino)benzonitrile (400 mg, 1.04 mmol) and Pd/C (10%~30 mg) in EtOH (20 mL) was stirred under $H_2$ gas (1 atm) overnight. 30 mL of $NH_3$/MeOH (2 M) was added and the mixture was filtered through celite and washed with MeOH/DCM (~1:1). After removal of solvent the product was purified by flash chromatography eluting with MeOH/DCM (1-5%) to give 4-(8-amino-7-methylquinazolin-4-ylamino)benzonitrile (238 mg, 83%). MS (ESI, pos. ion) m/z: 276 [M+H]+

Example 18

Preparation of 4-(2-fluoropyridin-3-yl)-7H-pyrrolo[2,3-d]pyrimidine

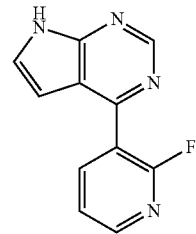 [SMILES: Fc1ncccc1-c1ncnc2[nH]ccc12]

A mixture of 4-chloro-7H-pyrrolo[2,3-d]pyrimidine (7.68 g, 50 mmol), 2-fluoropyridin-3-ylboronic acid (10.57 g, 75 mmol), and tetrakis(triphenylphosphine)palladium(0) (2.89 g, 2.5 mmol) was suspended in DME (300 mL) and aqueous sodium carbonate (10%) (50 mL, 100 mmol). The suspension was heated at reflux over night, cooled to r.t. and the reaction mixture was partitioned between EtOAc (300 mL) and $NaHCO_3$ (aq., sat., 200 mL). The aqueous layer was washed with EtOAc twice. The organic layers were combined and washed with brine, then loaded on silica and purified via flash column (EtOAc:hexane=50-95%) on ISCO to give 4-(2-fluoropyridin-3-yl)-7H-pyrrolo[2,3-d]pyrimidine as a light yellow solid with a green tint (1.85 g, 17% yield). MS (ESI, pos. ion) m/z: 214 [M+H]+

Example 19

Preparation of 4-(2,4-di-tert-butoxypyrimidin-5-yl)-7H-pyrrolo[2,3-d]pyrimidine 2,4-Di-tert-butoxypyrimidin-5-ylboronic acid (17.5 g, 65.4 mmol), tetrakis(triphenylphosphine) palladium(0) (7.6 g, 6.54 mmol) and sodium carbonate (20.8 g, 196 mmol) were added to a solution of 4-chloro-7H-pyrrolo[2,3-d]pyrimidine (10 g, 65.4 mmol) in DME (400 mL) and water (150 mL). With vigorous stirring, the mixture was heated to 80° C. for 24 h. The reaction mixture was cooled to RT and poured into water (100 mL). The mixture was extracted with EtOAc (100 mL) twice. The combined organic layers were washed with brine, dried over $Na_2SO_4$, and concentrated to give the crude product. This was purified by flash chromatography to give 4-(2,4-di-tert-butoxypyrimidin-5-yl)-7H-pyrrolo[2,3-d]pyrimidine (16.0 g, 72%) as a yellow solid. MS (APCI, pos. ion) m/z: 342.1 [M+H]+

Example 20

Preparation of 4-(2,4-dichloropyrimidin-5-yl)-7H-pyrrolo[2,3-d]pyrimidine

POCl₃ (22.3 g, 147 mmol) and DIEA (9.5 g, 73.5 mmol) were added to a solution of 4-(2,4-di-tert-butoxypyrimidin-5-yl)-7H-pyrrolo[2,3-d]pyrimidine (5.0 g, 14.7 mmol) in DCE (200 mL). The mixture was heated at 80° C. for 4 h. The reaction mixture was cooled to RT and poured onto ice-NaHCO₃ (aq). The mixture was extracted with ethyl acetate (2×100 mL) and the combined organic layers were washed with brine, dried over Na₂SO₄, and concentrated. The crude product was purified by flash chromatography to give 4-(2,4-dichloropyrimidin-5-yl)-7H-pyrrolo[2,3-d]pyrimidine (550 mg, 14%) as white solid. MS (APCI, pos. ion) m/z: 266 [M+H]+

Example 21

Preparation of 6-chloro-9-(tetrahydro-2H-pyran-2-yl)-9H-purine

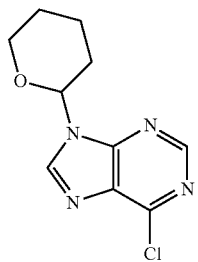 [SMILES: Clc1ncnc2c1ncn2C1CCCCO1]

A suspension of 6-chloro-9H-purine (25.36 g, 164 mmol) and 4-methylbenzenesulfonic acid (0.565 g, 3.28 mmol) in EtOAc (250 mL) was treated with 3,4-dihydro-2H-pyran (44.9 mL, 492 mmol). The mixture was heated at 90° C. and the solid slowly dissolved over 1 h. The flask was removed from the oil bath and the cloudy, yellow solution was filtered and concentrated in vacuo. The pale yellow residue was dissolved in DCM and purified by flash chromatography (50% EtOAc/hexane) (1 L silica/4 L solvent) to give 6-chloro-9-(tetrahydro-2H-pyran-2-yl)-9H-purine (38.90 g, 99.3% yield) as a colorless oil which slowly crystallized. MS (ESI, pos. ion) m/z: 239.1 [M+H]+

Example 22

Preparation of 6-(2-fluoropyridin-3-yl)-9-(tetrahydro-2H-pyran-2-yl)-9H-purine

A solution of 6-chloro-9-(tetrahydro-2H-pyran-2-yl)-9H-purine (6.00 g, 25.1 mmol) in dioxane (54 mL) was sequentially treated with water (7.2 mL), 2-fluoropyridin-3-ylboronic acid (5.31 g, 37.7 mmol), sodium carbonate monohydrate (9.35 g, 75.4 mmol) and PdCl₂(dppf) (0.616 g, 0.754 mmol). The stirred mixture was degassed (alternating vacuum/nitrogen) and heated under nitrogen at 100° C. for 10 h. The mixture was cooled and extracted into EtOAc (500 mL) from water (400 mL). The aqueous layer was extracted with EtOAc (200 mL) and the combined organic extracts were dried (MgSO₄), filtered through celite, and concentrated. The crude product was dissolved in a small volume of DCM and purified by flash chromatography (50%→75%→100% EtOAc/hexane) to give 6-(2-fluoropyridin-3-yl)-9-(tetrahydro-2H-pyran-2-yl)-9H-purine (3.96 g, 53% yield) as an off-white solid. MS (ESI, pos. ion) m/z: 300.1 [M+H]+

Example 23

Preparation of 9-(4-methoxybenzyl)-6-bromo-9H-purine

A suspension of 6-bromo-9H-purine (4.3 g, 22 mmol) in anhydrous DMF (40 mL) was treated with potassium carbonate (9.0 g, 65 mmol) and stirred for 20 min at room temperature (22° C.). The mixture was treated with 4-methoxybenzyl chloride (5.9 mL, 43 mmol) and allowed to stir for 20 h at 45° C. The solids were removed by suction filtration and the solvent removed in vacuo. The resulting crude oil was partitioned between water and 3:1 CHCl₃:IPA (100 mL each). The aqueous layer was extracted with 3:1 CHCl₃:IPA (100 mL). The combined organic extract was washed with saturated NaCl (70 mL), dried over Na₂SO₄, filtered, and concentrated in vacuo to a viscous oil. The crude product was chromatographed through a Redi-Sep® pre-packed silica gel column (330 g), eluting with a gradient of 40% to 70% EtOAc in hexane, to provide 9-(4-methoxybenzyl)-6-bromo-9H-purine (2.7 g, 39% yield) as a white waxy solid; ¹H NMR (400 MHz, DMSO-d₆) □ ppm 3.71 (s, 3H), 5.44 (d, J=4.02 Hz, 2H), 6.90 (d, J=8.03 Hz, 2H), 7.34 (d, J=8.53 Hz, 2H), 8.76 (d, J=22.59 Hz, 1H), 8.81 (s, 1H).

Example 24

Preparation of 9-(4-methoxybenzyl)-6-(2-fluoropyridin-3-yl)-9H-purine

A mixture of 9-(4-Methoxybenzyl)-6-bromo-9H-purine (2.7 g, 8.5 mmol), 2-fluoropyridin-3-ylboronic acid (1.8 g, 13 mmol) and potassium acetate (2.5 g, 25 mmol) in 1-butanol (50 mL) and water (10 mL) was purged with Ar (vacuum/purge three times) to remove oxygen, then PdCl₂(P^tBu₂Ph)₂ (0.063 g, 0.10 mmol) was added. The reaction mixture was stirred in a 100° C. oil bath for 45 min. The reaction mixture was allowed to cool to RT and diluted with Et₂O (300 mL). The mixture was washed with water (2×100 mL), brine (50 mL), dried over Na₂SO₄, and filtered. Some product precipitated before the filtration so the Na₂SO₄ was washed with 3:1 CHCl₃:IPA to dissolve all product. The combined filtrate was concentrated in vacuo to ~50 mL as a suspension. The suspension was diluted with Et₂O (200 mL) and hexane (200 mL) and the solid collected by suction filtration. The solid was washed with hexane (50 mL) and dried under a stream of N₂ with vacuum suction for 14 h to afford 2.39 g (crop 1) as a pale orange fine crystalline solid. The mother liquors were concentrated in vacuo to ~100 mL to afford a second crop of product. The second crop was collected by suction filtration, washed with hexane (100 mL) and dried under a stream of N₂ as above to provide 200 mg (crop 2) as a pale orange fine crystalline solid. MS (ESI, pos. ion) m/z: 336.1 [M+H]+.

Example 25

Preparation of 4-(2-fluoropyridin-3-yl)-5H-pyrrolo[3,2-d]pyrimidine

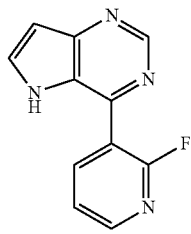 [SMILES: Fc1ncccc1-c1ncnc2cc[nH]c12]

A mixture of 4-chloro-5H-pyrrolo[3,2-d]pyrimidine (0.500 g, 3.26 mmol), 2-fluoropyridin-3-ylboronic acid (0.688 g, 4.88 mmol) and potassium acetate (0.959 g, 9.77 mmol) in 1-butanol (25 mL) and water (5 mL) was purged with Ar (vacuum/purge three times) to remove oxygen, then PdCl$_2$Cl$_2$(P$^t$Bu$_2$Ph)$_2$ (0.0243 g, 0.0391 mmol) was added. The reaction mixture was stirred in a 100° C. oil bath for 60 min. The brown solution was concentrated in vacuo to a solid residue. The residue was treated with 3:1 CHCl$_3$:IPA (100 mL) and water (70 mL). The mixture was sonicated and the layers separated. The aqueous phase was extracted with 3:1 CHCl$_3$:IPA (50 mL). The combined organic extracts were washed with water (3×70 mL), brine (50 mL), dried over Na$_2$SO$_4$, filtered and concentrated in vacuo to give 0.74 g crude product as a yellow solid. The crude product was adsorbed onto a plug of silica gel and chromatographed through a Redi-Sep® pre-packed silica gel column (80 g), eluting with a gradient of 80% to 100% EtOAc in CH$_2$Cl$_2$, to provide 4-(2-fluoropyridin-3-yl)-5H-pyrrolo[3,2-d]pyrimidine (0.51 g, 73% yield) as a pale yellow solid. MS (ESI, pos. ion) m/z: 215 [M+H]+.

Example 26

Preparation of 4-chloro-4H-pyrazolo[3,4-d]pyrimidine

Hydrazine hydrate (2.0 ml, 41 mmol) was slowly added to a solution of 4,6-dichloropyrimidine-5-carbaldehyde (7.2 g, 41 mmol) in MeOH (150 ml)-60° C. (nitromethane-dry ice bath) followed by triethylamine (6.8 mL, 49 mmol). The mixture was allowed to warm to rt and stirred for 2 h. MeOH was removed in vacuo and water (150 mL) was added. The mixture was extracted with EtOAc (3×80 mL). The combined organic layers were washed with brine (100 mL), dried over Na$_2$SO$_4$, and filtered through a glass funnel. Removal of solvent gave 4-chloro-1H-pyrazolo[3,4-d]pyrimidine (4.45 g, 71%). MS (ESI, pos. ion) m/z: 155 [M+H]+

Example 27

Preparation of 4-(2-fluoropyridin-3-yl)-1H-pyrazolo[3,4-d]pyrimidine

A degassed mixture of potassium acetate (1.9 g, 19 mmol), PdCl$_2$(P$^t$Bu$_2$Ph)$_2$ (0.16 g, 0.26 mmol), 4-chloro-1H-pyrazolo[3,4-d]pyrimidine (1.00 g, 6.5 mmol) and 2-fluoropyridin-3-ylboronic acid (1.1 g, 7.8 mmol) in EtOH (30 mL)-water (10 mL) was sonicated until the solid became a fine powder. The mixture was refluxed under N$_2$ overnight. After cooling to rt, solvent was removed in vacuo and water (50 mL) and NaHCO3 (sat. 100 mL) were added to the residue. The mixture was extracted with EtOAc (3×100 mL). The solid was filtered and washed with water. The combined organic layers were washed with brine (50 mL), dried over MgSO$_4$, filtered through celite and concentrated in vacuo to give 4-(2-fluoropyridin-3-yl)-1H-pyrazolo[3,4-d]pyrimidine (0.56 g). The previous solid was dissolved in MeOH-DCM and preloaded on silica gel and purified by flash column chromatography eluting with MeOH/DCM (1-5%) to give give 4-(2-fluoropyridin-3-yl)-1H-pyrazolo[3,4-d]pyrimidine (3.4 g). The two product crops were combined (65% overall). MS (ESI, pos. ion) m/z: 216 [M+H]+

Example 28

Preparation of 5-(3-(7H-pyrrolo[2,3-d]pyrimidin-4-yl)pyridin-2-ylamino)-6-methylisoquinolin-1(2H)-one

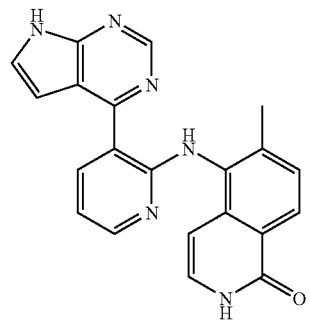 [SMILES: Cc1ccc2c(=O)[nH]ccc2c1Nc1ncccc1-c1ncnc2[nH]ccc12]

A mixture of 4-(2-fluoropyridin-3-yl)-7H-pyrrolo[2,3-d]pyrimidine (463 mg, 2162 µmol) and 5-amino-6-methylisoquinolin-1(2H)-one (377 mg, 2162 µmol) in THF (1.5 mL) was sonicated for 5 min until all the solid was mixed well. Lithium bis(trimethylsilyl)amide (9.7 mL, 9.72 mmol; 1 M in THF) was added via a syringe and the reaction tube was sonicated and stirred at RT for 5 min. The reaction was heated to 120° C. in a microwave for 20 min. The reaction mixture was cooled to rt and partitioned between DCM and NaHCO$_3$. The aqueous layer was washed with DCM three times. The combined organic layers were washed with brine and dried over Na$_2$SO$_4$, then concentrated in vacuo. The residue was purified via flash column on silica (MeOH-DCM=0.5-6%) to give a light brown solid 5-(3-(7H-pyrrolo[2,3-d]pyrimidin-4-yl)pyridin-2-ylamino)-6-methylisoquinolin-1(2H)-one (550 mg, 69% yield). MS (ESI, pos. ion) m/z: 369

Example 29

Preparation of N-(3-(7H-pyrrolo[2,3-d]pyrimidin-4-yl)pyridin-2-yl)-1-chloro-6-methylisoquinolin-5-amine Method 1:
5-(3-(7H-Pyrrolo[2,3-d]pyrimidin-4-yl)pyridin-2-ylamino)-6-methylisoquinolin-1(2H)-one (750 mg, 2036 µmol) was suspended in phosphorous oxychloride (9.5 mL, 10.2 mmol). The reaction vessel was flushed with $N_2$ and sealed. The reaction was heated in an oil bath for 5 h. The excess reagent was removed in vacuo. The residue was azeotroped with toluene times and then put under high vacuum overnight. The residue was suspended with 50 g of ice. The suspension was neutralized with $NaHCO_3$ (aq., sat.). The resulting mixture was extracted with DCM. The DCM solution was concentrated in vacuo and the residue was purified via flash column on silica (Hexane:EtOAc gradient of 50-10%) to give N-(3-(7H-pyrrolo[2,3-d]pyrimidin-4-yl)pyridin-2-yl)-1-chloro-6-methylisoquinolin-5-amine as a yellow solid (530 mg, 67% yield). MS (ESI, pos. ion) m/z: 387 [M+H]$^+$ Alternatively, the title compound was made by a second method, below.
Method 2:
A mixture of 4-(2-fluoropyridin-3-yl)-7H-pyrrolo[2,3-d]pyrimidine (2.17 g, 10.1 mmol) and 1-chloro-6-methylisoquinolin-5-amine (1.95 g, 10.1 mmol) in THF (4 mL) was sonicated for 3 min until throughly mixed. Lithium bis(trimethylsilyl)amide (7.63 g, 45.6 mmol) (1 N in THF from Aldrich) was added in a stream and the resulting dark brown solution was stirred at 22° C. for 4 h. The reaction was quenched with $NaHCO_3$ (aq., sat.) while cooled in an ice bath. The reaction mixture was then partitioned between EtOAc and $NaHCO_3$ (aq., sat). The aqueous layer was washed with EtOAc twice. The organic layers were combined and concentrated in vacuo. The light brown solid residue was triturated with EtOAc (~50 mL) to give a yellow solid. This solid was collected by filtration and washed with EtOAc twice and then dried in a vacuum oven (45° C.) over the weekend to give N-(3-(7H-pyrrolo[2,3-d]pyrimidin-4-yl)pyridin-2-yl)-1-chloro-6-methylisoquinolin-5-amine as a yellow solid (2.85 g, 73% yield). MS (ESI, pos. ion) m/z: 387 [M+H]$^+$

Example 30

Via Method A

Preparation of 4-(5-(3-(7H-pyrrolo[2,3-d]pyrimidin-4-yl)pyridin-2-ylamino)-6-methylisoquinolin-1-ylamino)benzonitrile A mixture of 4-aminobenzonitrile (35 mg, 299 mmol), N-(3-(7H-pyrrolo[2,3-d]pyrimidin-4-yl)pyridin-2-yl)-1-chloro-6-methylisoquinolin-5-amine (110 mg, 284 µmol), tris(dibenzylideneacetone)dipalladium(0) (10 mg, 11 µmol), and 2-dicyclohexylphosphino-2'-(N,N-dimethylamino)biphenyl (9 mg, 23 µmol) were suspended in THF (1 mL) and sealed. The mixture was sonicated until homogeneously mixed. Lithium bis(trimethylsilyl)amide (1.28 mL, 1280 mmol) was then added through a syringe, then mixed well with sonication. The reaction tube was heated via microwave to 120° C. for 15 min. The reaction mixture was cooled to room temperature, then partitioned between EtOAc (3×50 mL) and NaHCO3 (aq., sat). The organic layer was washed with brine, and extracted with HCl (aq., 1 N, 3×50 mL). The aqueous layers were combined and filtered through a layer of celite. The filter cake was rinsed with 1 N HCl. The filtrate was then cooled in ice and neutralized with $NH_4OH$ (aq., conc.) to pH 8, then extracted with EtOAc (4×50 mL). The organic layers were combined, washed with brine, dried over $Na_2SO_4$, and then concentrated to give a brown solid which was then triturated with MeOH to give a light brown solid upon filtration. The filter cake was air dried over the weekend to give 4-(5-(3-(7H-pyrrolo[2,3-d]pyrimidin-4-yl)pyridin-2-ylamino)-6-methylisoquinolin-1-ylamino)benzonitrile. MS (ESI, pos. ion) m/z: 469.2

Example 31

Via Method B

Preparation of N5-(2-chloro-5-(7H-pyrrolo[2,3-d]pyrimidin-4-yl)pyrimidin-4-yl)-6-methyl-N1-(2-methyl-5-(trifluoromethyl)phenyl)isoquinoline-1,5-diamine

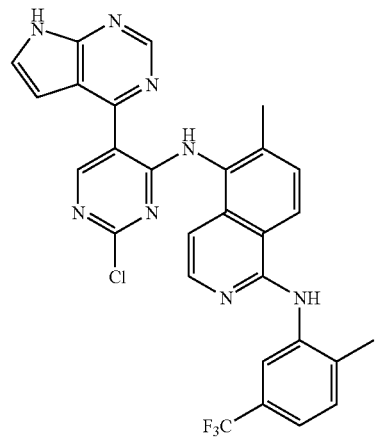 [SMILES: Cc1ccc(C(F)(F)F)cc1Nc1nccc2c(Nc3nc(Cl)ncc3-c3ncnc4[nH]ccc34)c(C)ccc12]

A mixture of 4-(2,4-dichloropyrimidin-5-yl)-7H-pyrrolo[2,3-d]pyrimidine (89 mg, 335 µmol) and 6-methyl-N1-(2-methyl-5-(trifluoromethyl)phenyl)isoquinoline-1,5-diamine (111 mg, 335 µmol) in DMSO (2 mL) was treated with DIPEA (0.3 mL). The mixture was heated to 70° C. in an oil bath for 2 days. Additional quantities of 4-(2,4-dichloropyrimidin-5-yl)-7H-pyrrolo[2,3-d]pyrimidine (3×20 mg) were added during the course of the reaction. The reaction mixture was cooled to rt and poured onto 50 g of ice with 20 mL of $NaHCO_3$. The resulting suspension was extracted with EtOAc (3×50 mL). The EtOAc solution was washed with brine then dried over $Na_2SO_4$ and concentrated. The residue was purified via prep LCMS on silica [4% 1M NH3-MeOH in DCM-EtOAc (5-1)]. The residue was further purified by trituation in MeOH to give the title compound as a light yellow solid. MS (ESI, pos. ion) m/z: 561.2 [M+H]$^+$

Example 32

Via Method C

Preparation of 4-(5-(3-(9-(4-methoxybenzyl)-9H-purin-6-yl)pyridin-2-ylamino)-6-methylisoquinolin-1-ylamino)benzonitrile A mixture of 4-(5-amino-6-methylisoquinolin-1-ylamino)benzonitrile (0.250 g, 0.91 mmol) and 9-(4-methoxybenzyl)-

6-(2-fluoropyridin-3-yl)-9H-purine (0.34 g, 1.0 mmol) in anhydrous THF (20 mL) was treated dropwise with lithium bis(trimethylsilyl)amide (1.0 M solution in THF; 2.7 mlL, 2.7 mmol) to give a dark suspension. The suspension was sonicated for 2 min and then stirred at RT for 30 min. The reaction mixture was sonicated again for 2 min. The mixture was treated with 1N aq HCl (5 mL) and stirred at RT for 10 min. The reaction mixture was added to satd NaHCO₃ (70 mL) and extracted with 3:1 CHCl₃:IPA (3×50 mL). The combined organic layers were washed with satd NaCl, dried over Na₂SO₄, filtered, and concentrated in vacuo to give 840 mg crude product. The crude product was adsorbed onto a plug of silica gel and chromatographed through a Redi-Sep® pre-packed silica gel column (80 g), eluting with a gradient of 10% to 50% EtOAc in CH₂Cl₂, to give 4-(5-(3-(9-(4-methoxybenzyl)-9H-purin-6-yl)pyridin-2-ylamino)-6-methylisoquinolin-1-ylamino)benzonitrile. MS (ESI, pos. ion) m/z: 590.2 [M+H]⁺

Example 33

Via Method D

Preparation of 4-(5-(3-(9H-purin-6-yl)pyridin-2-ylamino)-6-methylisoquinolin-1-ylamino)benzonitrile

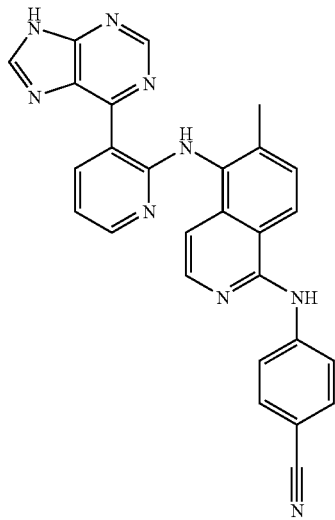 [SMILES: Cc1ccc2c(Nc3ccc(C#N)cc3)nccc2c1Nc1ncccc1-c1ncnc2[nH]cnc12]

A solution of 4-(5-(3-(9-(4-methoxybenzyl)-9H-purin-6-yl)pyridin-2-ylamino)-6-methylisoquinolin-1-ylamino)benzonitrile (0.37 g, 0.63 mmol) in TFA (3 mL) was stirred in a 65° C. oil bath for 4.5 h. The reaction mixture was concentrated to give a dark orange residue. The residue was dissolved in MeCN (4 mL) and added dropwise to 1 N HCl in Et₂O (100 mL). The resulting precipitate was collected by suction filtration. The bright yellow solid was dissolved in MeOH (50 mL) and 2M NH₃ in MeOH (50 mL) and adsorbed onto a pad of silica gel. The crude product was chromatographed through a Redi-Sep® pre-packed silica gel column (12 g), eluting with a gradient of 1% to 10% 1 M NH₃.MeOH in CH₂Cl₂ (over 30 min), to provide 4-(5-(3-(9H-purin-6-yl)pyridin-2-ylamino)-6-methylisoquinolin-1-ylamino)benzonitrile (0.128 g, 43% yield). The orange solid was suspended in MeOH (5 mL), Et₂O (100 mL), and hexane (100 mL), and stirred at reflux for 2 h. The solid was collected by suction filtration, washed with hexane and dried in vacuo at 80° C. overnight to give 4-(5-(3-(9H-purin-6-yl)pyridin-2-ylamino)-6-methylisoquinolin-1-ylamino)benzonitrile as an amorphous orange solid. ¹H NMR (400 MHz, DMSO-d₆) □ ppm 2.38 (s, 3H), 6.91 (dd, J=7.78, 4.77 Hz, 1H), 7.28 (d, J=5.52 Hz, 1H), 7.66 (d, J=8.53 Hz, 1H), 7.75 (d, J=8.53 Hz, 2H), 8.01 (d, J=5.52 Hz, 1H), 8.03-8.07 (m, 1H), 8.13 (d, J=8.53 Hz, 2H), 8.42 (d, J=9.03 Hz, 1H), 8.74 (s, 1H), 9.06 (s, 1H), 9.66 (s, 1H), 9.71-9.85 (m, 1H), 11.87 (s, 1H), 13.84 (s, 1H).

Example 34

Via Method E

Preparation of 4-(8-(3-(7H-pyrrolo[2,3-d]pyrimidin-4-yl)pyridin-2-ylamino)-7-methylquinazolin-4-ylamino)benzonitrile

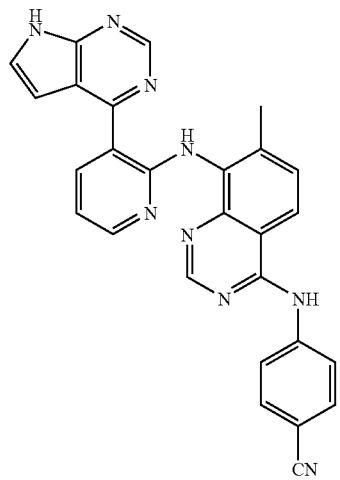 [SMILES: Cc1ccc2c(Nc3ccc(C#N)cc3)ncnc2c1Nc1ncccc1-c1ncnc2[nH]ccc12]

A mixture of 4-(2-fluoropyridin-3-yl)-7H-pyrrolo[2,3-d]pyrimidine (78 mg, 363 μmol) and 4-(8-amino-7-methylquinazolin-4-ylamino)benzonitrile (100 mg, 363 μmol) in THF (4 mL) was sonicated until all solids became a fine powder. Lithium bis(trimethylsilyl)amide (1.0 M solution in tetrahydrofuran; 1.64 mL, 1.64 mmol) was then added dropwise with stirring (all solids dissolved and then some solid appeared again). The mixture was stirred at rt for 10 min and then heated in a microwave at 120° C. for 30 min. The mixture was poured into MeOH (10 mL) and AcOH (0.5 mL) and stirred for 10 min, then 2 M NH₃ in MeOH (20 mL) was added. Solvent was removed under vacuum and the residue was purified by flash chromatography eluting with MeOH (NH₃)/DCM to give 4-(8-(3-(7H-pyrrolo[2,3-d]pyrimidin-4-yl)pyridin-2-ylamino)-7-methylquinazolin-4-ylamino)benzonitrile. MS (ESI, pos. ion) m/z: 470.2 [M+H]⁺

Example 35

Via Method F

Preparation of 4-(8-(3-(9-(4-methoxybenzyl)-9H-purin-6-yl)pyridin-2-ylamino)-7-methylquinazolin-4-ylamino)benzonitrile A mixture of 9-(4-methoxybenzyl)-6-(2-fluoropyridin-3-yl)-9H-purine (146 mg, 436 μmol) and 4-(8-amino-7-methylquinazolin-4-ylamino)benzonitrile (120 mg, 436 μmol) in THF (4 mL) was sonicated until all solids became a fine powder. Lithium bis(trimethylsilyl)amide (1.0 M solution in THF; 1.53 mL, 1.53 mmol) was added dropwise with stirring (all solids dissolved and then some solid appeared again). The mixture was stirred at rt for 10 min and then heated in a microwave at 140° C. for 30 min. The mixture was poured into AcOH (0.5 mL) in MeOH (20 mL) and the mixture was stirred for 10 min. Solvent was removed and the product was purified by flash chromatography eluting with MeOH/DCM (2-5%) to give 4-(8-(3-(9-(4-methoxybenzyl)-9H-purin-6-yl)pyridin-2-ylamino)-7-methylquinazolin-4-ylamino)benzonitrile. MS (ESI, pos. ion) m/z: 591.2 [M+H]⁺

Example 36

Via Method F

Preparation of 4-(8-(3-(9H-purin-6-yl)pyridin-2-ylamino)-7-methylquinazolin-4-ylamino)benzonitrile

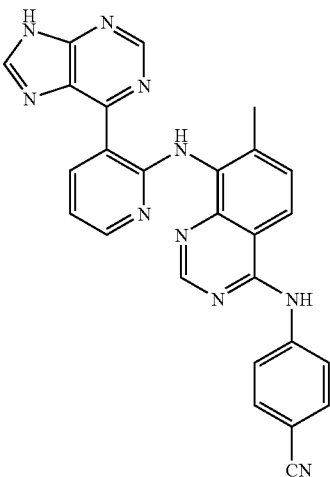

A mixture of 4-(8-(3-(9-(4-methoxybenzyl)-9H-purin-6-yl)pyridin-2-ylamino)-7-methylquinazolin-4-ylamino)benzonitrile (91 mg, 154 µmol) in TFA (3 mL) was heated at 70° C. for 3 h. The TFA was removed in vacuo and 2M NH₃/MeOH was added. The mixture was stirred for 5 min and solvent was removed in vacuo. The product was purified by flash chromatography eluting with MeOH(NH₃)/DCM (2-6%) to give 4-(8-(3-(9H-purin-6-yl)pyridin-2-ylamino)-7-methylquinazolin-4-ylamino)benzonitrile. MS (ESI, pos. ion) m/z: 471.2 [M+H]⁺

Example 37

Via Method G

Preparation of 4-(5-(3-(5H-pyrrolo[3,2-d]pyrimidin-4-yl)pyridin-2-ylamino)-6-methylisoquinolin-1-ylamino)benzonitrile

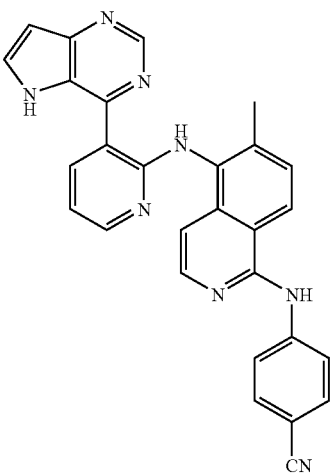 [SMILES: Cc1ccc2c(Nc3ccc(C#N)cc3)nccc2c1Nc1ncccc1-c1ncnc2cc[nH]c12]

A mixture of 4-(5-amino-6-methylisoquinolin-1-ylamino)benzonitrile (0.150 g, 0.55 mmol) and 4-(2-fluoropyridin-3-yl)-5H-pyrrolo[3,2-d]pyrimidine (0.13 g, 0.60 mmol) in anhydrous THF (10 mL) was stirred at RT and treated dropwise with lithium bis(trimethylsilyl)amide (1.0 M solution in THF; 1.7 mL, 1.7 mmol) to give a dark suspension. After 1 h stirring, the mixture was treated with 1 N aq HCl (10 mL) and stirred at RT for 10 min. The reaction mixture was added to satd NaHCO₃ (70 mL) and extracted with 3:1 CHCl₃IPA (3×70 mL). The combined organic layers were washed with satd NaCl (50 mL), dried over Na₂SO₄, filtered, and concentrated in vacuo. The crude product was adsorbed onto a plug of silica gel and chromatographed through a Redi-Sep® prepacked silica gel column (40 g), eluting with a gradient of 70% to 90% EtOAc in CH₂Cl₂ to provide 50 mg. The crude product was purified by reverse-phase preparative HPLC using a Phenomenex Gemini column, 10 micron, C18, 110 Å, 150×30 mm, 0.1% TFA in CH₃CN/H₂O, gradient 10% to 100% over 13 min. Fractions containing product were combined, concentrated in vacuo, and lyophilized to give 4-(5-(3-(5H-pyrrolo[3,2-d]pyrimidin-4-yl)pyridin-2-ylamino)-6-methylisoquinolin-1-ylamino)benzonitrile as a bright yellow solid. MS (ESI, pos. ion) m/z: 469.2 [M+H]⁺

Example 38

Via Method H

Preparation of N5-(3-(1H-pyrazolo[3,4-d]pyrimidin-4-yl)pyridin-2-yl)-6-methyl-N-1-(3-(trifluoromethyl)phenyl)isoquinoline-1,5-diamine

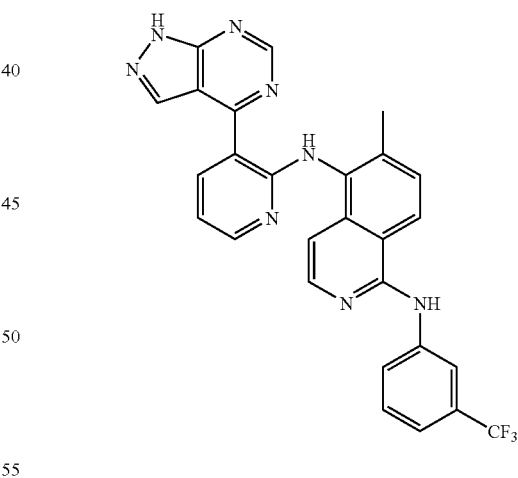

A mixture of 4-(2-fluoropyridin-3-yl)-1H-pyrazolo[3,4-d]pyrimidine (30 mg, 139 µmol) and 6-methyl-N1-(3-(trifluoromethyl)phenyl)isoquinoline-1,5-diamine (49 mg, 153 µmol) in THF (3 mL) was treated with lithium bis(trimethylsilyl)amide (1.0 M solution in THF; 627 µL, 627 µmol). The mixture was stirred at it for 3 h and then heated in a microwave at 100° C. for 20 min. The mixture was poured into MeOH (15 mL) and AcOH (0.5 mL) and then 2M NH₃/MeOH (30 mL) was added. Solvent was removed in vacuo. The product was purified by flash chromatography eluting with MeOH/DCM (1-5%) to give N5-(3-(1H-pyrazolo[3,4-d]pyrimidin-4-yl)

pyridin-2-yl)-6-methyl-N1-(3-(trifluoromethyl)phenyl)
isoquinoline-1,5-diamine. MS (ESI, pos. ion) m/z: 513.2
[M+H]+

Example 39

Via Method J

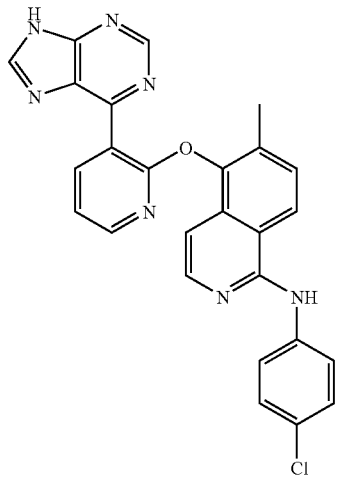 [SMILES: Cc1ccc2c(Nc3ccc(Cl)cc3)nccc2c1Oc1ncccc1-c1ncnc2[nH]cnc12]

Preparation of 5-(3-(9H-purin-6-yl)pyridin-2-yloxy)-
N-(4-chlorophenyl)-6-methylisoquinolin-1-amine Step 1: Preparation of 5-(3-(9-(4-methoxybenzyl)-
9H-purin-6-yl)pyridin-2-yloxy)-6-methylisoquino-
lin-1(2H)-one A mixture of 9-(4-methoxybenzyl)-6-(2-fluoropyridin-3-yl)-9H-purine (0.48 g, 1.4 mmol), 5-hydroxy-6-methylisoquinolin-1(2H)-one (0.25 g, 1.4 mmol) and cesium carbonate (1.1 g, 3.3 mmol) in NMP (5 mL) was stirred and heated in a Discover® model microwave reactor (CEM, Matthews, N.C.) at 130° C. for 60 min (100 watts, Powermax feature on, ramp time 1 min) The crude reaction mixture was partitioned between 3:1 CHCl$_3$:IPA (100 mL) and water (150 mL). The aqueous phase was extracted with 3:1 CHCl$_3$:IPA (50 mL). The combined organic extracts were washed with 1 N NaOH (2×75 mL), water (2×75 mL), satd NaCl (50 mL), dried over Na$_2$SO$_4$, filtered, and concentrated in vacuo to give a viscous brown oil which was chromatographed through a Redi-Sep® pre-packed silica gel column (80 g), eluting with a gradient of 1% to 7% MeOH in CH$_2$Cl$_2$, to provide 5-(3-(9-(4-methoxybenzyl)-9H-purin-6-yl)pyridin-2-yloxy)-6-methylisoquinolin-1(2H)-one (0.35 g, 51% yield) as a white solid. MS (ESI, pos. ion) m/z: 491.2 [M+H]+.

Step 2: Preparation of 5-(3-(9-(4-methoxybenzyl)-
9H-purin-6-yl)pyridin-2-yloxy)-1-chloro-6-methyl-
isoquinoline A mixture of 5-(3-(9-(4-methoxybenzyl)-9H-purin-6-yl)pyridin-2-yloxy)-6-methylisoquinolin-1(2H)-one (0.76 g, 1.5 mmol) in phosphorous oxychloride (10 mL, 107 mmol) was stirred in a 100° C. oil bath for 1.0 h. The reaction mixture was allowed to cool to RT, diluted with toluene (100 mL) and concentrated in vacuo. The residue was partitioned between DCM (100 mL) and satd NaHCO$_3$ (70 mL). The aqueous layer was extracted with DCM (50 mL). The combined organic layers were washed with satd NaHCO$_3$ (50 mL), water (50 mL) brine (50 mL), dried over Na$_2$SO$_4$, filtered, and concentrated in vacuo to give 960 mg as a dark red solid. The crude product was adsorbed onto a plug of silica gel and chromatographed through a Redi-Sep® pre-packed silica gel column (80 g), eluting with a gradient of 50% to 80% EtOAc in CH$_2$Cl$_2$, to provide 5-(3-(9-(4-methoxybenzyl)-9H-purin-6-yl)pyridin-2-yloxy)-1-chloro-6-methylisoquinoline as a clear viscous oil that solidified to a white solid upon standing. MS (ESI, pos. ion) m/z: 509.2 [M+H]+.

Step 3: Preparation of 5-(3-(9-(4-methoxybenzyl)-
9H-purin-6-yl)pyridin-2-yloxy)-N-(4-chlorophenyl)-
6-methylisoquinolin-1-amine A mixture of 5-(3-(9-(4-methoxybenzyl)-9H-purin-6-yl)pyridin-2-yloxy)-1-chloro-6-methylisoquinoline (0.250 g, 0.491 mmol) and 4-chloroaniline (0.0752 g, 0.589 mmol) in anhydrous 1,4 dioxane (10 mL) was vacuum purged with Ar three times, then 2-dicyclohexylphosphino-2'-(N,N-dimethylamino)biphenyl (0.0309 g, 0.0786 mmol) and tris(dibenzylideneacetone)palladium (0) (0.0180 g, 0.0196 mmol) were added. The suspension was sonicated for 2 min, then treated dropwise with lithium bis(trimethylsilyl)amide (1.0 M solution in THF; 0.69 mL, 0.69 mmol). The resulting brown solution was stirred in a 50° C. oil bath for 45 min. The reaction mixture was allowed to cool to RT (22° C.) and quenched with 1N aq HCl (5 mL). After stirring at RT for 10 min, the mixture was added to satd NaHCO$_3$ (70 mL) and extracted with EtOAc (2×50 mL). The combined extracts were washed with water (50 mL), satd NaCl (50 mL), dried over Na$_2$SO$_4$, filtered, and concentrated in vacuo to give 530 mg as a yellow residue. The crude product was adsorbed onto a plug of silica gel and chromatographed through a Redi-Sep® pre-packed silica gel column (40 g), eluting with a gradient of 30% to 60% EtOAc in CH$_2$Cl$_2$, to provide 5-(3-(9-(4-methoxybenzyl)-9H-purin-6-yl)pyridin-2-yloxy)-N-(4-chlorophenyl)-6-methylisoquinolin-1-amine as a clear film. MS (ESI, pos. ion) m/z: 600.2 [M+H]+.

Step 4: Preparation of 5-(3-(9H-purin-6-yl)pyridin-2-
yloxy)-N-(4-chlorophenyl)-6-methylisoquinolin-1-
amine A solution of 5-(3-(9-(4-methoxybenzyl)-9H-purin-6-yl)pyridin-2-yloxy)-N-(4-chlorophenyl)-6-methylisoquinolin-1-amine (0.22 g, 0.37 mmol) in TFA (5 mL) was stirred in a 65° C. oil bath for 3.5 h. The TFA was removed in vacuo and the residue was dissolved in MeOH (50 mL) and 2 M NH$_3$ in MeOH (50 mL) and adsorbed onto a pad of silica gel. The crude product was chromatographed through a Redi-Sep® pre-packed silica gel column (12 g), eluting with a gradient of 1% to 8% 1 M NH$_3$.MeOH in CH$_2$Cl$_2$ (over 20 min), to give 5-(3-(9H-purin-6-yl)pyridin-2-yloxy)-N-(4-chlorophenyl)-6-methylisoquinolin-1-amine as a white solid. $^1$H NMR (400 MHz, DMSO-d$_6$) □ ppm 2.23 (s, 3H), 7.24-7.33 (m, 2H), 7.35 (d, J=8.53 Hz, 2H), 7.53 (d, J=8.53 Hz, 1H), 7.88-7.97 (m, 3H), 8.13 (d, J=5.02 Hz, 1H), 8.24 (d, J=7.53 Hz, 1H), 8.34 (d, J=8.53 Hz, 1H), 8.68 (s, 1H), 9.07 (s, 1H), 9.27 (s, 1H), 13.64 (s, 1H); MS (ESI, pos. ion) m/z: 480.1 [M+H]+

Table I includes additional representative compounds of Formulas I and II, including many of those exemplified above. Included in Table 1 is the method by which the Example was prepared, the MS data found, and Raf kinase biological date for each compound

TABLE I

| Ex. No. | Syn. Method | Compound Name (IUPAC) | Found MS (M + H)+ | HTRF Enzyme assay Data IC$_{50}$ uM | B-Raf cell assay Data IC$_{50}$ uM |
|---|---|---|---|---|---|
| 40 | A | 4-((6-methyl-5-((3-(7H-pyrrolo[2,3-d]pyrimidin-4-yl)-2-pyridinyl)amino)-1-isoquinolinyl)amino)benzonitrile | 469.2 | 0.003 | 0.023 |
| 41 | A | 6-methyl-N-1-(2-methyl-5-((trifluoromethyl)oxy)phenyl)-N-5-(3-(7H-pyrrolo[2,3-d]pyrimidin-4-yl)-2-pyridinyl)-1,5-isoquinolinediamine | 542.2 | 0.035 | 0.107 |
| 42 | A | N-1-(4-chlorophenyl)-6-methyl-N-5-(3-(7H-pyrrolo[2,3-d]pyrimidin-4-yl)-2-pyridinyl)-1,5-isoquinolinediamine | 478.2 | 0.003 | 0.005 |
| 43 | A | N-1-(3-ethynylphenyl)-6-methyl-N~5~-(3-(7H-pyrrolo[2,3-d]pyrimidin-4-yl)-2-pyridinyl)-1,5-isoquinolinediamine | 468.2 | 0.003 | 0.010 |
| 44 | A | N-1-(2,2-difluoro-1,3-benzodioxol-5-yl)-6-methyl-N-5-(3-(7H-pyrrolo[2,3-d]pyrimidin-4-yl)-2-pyridinyl)-1,5-isoquinolinediamine | 524.2 | 0.013 | 0.025 |
| 45 | A | 3,3-difluoro-1-methyl-5-((6-methyl-5-((3-(7H-pyrrolo[2,3-d]pyrimidin-4-yl)-2-pyridinyl)amino)-1-isoquinolinyl)amino)-1,3-dihydro-2H-indol-2-one | 549.2 | 0.008 | 0.015 |
| 46 | A | 3,3-difluoro-5-((6-methyl-5-((3-(7H-pyrrolo[2,3-d]pyrimidin-4-yl)-2-pyridinyl)amino)-1-isoquinolinyl)amino)-1,3-dihydro-2H-indol-2-one | 535.2 | 0.015 | 0.025 |
| 47 | A | (3R)-3-methyl-6-((6-methyl-5-((3-(7H-pyrrolo[2,3-d]pyrimidin-4-yl)-2-pyridinyl)amino)-1-isoquinolinyl)amino)-1,3-dihydro-2H-indol-2-one | 513.2 | 0.010 | 0.011 |
| 48 | A | 6-methyl-N-1-(3-methyl-1,2-benzisothiazol-5-yl)-N-5-(3-(7H-pyrrolo[2,3-d]pyrimidin-4-yl)-2-pyridinyl)-1,5-isoquinolinediamine | 515.2 | 0.011 | 0.015 |
| 49 | A | N-1-1,3-benzothiazol-6-yl-6-methyl-N-5-(3-(7H-pyrrolo[2,3-d]pyrimidin-4-yl)-2-pyridinyl)-1,5-isoquinolinediamine | 501.2 | 0.007 | 0.010 |
| 50 | A | 6-((6-methyl-5-((3-(7H-pyrrolo[2,3-d]pyrimidin-4-yl)-2-pyridinyl)amino)-1-isoquinolinyl)amino)-1,3-dihydro-2H-indol-2-one | 499.2 | 0.012 | 0.045 |
| 51 | A | 3,3-dimethyl-6-((6-methyl-5-((3-(7H-pyrrolo[2,3-d]pyrimidin-4-yl)-2-pyridinyl)amino)-1-isoquinolinyl)amino)-1,3-dihydro-2H-indol-2-one | 527.2 | 0.025 | 0.012 |
| 52 | A | 4-methyl-7-((6-methyl-5-((3-(7H-pyrrolo[2,3-d]pyrimidin-4-yl)-2-pyridinyl)amino)-1-isoquinolinyl)amino)-2(1H)-quinolinone | 525.2 | 0.007 | 0.007 |
| 53 | A | 6-methyl-N-5-(3-(7H-pyrrolo[2,3-d]pyrimidin-4-yl)-2-pyridinyl)-N-1-(4-(trifluoromethyl)phenyl)-1,5-isoquinolinediamine | 512.2 | 0.047 | 0.052 |
| 54 | A | 6-methyl-N-5-(3-(7H-pyrrolo[2,3-d]pyrimidin-4-yl)-2-pyridinyl)-N-1-(2,2,4,4-tetrafluoro-4H-1,3-benzodioxin-6-yl)-1,5-isoquinolinediamine | 574.2 | 0.205 | 0.099 |
| 55 | B | N-5-(2-chloro-5-(7H-pyrrolo[2,3-d]pyrimidin-4-yl)-4-pyrimidinyl)-6-methyl-N-1-(2-methyl-5-(trifluoromethyl)phenyl)-1,5-isoquinolinediamine | 561.2 | 0.015 | 0.086 |
| 56 | C | N-1-(4-chlorophenyl)-6-methyl-N-5-(3-(9H-purin-6-yl)-2-pyridinyl)-1,5-isoquinolinediamine | 479.1 | 0.002 | 0.002 |

TABLE I-continued

| Ex. No. | Syn. Method | Compound Name (IUPAC) | Found MS (M + H)+ | HTRF Enzyme assay Data IC$_{50}$ uM | B-Raf cell assay Data IC$_{50}$ uM |
|---|---|---|---|---|---|
| 57 | C | 4-((6-methyl-5-((3-(9H-purin-6-yl)-2-pyridinyl)amino)-1-isoquinolinyl)amino)benzonitrile | 470.2 | 0.0006 | 0.004 |
| 58 | C | 6-methyl-N-5-(3-(9H-purin-6-yl)-2-pyridinyl)-N-1-(3-(trifluoromethyl)phenyl)-1,5-isoquinolinediamine | 513.2 | 0.006 | 0.006 |
| 59 | C | N-1-(2,2-difluoro-1,3-benzodioxol-5-yl)-6-methyl-N-5-(3-(9H-purin-6-yl)-2-pyridinyl)-1,5-isoquinolinediamine | 525.2 | 0.006 | 0.006 |
| 60 | E | 4-((7-methyl-8-((3-(7H-pyrrolo[2,3-d]pyrimidin-4-yl)-2-pyridinyl)amino)-4-quinazolinyl)amino)benzonitrile | 470.2 | 0.010 | 0.233 |
| 61 | F | 4-((7-methyl-8-((3-(9H-purin-6-yl)-2-pyridinyl)amino)-4-quinazolinyl)amino)benzonitrile | 471.2 | 0.002 | 0.103 |
| 62 | G | N-1-(4-chlorophenyl)-6-methyl-N-5-(3-(5H-pyrrolo[3,2-d]pyrimidin-4-yl)-2-pyridinyl)-1,5-isoquinolinediamine | 478.2 | 0.020 | 0.282 |
| 63 | G | 4-((6-methyl-5-((3-(5H-pyrrolo[3,2-d]pyrimidin-4-yl)-2-pyridinyl)amino)-1-isoquinolinyl)amino)benzonitrile | 469.2 | 0.171 | 1 |
| 64 | G | N-1-(2,2-difluoro-1,3-benzodioxol-5-yl)-6-methyl-N-5-(3-(5H-pyrrolo[3,2-d]pyrimidin-4-yl)-2-pyridinyl)-1,5-isoquinolinediamine | 524.2 | 0.302 | 0.111 |
| 65 | H | 6-methyl-N-5-(3-(1H-pyrazolo[3,4-d]pyrimidin-4-yl)-2-pyridinyl)-N-1-(3-(trifluoromethyl)phenyl)-1,5-isoquinolinediamine | 513.2 | 0.008 | 0.008 |
| 66 | H | N5-(3-(1H-pyrazolo[3,4-d]pyrimidin-4-yl)pyridin-2-yl)-N1-(4-methoxy-3-(trifluoromethyl)phenyl)-6-methylisoquinoline-1,5-diamine | 543.2 | 0.025 | 0.028 |
| 67 | H | N5-(3-(1H-pyrazolo[3,4-d]pyrimidin-4-yl)pyridin-2-yl)-N1-(4-chlorophenyl)-6-methylisoquinoline-1,5-diamine | 479.1 | 0.005 | 0.003 |
| 68 | J | N-(4-chlorophenyl)-6-methyl-5-((3-(9H-purin-6-yl)-2-pyridinyl)oxy)-1-isoquinolinamine | 480.1 | 0.026 | 1 |

Example 69

Method K

Preparation of N5-(5-(9H-purin-6-yl)pyrimidin-4-yl)-N1-(4-chlorophenyl)-6-methylisoquinoline-1,5-diamine

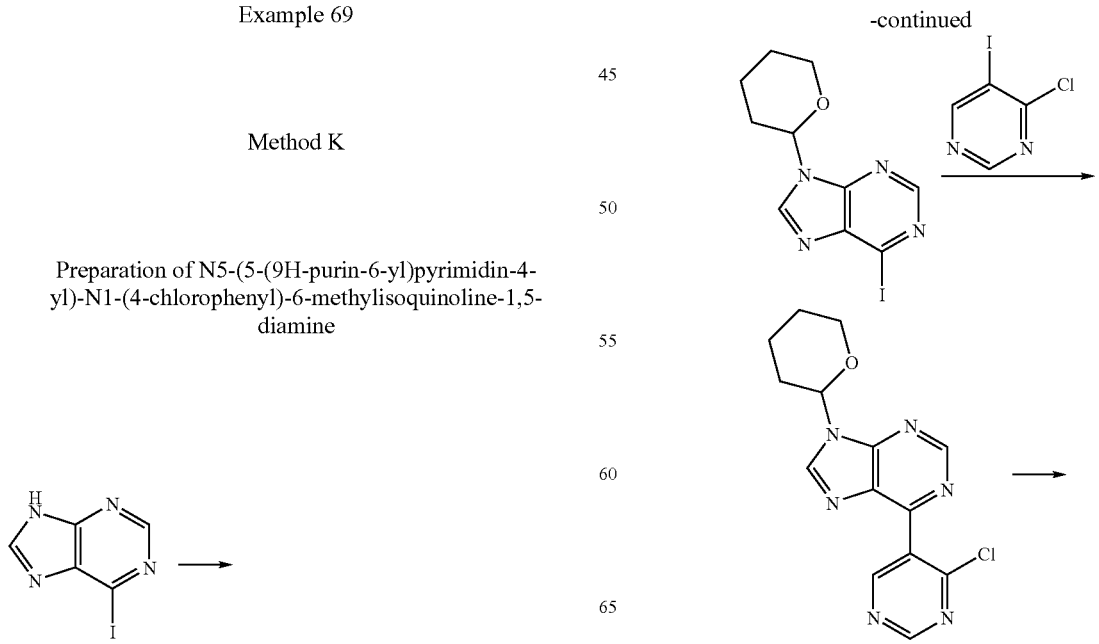

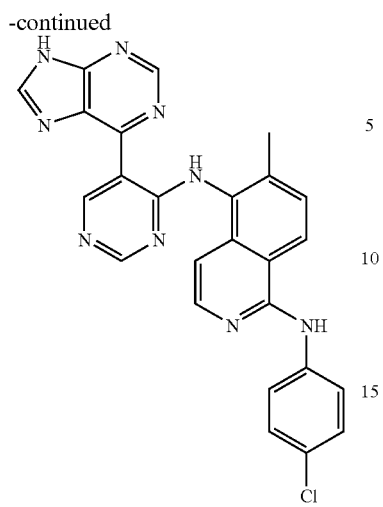

Step 1: 6-Iodo-9-(tetrahydro-2H-pyran-2-yl)-9H-purine

In a RB flask were placed 6-iodo-9H-purine (2680 mg, 10894 μmol), 3,4-dihydro-2(H)-pyran (2982 μl, 32682 μmol), and p-toluenesulfonic acid monohydrate (34.0 mg, 218 μmol) in EtOAc (150 mL) and heated to reflux for 2 hours. After cooling to RT, the reaction mixture was washed with NaHCO$_3$ (aq., sat., 100 mL), then brine (100 mL). The organic solution was concentrated in vacuo. The residue was redissolved in a small amount of DCM and then put on a layer of silica gel in a funnel. The silica was rinsed with EtOAc/hexane (1:1). A light yellow solution (filtrate) was collected and concentrated to give a waxy product. This product was treated with hexanes to give the titled compound as an off white solid. MS Found: (ESI pos. ion) m/z 331 (M+H$^+$).

Step 2: 6-(4-Chloropyrimidin-5-yl)-9-(tetrahydro-2H-pyran-2-yl)-9H-purine

6-Iodo-9-(tetrahydro-2H-pyran-2-yl)-9H-purine (620 mg, 1878 μmol) was dissolved in THF (1 mL) in a 15 mL microwave tube and sealed. The solution was flushed with argon and then cooled to −40° C. A solution of isopropylmagnesium chloride (2254 μl, 2254 μmol) (LiCl complex, 1 N in THF) was added in dropwise slowly. The reaction was allowed to stirred at −40° C. for 15 min, LCMS showed incompletion of Mg—I exchange. The mixture was warmed to rt, LCMS indicated Mg—I exchange was still not completed, and then the mixture was cooled to −40° C. again and a solution of isopropylmagnesium chloride-LiCl complex (1 N in THF, 1 mL) was added again in dropwise via a syringe. The reaction mixture was stirred at this temperature for 20 min (LCMS showed all starting material consumed). Under −40° C., a solution of zinc chloride, 0.5 M in THF (4883 μl, 2441 μmol) was added in dropwise. Another 2 mL of the zinc chloride solution was added in to counter the additional Mg reagent. The mixture was stirred at this temperature for 1 hr and gradually warmed to RT. This solution was poured into a solution of 4-chloro-5-iodopyrimidine (429 mg, 1784 μmol), tris(dibenzylideneacetone)dipalladium(0) (103 mg, 113 μmol), and tri-2-furylphosphine (105 mg, 451 μmol) (TFP) in THF (15 mL) flushed with argon. This reaction mixture was heated to 60° C. under argon for 16 hours. The reaction mixture was cooled to rt and quenched with NH$_4$Cl (aq., sat., 10 mL) and partitioned between H$_2$O and EtOAc, 40 mL each. The organic was collected, and filtered through a layer of silica gel. The silica layer was rinsed with THF (80 mL). The filtrate was combined and concentrated. The residue was loaded on silica gel and purified via flash column on silica (A: hexane, B: 1:1 THF/EtOAc, B:A=5-40%). Desired fractions were collected and concentrated to give a dark brown gel. This brown gel was precipitated with hexane:EtOAc=1:1 to give a light brown solid. This solid was washed with the same solvent once and then dried in the air to give 6-(4-chloropyrimidin-5-yl)-9-(tetrahydro-2H-pyran-2-yl)-9H-purine. MS Found: (ESI pos. ion) m/z 317 (M+H$^+$).

Step 3: N-5-(5-(9H-purin-6-yl)pyrimidin-4-yl)-N1-(4-chlorophenyl)-6-methylisoquinoline-1,5-diamine In a 2 mL microwave reaction tube were added 6-(4-chloropyrimidin-5-yl)-9-(tetrahydro-2H-pyran-2-yl)-9H-purine (31 mg, 98 mop and N1-(4-chlorophenyl)-6-methylisoquinoline-1,5-diamine (28 mg, 98 μmol) in DMF (0.6 mL). The mixture was thoroughly mixed and flushed with argon then sealed. It was stirred at 70° C. The temperature was raised to 90° C. after 2 hrs and allowed over night. The reaction mixture was partitioned in EtOAc and NaHCO$_3$. The organic layer was washed with brine and dried over Na$_2$SO$_4$. The residue was treated with MeOH (3 mL) and conc HCl (0.2 mL). The mixture was stirred for 2 hrs, then partitioned between NaHCO$_3$ and EtOAc (10 mL each). The organic layer was collected and purified by prep HPLC (MeCN/H$_2$O=5-95% with 0.1% TFA). Desired fractions were combined and neutralized with NaHCO$_3$ (sat., aq.) and extracted with DCM. The DCM layer was washed with brine then dried over Na$_2$SO$_4$, then dried over a stream of N$_2$ to give a yellow solid N5-(5-(9H-purin-6-yl)pyrimidin-4-yl)-N1-(4-chlorophenyl)-6-methylisoquinoline-1,5-diamine. MS Found: (ESI pos. ion) m/z 480 (M+H$^+$).

Example 70

Preparation of 4-(8-(3-(1H-pyrazolo[3,4-d]pyrimidin-4-yl)pyridin-2-ylamino)-7-methylquinazolin-4-ylamino)benzonitrile

Step 1: 4-(8-(3-(1-(4-Methoxybenzyl)-1H-pyrazolo[3,4-d]pyrimidin-4-yl)pyridin-2-ylamino)-7-methylquinazolin-4-ylamino)benzonitrile A mixture of 1-(4-methoxybenzyl)-4-(2-fluoropyridin-3-yl)-1H-pyrazolo[3,4-d]pyrimidine (150 mg, 447 mmol) and 4-(8-amino-7-methylquinazolin-4-ylamino)benzonitrile (135 mg, 492 mmol) in THF (3 ml) was sonicated until the solid became a fine powder. To this mixture was added lithium bis(trimethylsilyl)amide, 1.0 M solution in THF) (1476 μl, 1476 mmol) slowly. The mixture was stirred at it for 4 hr (LCMS: some SM) and then heated in a microwave synthesizer at 60° C. for 20 min The mixture was poured into MeOH (15 ml) and AcOH (0.5 ml) was added and then NH$_3$/MeOH (2 M, 20 mL) was added. Solvent was removed in vacuo. The product was purified by flash chromatography eluting with MeOH/DCM (1-5%) to give 4-(8-(3-(1-(4-methoxybenzyl)-1H-pyrazolo[3,4-d]pyrimidin-4-yl)pyridin-2-ylamino)-7-methylquinazolin-4-ylamino)benzonitrile. MS Found (ESI pos. ion) m/z 591 (M+H$^+$).

Step 2: 4-(8-(3-(1H-Pyrazolo[3,4-d]pyrimidin-4-yl)pyridin-2-ylamino)-7-methylquinazolin-4-ylamino)benzonitrile A mixture of 4-(8-(3-(1-(4-methoxybenzyl)-1H-pyrazolo[3,4-d]pyrimidin-4-yl)pyridin-2-ylamino)-7-methylquinazolin-4-ylamino)benzonitrile (120 mg, 203 μmol) in TFA (3 ml) was heated at 65° C. for 3 hr. TFA was removed under vacuum. MeOH (2N, NH$_3$) (20 ml) was added and then solvent was removed under vacuum. The product was purified by flash chromatography eluting with MeOH/DCM (1-5%) to give 4-(8-(3-(1H-pyrazolo[3,4-d]pyrimidin-4-yl)pyridin-2-ylamino)-7-methylquinazolin-4-ylamino)benzonitrile. MS (ESI pos. ion) m/z 471 (M+H$^+$).

Example 71

Method L

Preparation of 4-(5-(3-(1H-pyrazolo[3,4-d]pyrimidin-4-yl)pyridin-2-ylamino)-6-methylisoquinolin-1-ylamino)benzonitrile

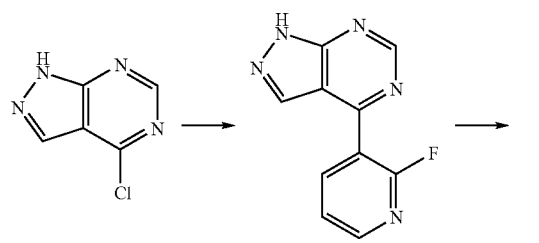

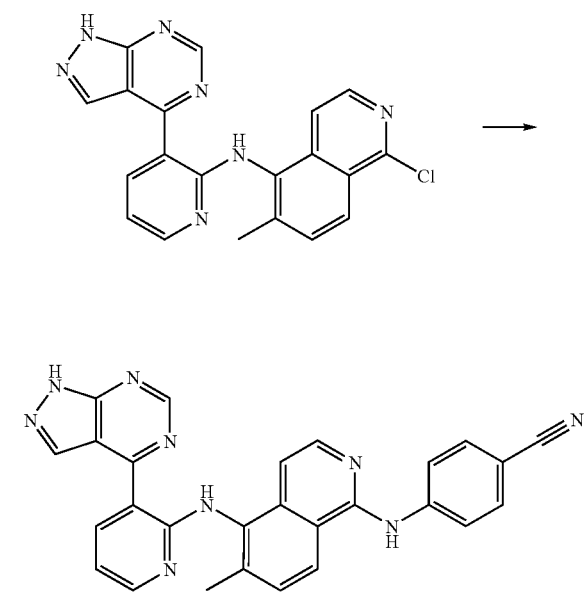

Step 1: 4-(2-Fluoropyridin-3-yl)-1H-pyrazolo[3,4-d]pyrimidine

A mixture of potassium acetate (13 g, 130 mmol), PdCl$_2$(P-t-Bu$_2$Ph)$_2$ (1.1 g, 1.7 mmol), 4-chloro-1H-pyrazolo[3,4-d]pyrimidine (6.70 g, 43 mmol) and 2-fluoropyridin-3-ylboronic acid (7.3 g, 52 mmol) in EtOH (300 ml)-water (100 ml) was sonicated until the solid became a fine powder and degassed under vacuum. The mixture was refluxed under N$_2$ overnight. After cooling to rt solvent was removed in vacuo and to the residues was added water (200 ml) and NaHCO$_3$ (sat. 150 ml). The mixture was stirred for 15 min. The solid was filtered and washed with water. The solid was dissolved in MeOH-DCM and preloaded on silica gel and purified by flash chromatography eluting with MeOH/DCM (1-5%) to give 4-(2-fluoropyridin-3-yl)-1H-pyrazolo[3,4-d]pyrimidine. MS Found: (ESI pos. ion) m/z 216 (M+H$^+$).

Step 2: N-(3-(1H-pyrazolo[3,4-d]pyrimidin-4-yl)pyridin-2-yl)-1-chloro-6-methylisoquinolin-5-amine A mixture of 1-chloro-6-methylisoquinolin-5-amine (414 mg, 2147 μmol) and 4-(2-fluoropyridin-3-yl)-1H-pyrazolo[3,4-d]pyrimidine (420 mg, 1952 μmol) in THF (20 ml) was sonicated until all solid became a fine powder. Lithium bis(trimethylsilyl)amide, 1.0 M solution in THF (6831 μl, 6831 mmol) was then added (all solids were dissolved and color changed) The mixture was stirred at rt overnight. The mixture was poured into a mixture of MeOH (20 ml) and AcOH (2 ml) and then solvent was removed in vacuo. 2 M NH$_3$/MeOH (30 ml) was added and then solvent was removed in vacuo. The product was purified by flash chromatography eluting with MeOH/DCM (0-5%) to give N-(3-(1H-pyrazolo[3,4-d]pyrimidin-4-yl)pyridin-2-yl)-1-chloro-6-methylisoquinolin-5-amine. MS Found (ESI pos. ion) m/z 388 (M+H$^+$).

Step 3: 4-(5-(3-(1H-pyrazolo[3,4-d]pyrimidin-4-yl)pyridin-2-ylamino)-6-methylisoquinolin-1-ylamino)benzonitrile A mixture of N-(3-(1H-pyrazolo[3,4-d]pyrimidin-4-yl)pyridin-2-yl)-1-chloro-6-methylisoquinolin-5-amine (160 mg, 413 mmol), 4-aminobenzonitrile (53.6 mg, 454 μmol), tris(dibenzylideneacetone)dipalladium(0) (18.9 mg, 20.6 μmol) and DavePhos (17.9 mg, 45.4 mmol) in THF (3 ml) was slightly vacuumed to de-gas, and then lithium bis(trimethylsilyl)amide (1.0 M solution in THF) (1857 μl, 1857 μmol) was added and the microwave tube was sealed under N$_2$ gas. The mixture was heated in a microwave reactor at 100° C. for 30 min. The mixture was poured into DCM (10 ml)-AcOH (0.5 ml) and stirred for 10 min, then Et$_3$N (0.5 ml) was added. Solvent was removed under vacuum and the residue was purified by flash chromatography eluting with MeOH/DCM (1-4%) to give 4-(5-(3-(1H-pyrazolo[3,4-d]pyrimidin-4-yl)pyridin-2-ylamino)-6-methylisoquinolin-1-ylamino)benzonitrile. MS Found: (ESI pos. ion) m/z 470 (M+H$^+$).

Example 72

Preparation of N5-(3-(1H-pyrazolo[3,4-d]pyrimidin-4-yl)pyridin-2-yl)-N1-(2,2-difluorobenzo[d][1,3]dioxol-5-yl)-6-methylisoquinoline-1,5-diamine A mixture of 2,2-difluorobenzo[d][1,3]dioxol-5-amine (64 mg, 371 mop, N-(3-(1H-pyrazolo[3,4-d]pyrimidin-4-yl)pyridin-2-yl)-1-chloro-6-methylisoquinolin-5-amine (120 mg, 309 μmol) and 2,2,2-trifluoroacetic acid (95 μl, 1238 μmol) in i-PrOH (4 ml) was heated in a microwave reactor at 150° C. for 40 min. The mixture was poured into MeOH (10 ml) and Et$_3$N (0.25 ml) was added. Solvent was removed under vacuum and the product was purified by flash chromatography eluting with MeOH/DCM (1-5%) to give N5-(3-(1H-pyrazolo[3,4-d]pyrimidin-4-yl)pyridin-2-yl)-N1-(2,2-difluorobenzo[d][1,3]dioxol-5-yl)-6-methylisoquinoline-1,5-diamine. MS Found: (ESI pos. ion) m/z 525 (M+H⁺).

Example 73

Method M

Preparation of N8-(3-(9H-purin-6-yl)pyridin-2-yl)-N4-(2,2-difluorobenzo[d][1,3]dioxol-5-yl)-7-methylquinazoline-4,8-diamine

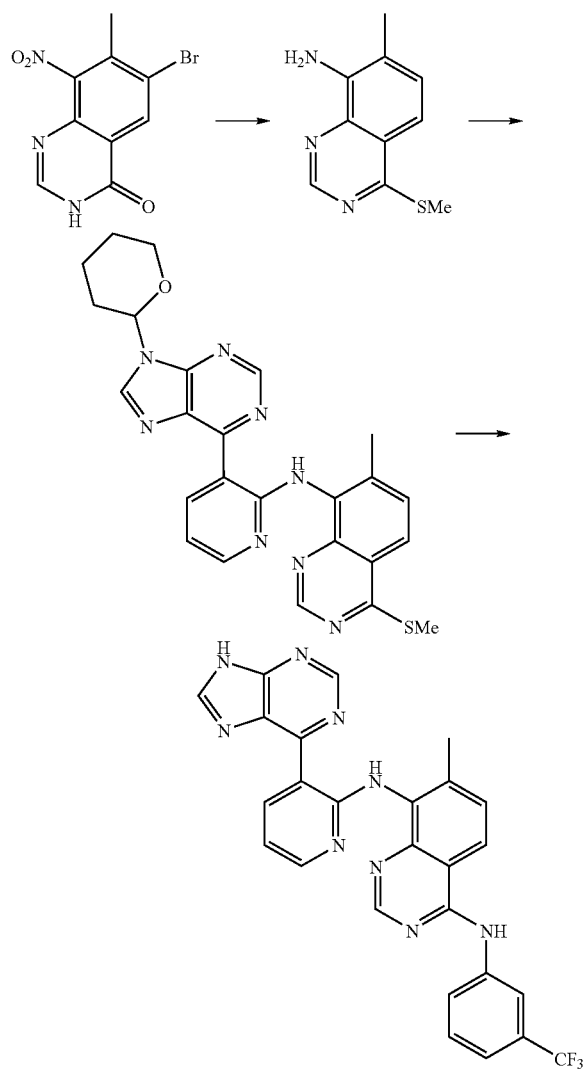

Step 1: 8-Amino-7-methylquinazolin-4(3H)-one

6-Bromo-7-methyl-8-nitroquinazolin-4(3H)-one (4.8 g, 17 mmol) was suspended in EtOH (500 ml) and degassed using a vacuum line. The mixture was then evacuated with nitrogen and 10% Pd/C (1.4 g) was added under a positive flow of nitrogen. The reaction was then placed under a hydrogen atmosphere with a large balloon while stirring. After 4 days, the reaction was filtered through a pad of celite. The filtrate was reduced under vacuum and the residue was triturated with ether to give 8-amino-7-methylquinazolin-4(3H)-one as an off white solid. MS Found: (ESI pos. ion) m/z 176 (M+H⁺).

Step 2: 7-Methyl-4-(methylthio)quinazolin-8-amine

A heavy wall vessel was charged with 8-amino-7-methylquinazolin-4(3H)-one (6.00 g, 34 mmol), Lawesson's Reagent (17 g, 41 mmol) and pyridine (83 ml, 1027 mmol). The vessel was capped and heated to 100° C. for 12 hours. The reaction was cooled down to RT and poured into ice water (500 ml). A gummy solid formed and stuck to the sides of the flask. The mother liquor was decanted off and the gummy solid left behind was dissolved in a DCM/MeOH mixture. The volatiles were evaporated and the residue was suspended in methanol:water (1:1-15 ml). Then 1M aqueous NaOH (48 ml, 48 mmol) was added, dissolving most of the suspended solid. Iodomethane (2.4 ml, 38 mmol) was added dropwise. The reaction was stirred for 30 mins during which time a solid precipitated out of solution. The methanol was removed under vacuum and the reaction was diluted with water. The solid was filtered off and purified by column chromatography on silica gel using a gradient of 20 to 60% EtOAc in hexanes to give 7-methyl-4-(methylthio)quinazolin-8-amine as an off-white solid. MS Found: ESI pos. ion) m/z 206 (M+H⁺).

Step 3: 7-Methyl-4-(methylthio)-N-(3-(9-(tetrahydro-2H-pyran-2-yl)-9H-purin-6-yl)pyridin-2-yl)quinazolin-8-amine A 250 ml flask was charged with 6-(2-fluoropyridin-3-yl)-9-(tetrahydro-2H-pyran-2-yl)-9H-purine (2.92 g, 9.74 mmol) and 7-methyl-4-(methylthio)quinazolin-8-amine (2.00 g, 9.74 mmol) along with 20 ml of dioxane. 1.0 M LiHMDS in THF (29.2 ml, 29.2 mmol) was then added dropwise at RT. The reaction was stirred for 6 hrs and then treated with 5 ml of HOAc. The volatiles were removed under vacuum. The residue was dissolved in chloroform and washed (2×) with an aqueous saturated solution of sodium bicarbonate, then with water and then brine. The organic layer was then dried with sodium sulfate and purified by column chromatography on silica gel eluting with a gradient of 20 to 60% EtOAc in hexanes to give 7-methyl-4-(methylthio)-N-(3-(9-(tetrahydro-2H-pyran-2-yl)-9H-purin-6-yl)pyridin-2-ylquinazolin-8-amine as a yellow solid. MS Found: (ESI pos. ion) m/z 485 (M+H⁺).

Step 4: N-8-(3-(9H-purin-6-yl)pyridin-2-yl)-7-methyl-N4-(3-(trifluoromethyl)phenyl)quinazoline-4,8-diamine A clear microwave vial was charged with 7-methyl-4-(methylthio)-N-(3-(9-(tetrahydro-2H-pyran-2-yl)-9H-purin-6-yl)pyridin-2-yl)quinazolin-8-amine (0.050 g, 0.10 mmol) and 5 ml of dioxane. A few drops of TFA was added to the mixture and the reaction vial was capped. The vial was heated in a microwave reactor at 160° C. for 12 minutes. The reaction was diluted with 2M ammonia in MeOH and EtOAc. The mixture was loaded onto silica gel and purified by column chromatography on silica gel using a gradient of 0 to 10% MeOH in DCM. The pure fractions were reduced and triturated with ether to give N-8-(3-(9H-purin-6-yl)pyridin-2-yl)-7-methyl-N4-(3-(trifluoromethyl)phenyl)quinazoline-4,8-diamine as a yellow solid. MS Found: (ESI pos. ion) m/z 514 (M+H⁺).

Example 74

Preparation of N-8-(3-(9H-purin-6-yl)pyridin-2-yl)-N-4-(2,2-difluorobenzo[d][1,3]dioxol-5-yl)-7-methylquinazoline-4,8-diamine A clear microwave vial was charged with 7-methyl-4-(methylthio)-N-(3-(9-(tetrahydro-2H-pyran-2-yl)-9H-purin-6-yl)pyridin-2-yl)quinazolin-8-amine (0.180 g, 0.37 mmol) and 2,2-difluorobenzo[d][1,3]dioxol-5-amine (0.13 g, 0.74 mmol) and 5 ml of dioxane. A few drops of TFA was added to the mixture and the reaction vial was capped. The vial was heated in a microwave reactor at 160° C. for 12 minutes. The reaction was diluted with 2M ammonia in MeOH and ethyl acetate. The mixture was loaded onto silica gel and purified by column chromatography on silica gel using a gradient of 0 to 10% MeOH in DCM. The pure fractions were reduced and triturated with ether to give N-8-(3-(9H-purin-6-yl)pyridin-2-yl)-N-4-(2,2-difluorobenzo[d][1,3]dioxol-5-yl)-7-methylquinazoline-4,8-diamine as a yellow solid. MS Found: (ESI pos. ion) m/z 526 (M+H$^+$).

Example 75

Preparation of N-8-(3-(9H-purin-6-yl)pyridin-2-yl)-N4-(3-ethynylphenyl)-7-methylquinazoline-4,8-diamine A clear microwave vial was charged with 7-methyl-4-(methylthio)-N-(3-(9-(tetrahydro-2H-pyran-2-yl)-9H-purin-6-yl)pyridin-2-yl)quinazolin-8-amine (0.280 g, 0.578 mmol), 3-ethynylbenzenamine (0.135 g, 1.16 mmol) and 5 ml of dioxane. A few drops of TFA was added to the mixture and the vial was capped. The vial was heated in a microwave reactor at 160° C. for 12 minutes. The reaction was diluted with 2M ammonia in MeOH and ethyl acetate. The mixture was loaded onto silica gel and purified by column chromatography on silica gel using a gradient of 0 to 10% MeOH in DCM. The pure fractions were reduced and triturated with ether to give N-8-(3-(9H-purin-6-yl)pyridin-2-yl)-N-4-(3-ethynylphenyl)-7-methylquinazoline-4,8-diamine as yellow solid. MS Found: (ESI pos. ion) m/z 470 (M+H$^+$).

Example 76

Preparation of N-8-(3-(9H-purin-6-yl)pyridin-2-yl)-N4-(4-(difluoromethoxy)phenyl)-7-methylquinazoline-4,8-diamine A clear microwave vial was charged with 7-methyl-4-(methylthio)-N-(3-(9-(tetrahydro-2H-pyran-2-yl)-9H-purin-6-yl)pyridin-2-yl)quinazolin-8-amine (0.060 g, 0.12 mmol), 4-(difluoromethoxy)benzenamine (0.039 g, 0.25 mmol) and 5 ml of dioxane. A few drops of TFA was added to the mixture and the reaction vial was capped. The vial was heated in a microwave reactor at 160° C. for 12 minutes. The reaction was diluted with 2M ammonia in MeOH and EtOAc. The mixture was loaded unto silica gel and purified by column chromatography on silica gel using a gradient of 0 to 10% MeOH in DCM. The pure fractions were reduced and triturated with ether to give N-8-(3-(9H-purin-6-yl)pyridin-2-yl)-N-4-(4-(difluoromethoxy)phenyl)-7-methylquinazoline-4,8-diamine as a yellow solid. MS Found: (ESI pos. ion) m/z 512 (M+H$^+$).

Example 77

Preparation of N-8-(3-(9H-purin-6-yl)pyridin-2-yl)-N-4-(4-chlorophenyl)-7-methylquinazoline-4,8-diamine A clear microwave vial was charged with 7-methyl-4-(methylthio)-N-(3-(9-(tetrahydro-2H-pyran-2-yl)-9H-purin-6-yl)pyridin-2-yl)quinazolin-8-amine (0.200 g, 0.413 mmol) and 4-chlorobenzenamine (0.105 g, 0.825 mmol) and 5 ml of dioxane. A few drops of TFA was added to the mixture and the reaction vial was capped. The vial was heated in a microwave reactor at 160° C. for 12 minutes. The solid that crashed out of the reaction mixture was filtered off and washed with ethyl acetate. The solid was dissolved in DMSO (3 ml) and purified by RP-HPLC using a gradient of 5% ACN 0.1% TFA to 95% ACN 0.1% TFA in water 0.1% TFA. The pure fractions were neutralized with ammonium hydroxide and the volatiles were removed under reduced pressure. The solid that crashed out of the aqueous layer was filtered off, washed with water and dried in a vacuum oven at 45 degrees to give N8-(3-(9H-purin-6-yl)pyridin-2-yl)-N4-(4-chlorophenyl)-7-methylquinazoline-4,8-diamine as a yellow solid. MS Found: (ESI pos. ion) m/z 480 (M+H$^+$).

Example 78

Preparation of N-5-(3-(9H-purin-6-yl)pyridin-2-yl)-N-1-((R)-1-(4-chlorophenyl)ethyl)-6-methylisoquinoline-1,5-diamine Step 1: (R)-N-(1-(4-chlorophenyl)ethyl)-6-methyl-5-nitroisoquinolin-1-amine A glass microwave reaction vessel was charged with 1-chloro-6-methyl-5-nitroisoquinoline (0.22 g, 1.0 mmol), (R)-1-(4-chlorophenyl)ethanamine (0.31 g, 2.0 mmol), 2,2,2-trifluoroacetic acid (0.011 g, 0.10 mmol) and isopropanol (1 mL). The reaction mixture was stirred and heated in a microwave reactor at 140° C. for 60 min. The reaction mixture was diluted with chloroform, washed with 10% sodium carbonate, dried over sodium sulfate and concentrated. The crude product was chromatographed on silica gel eluting with 20% ethyl acetate/hexane to give (R)-N-(1-(4-chlorophenyl)ethyl)-6-methyl-5-nitroisoquinolin-1-amine as a solid. MS Found: (ESI pos. ion) m/z 342 (M+H$^+$).

Step 2: (R)-N-1-(1-(4-Chlorophenyl)ethyl)-6-methylisoquinoline-1,5-diamine

To a 100 mL RBF was added (R)-N-(1-(4-chlorophenyl)ethyl)-6-methyl-5-nitroisoquinolin-1-amine (0.18 g, 0.53 mmol), tin (II) chloride dihydrate (0.60 g, 2.6 mmol) and ethanol (10 mL). The reaction mixture was heated at 70° C. in an oil bath for 18 h. The reaction mixture was concentrated, diluted with DCM, washed with 1N NaOH, dried over sodium sulfate and concentrated. The crude product was chromatographed on silica gel eluting with 40% ethyl acetate/hexane to give (R)-N-1-(1-(4-chlorophenyl)ethyl)-6-methylisoquinoline-1,5-diamine as a syrup. MS Found: (ESI pos. ion) m/z 312 (M+H$^+$).

Step 3: N-1-((R)-1-(4-Chlorophenyl)ethyl)-6-methyl-N-5-(3-(9-(tetrahydro-2H-pyran-2-yl)-9H-purin-6-yl)pyridin-2-yl)isoquinoline-1,5-diamine To a 50 mL RBF was added (R)-N1-(1-(4-chlorophenyl)ethyl)-6-methylisoquinoline-1,5-diamine (0.080 g, 0.26 mmol), 6-(2-fluoropyridin-3-yl)-9-(tetrahydro-2H-pyran-2-yl)-9H-purine (0.084 g, 0.28 mmol) and THF (4 mL). The reaction mixture was cooled at 0° C. in an ice bath. Then lithium bis(trimethylsilyl)amide (1.0 M in THF) (1.3 ml, 1.3 mmol) was added and the ice bath removed and stirred 2 h. The reaction mixture was diluted with sat. sodium bicarbonate and washed with EtOAc. The organic layer was washed with sat. sodium chloride, dried over sodium sulfate and concentrated. The crude product was chromatographed on silica gel eluting with 50% ethyl acetate/hexane to give N1-((R)-1-(4-chlorophenyl)ethyl)-6-methyl-N-5-(3-(9-(tetrahydro-2H-pyran-2-yl)-9H-purin-6-yl)pyridin-2-yl)isoquinoline-1,5-diamine as a syrup. MS Found: (ESI pos. ion) m/z 591 (M+H$^+$).

Step 4: N-5-(3-(9H-Purin-6-yl)pyridin-2-yl)-N-1-((R)-1-(4-chlorophenyl)ethyl)-6-methylisoquinoline-1,5-diamine To a 50 mL RBF was added N1-((R)-1-(4-chlorophenyl)ethyl)-6-methyl-N5-(3-(9-(tetrahydro-2H-pyran-2-yl)-9H-purin-6-yl)pyridin-2-yl)isoquinoline-1,5-diamine (0.060 g, 0.10 mmol), 2 M HCl (0.51 ml, 1.0 mmol) and dioxane (1 mL). The reaction mixture was heated at 100° C. in an oil bath for 3 h. The reaction mixture was concentrated, diluted with chloroform, washed with 10% sodium carbonate, dried over sodium sulfate and concentrated. The crude product was chromatographed on silica gel eluting with 80% ethyl acetate/hexane to give N-5-(3-(9H-purin-6-yl)pyridin-2-yl)-N1-((R)-1-(4-chlorophenyl)ethyl)-6-methylisoquinoline-1,5-diamine as a solid. MS Found: (ESI pos. ion) m/z 507 (M+H$^+$).

Table II includes additional representative compounds of Formulas I and II, including many of those exemplified above. Included in Table II is the method by which each Example was prepared, the MS data found, and Raf kinase biological date for each compound

TABLE II

| Ex. No. | Syn. Method | Compound Name (IUPAC) | Found MS (M + H)$^+$ | HTRF Enzyme assay Data IC$_{50}$ uM | B-Raf cell assay Data IC$_{50}$ uM |
|---|---|---|---|---|---|
| 69 | K | N-1-(4-chlorophenyl)-6-methyl-N-5-(5-(9H-purin-6-yl)-4-pyrimidinyl)-1,5-isoquinolinediamine | 480 | 0.002 | 0.004 |
| 70 | K | 4-((7-methyl-8-((3-(1H-pyrazolo[3,4-d]pyrimidin-4-yl)-2-pyridinyl)amino)-4-quinazolinyl)amino)benzonitrile | 471 | 0.005 | 0.086 |
| 71 | L | 4-((6-methyl-5-((3-(1H-pyrazolo[3,4-d]pyrimidin-4-yl)-2-pyridinyl)amino)-1-isoquinolinyl)amino)benzonitrile | 470 | 0.004 | 0.012 |
| 72 | L | N-1-(2,2-difluoro-1,3-benzodioxol-5-yl)-6-methyl-N-5-(3-(1H-pyrazolo[3,4-d]pyrimidin-4-yl)-2-pyridinyl)-1,5-isoquinolinediamine | 525 | 0.020 | 0.018 |
| 73 | M | 7-methyl-N-8-(3-(9H-purin-6-yl)-2-pyridinyl)-N-4-(3-(trifluoromethyl)phenyl)-4,8-quinazolinediamine | 514 | 0.026 | 0.033 |
| 74 | M | N-4-(2,2-difluoro-1,3-benzodioxol-5-yl)-7-methyl-N-8-(3-(9H-purin-6-yl)-2-pyridinyl)-4,8-quinazolinediamine | 526 | 0.008 | 0.004 |
| 75 | M | N-4-(3-ethynylphenyl)-7-methyl-N-8-(3-(9H-purin-6-yl)-2-pyridinyl)-4,8-quinazolinediamine | 470 | 0.003 | 0.028 |
| 76 | M | N-4-(4-(difluoromethoxy)phenyl)-7-methyl-N-8-(3-(9H-purin-6-yl)-2-pyridinyl)-4,8-quinazolinediamine | 512 | 0.009 | 0.005 |
| 77 | M | N-4-(4-chlorophenyl)-7-methyl-N-8-(3-(9H-purin-6-yl)-2-pyridinyl)-4,8-quinazolinediamine | 480 | 0.005 | 0.012 |
| 78 | M | N-1-((1R)-1-(4-chlorophenyl)ethyl)-6-methyl-N-5-(3-(9H-purin-6-yl)-2-pyridinyl)-1,5-isoquinolinediamine | 507 | 0.033 | 0.033 |

Various experimental methods have been employed to synthesize compounds of Formulas I and II, as more generally described in Schemes 1, 2a-d, 3, 3a-3d, 4 and 5a-5j above, and further described in more detail by the representative examples 30-39. Similarly, various experimental methods have been employed to synthesize compounds of Formulas I and II, such as those described in representative Examples 69 (Method K), 71 (Method L) and 73 (Method M), respectively.

The following compounds in Tables 3-8 are additional representative examples of Formulas I and H, as provided by the present invention.

TABLE 3

| Ex. No. | R² | R⁴ | X | L | R⁶ |
|---|---|---|---|---|---|
| 79 | 6-CH₃— | H | —NH— | —NH— | 3-CF₃-phenyl |
| 80 | 6-CH₃— | H | —NH— | —NH— | 3-dimethylamino-phenyl |
| 81 | 6-CH₃— | CH₃ | —NH— | —NH— | 3-CN-phenyl |
| 82 | 6-F— | CH₃ | —NH— | —C(O)NH— | 5-(3-t-butyl-1-methylpyrazole) |
| 83 | 6-Cl— | CH₃ | —NH— | —C(O)NH— | 6-(1-acetyl-6,6-dimethyl-2,3-dihydroindole |
| 84 | 4-Br— | CH3 | —N(CH3)— | —C(O)NH— | 3-isopropoxy-phenyl |
| 85 | 6-CH3— | H | —O— | —NH— | 1-(4-CF3-1-pyridine) |
| 86 | 5-CH3— | H | —O— | —NH— | 5-(2-methyl-1,3-benzothiazole) |
| 87 | 5-CH3— | H | —NH— | —NH— | 5-(2,3-dihydroindene) |
| 88 | 6-F— | H | —O— | —NH— | 3-trifluoro-methoxy-phenyl |
| 89 | 6-Cl— | H | —NH— | —NHC(O)— | 2-(3-dimethyl-aminopropyl)-methylamino-5-CF₃-phenyl |
| 90 | 4-Br— | H | —NH— | —NH— | 2-dimethylamino-5-CF₃-phenyl |
| 91 | 6-CH₃— | H | —N(CH₃)— | —S(O)₂NH— | 6-(1-acetyl-6,6-dimethyl-2,3-dihydroindole |
| 92 | 6-CH₃— | H | —O— | —NH— | 2-(3-dimethyl-aminopropyl)-methylamino-5-CF₃-phenyl |
| 93 | 6-CH₃— | H | —O— | —C(O)— | 3-isopropoxy-phenyl |

TABLE 4

| Ex. No. | R² | R⁴ | X | L | R⁶ |
|---|---|---|---|---|---|
| 94 | 6-CH₃— | H | —NH— | —NH— | 3-CF₃-phenyl |
| 95 | 6-CH₃— | H | —NH— | —NH— | 3-dimethylamino-phenyl |
| 96 | 6-CH₃— | CH₃ | —NH— | —NH— | 3-CN-phenyl |
| 97 | 6-F— | CH₃ | —NH— | —C(O)NH— | 5-(3-t-butyl-1-methylpyrazole) |
| 98 | 6-Cl— | CH₃ | —NH— | —C(O)NH— | 6-(1-acetyl-6,6-dimethyl-2,3-dihydroindole |
| 99 | 4-Br— | CH₃ | —N(CH₃)— | —C(O)NH— | 3-isopropoxy-phenyl |
| 100 | 6-CH₃— | H | —O— | —NH— | 1-(4-CF₃-1-pyridine) |
| 101 | 5-CH₃— | H | —O— | —NH— | 5-(2-methyl-1,3-benzothiazole) |
| 102 | 5-CH₃— | H | —NH— | —NH— | 5-(2,3-dihydroindene) |
| 103 | 6-F— | H | —O— | —NH— | 3-trifluoromethoxy-phenyl |
| 104 | 6-Cl— | H | —NH— | —NHC(O)— | 2-(3-dimethyl-aminopropyl)methyl-amino-5-CF₃-phenyl |
| 105 | 4-Br— | H | —NH— | —NH— | 2-dimethylamino-5-CF₃-phenyl |
| 106 | 6-CH₃— | H | —N(CH₃)— | —S(O)₂NH— | 6-(1-acetyl-6,6-dimethyl-2,3-dihydroindole |
| 107 | 6-CH₃— | H | —O— | —NH— | 2-(3-dimethyl-aminopropyl)methyl-amino-5-CF₃-phenyl |
| 108 | 6-CH₃— | H | —O— | —C(O)— | 3-isopropoxy-phenyl |

TABLE 5

| Ex. No. | R² | R⁴ | X | L | R⁶ |
|---|---|---|---|---|---|
| 109 | 6-CH₃— | H | —NH— | —NH— | 3-CF₃-phenyl |
| 110 | 6-CH₃— | H | —NH— | —NH— | 3-dimethylamino-phenyl |

TABLE 5-continued

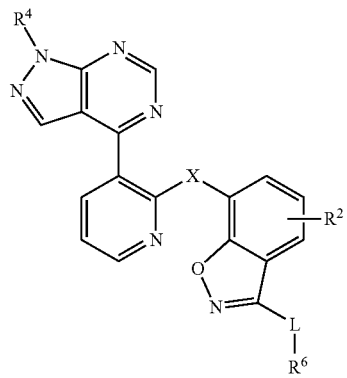

| Ex. No. | R² | R⁴ | X | L | R⁶ |
|---|---|---|---|---|---|
| 111 | 6-CH₃— | CH₃ | —NH— | —NH— | 3-CN-phenyl |
| 112 | 6-F— | CH₃ | —NH— | —C(O)NH— | 5-(3-t-butyl-1-methylpyrazole) |
| 113 | 6-Cl— | CH₃ | —NH— | —C(O)NH— | 6-(1-acetyl-6,6-dimethyl-2,3-dihydroindole |
| 114 | 4-Br— | CH₃ | —N(CH₃)— | —C(O)NH— | 3-isopropoxy-phenyl |
| 115 | 6-CH₃— | H | —O— | —NH— | 1-(4-CF₃-1-pyridine) |
| 116 | 5-CH₃— | H | —O— | —NH— | 5-(2-methyl-1,3-benzothiazole) |
| 117 | 5-CH₃— | H | —NH— | —NH— | 5-(2,3-dihydroindene) |
| 118 | 6-F— | H | —O— | —NH— | 3-trifluoro-methoxy-phenyl |
| 119 | 6-Cl— | H | —NH— | —NHC(O)— | 2-(3-dimethyl-aminopropyl)methylamino-5-CF₃-phenyl |
| 120 | 4-Br— | H | —NH— | —NH— | 2-dimethylamino-5-CF₃-phenyl |
| 121 | 6-CH₃— | H | —N(CH₃)— | —S(O)₂NH— | 6-(1-acetyl-6,6-dimethyl-2,3-dihydroindole |
| 122 | 6-CH₃— | H | —O— | —NH— | 2-(3-dimethyl-aminopropyl)methylamino-5-CF₃-phenyl |
| 123 | 6-CH₃— | H | —O— | —C(O)— | 3-isopropoxy-phenyl |

TABLE 6

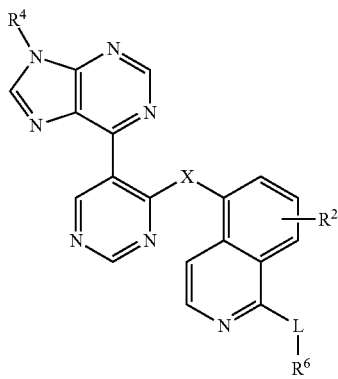

| Ex. No. | R² | R⁴ | X | L | R⁶ |
|---|---|---|---|---|---|
| 124 | 6-CH₃— | H | —NH— | —NH— | 3-CF₃-phenyl |
| 125 | 6-CH₃— | H | —NH— | —NH— | 3-dimethylamino-phenyl |
| 126 | 6-CH₃— | CH₃ | —NH— | —NH— | 3-CN-phenyl |
| 127 | 6-F— | CH₃ | —NH— | —C(O)NH— | 5-(3-t-butyl-1-methylpyrazole) |
| 128 | 6-Cl— | CH₃ | —NH— | —C(O)NH— | 6-(1-acetyl-6,6-dimethyl-2,3-dihydroindole |
| 129 | 4-Br— | CH₃ | —N(CH₃)— | —C(O)NH— | 3-isopropoxy-phenyl |
| 130 | 6-CH₃— | H | —O— | —NH— | 1-(4-CF₃-1-pyridine) |
| 131 | 5-CH₃— | H | —O— | —NH— | 5-(2-methyl-1,3-benzothiazole) |
| 132 | 5-CH₃— | H | —NH— | —NH— | 5-(2,3-dihydroindene) |
| 133 | 6-F— | H | —O— | —NH— | 3-trifluoromethoxy-phenyl |
| 134 | 6-Cl— | H | —NH— | —NHC(O)— | 2-(3-dimethyl-aminopropyl)methyl-amino-5-CF₃-phenyl |
| 135 | 4-Br— | H | —NH— | —NH— | 2-dimethylamino-5-CF₃-phenyl |
| 136 | 6-CH₃— | H | —N(CH₃)— | —S(O)₂NH— | 6-(1-acetyl-6,6-dimethyl-2,3-dihydroindole |
| 137 | 6-CH₃— | H | —O— | —NH— | 2-(3-dimethyl-aminopropyl)methyl-amino-5-CF₃-phenyl |
| 138 | 6-CH₃— | H | —O— | —C(O)— | 3-isopropoxy-phenyl |

TABLE 7

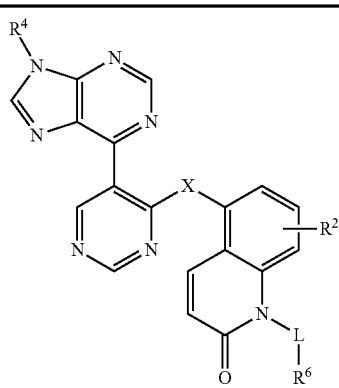

| Ex. No. | R² | R⁴ | X | L | R⁶ |
|---|---|---|---|---|---|
| 139 | 6-CH₃— | H | —NH— | —NH— | 3-CF₃-phenyl |
| 140 | 6-CH₃— | H | —NH— | —NH— | 3-dimethylamino-phenyl |
| 141 | 6-CH₃— | CH₃ | —NH— | —NH— | 3-CN-phenyl |

TABLE 7-continued

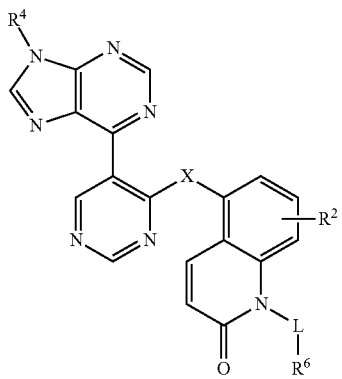

| Ex. No. | R² | R⁴ | X | L | R⁶ |
|---|---|---|---|---|---|
| 142 | 6-F— | CH₃ | —NH— | —C(O)NH— | 5-(3-t-butyl-1-methylpyrazole) |
| 143 | 6-Cl— | CH₃ | —NH— | —C(O)NH— | 6-(1-acetyl-6,6-dimethyl-2,3-dihydroindole |
| 144 | 4-Br— | CH₃ | —N(CH₃)— | —C(O)NH— | 3-isopropoxy-phenyl |
| 145 | 6-CH₃— | H | —O— | —NH— | 1-(4-CF₃-1-pyridine) |
| 146 | 5-CH₃— | H | —O— | —NH— | 5-(2-methyl-1,3-benzothiazole) |
| 147 | 5-CH₃— | H | —NH— | —NH— | 5-(2,3-dihydroindene) |
| 148 | 6-F— | H | —O— | —NH— | 3-trifluoromethoxy-phenyl |
| 149 | 6-Cl— | H | —NH— | —NHC(O)— | 2-(3-dimethyl-aminopropyl)methyl amino-5-CF₃-phenyl |
| 150 | 4-Br— | H | —NH— | —NH— | 2-dimethylamino-5-CF₃-phenyl |
| 151 | 6-CH₃— | H | —N(CH₃)— | —S(O)₂NH— | 6-(1-acetyl-6,6-dimethyl-2,3-dihydroindole |
| 152 | 6-CH₃— | H | —O— | —NH— | 2-(3-dimethyl-aminopropyl)methyl amino-5-CF₃-phenyl |
| 153 | 6-CH₃— | H | —O— | —C(O)— | 3-isopropoxy-phenyl |

TABLE 8

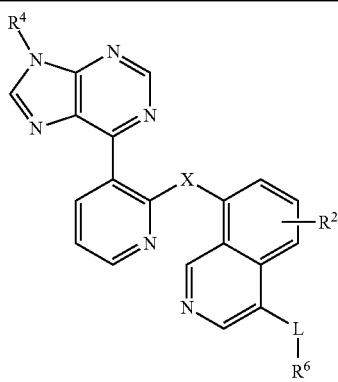

| Ex. No. | R² | R⁴ | X | L | R⁶ |
|---|---|---|---|---|---|
| 154 | 6-CH₃— | H | —NH— | —NH— | 3-CF₃-phenyl |
| 155 | 6-CH₃— | H | —NH— | —NH— | 3-dimethylamino-phenyl |
| 156 | 6-CH₃— | CH₃ | —NH— | —NH— | 3-CN-phenyl |
| 157 | 6-F— | CH₃ | —NH— | —C(O)NH— | 5-(3-t-butyl-1-methylpyrazole) |

TABLE 8-continued

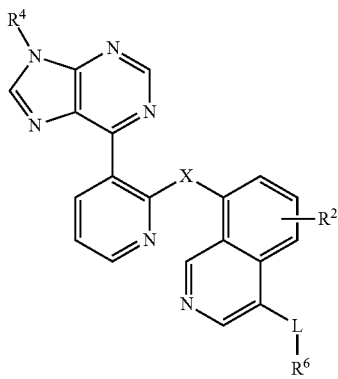

| Ex. No. | R² | R⁴ | X | L | R⁶ |
|---|---|---|---|---|---|
| 158 | 6-Cl— | CH₃ | —NH— | —C(O)NH— | 6-(1-acetyl-6,6-dimethyl-2,3-dihydroindole |
| 159 | 4-Br— | CH₃ | —N(CH₃)— | —C(O)NH— | 3-isopropoxy-phenyl |
| 160 | 6-CH₃— | H | —O— | —NH— | 1-(4-CF₃-1-pyridine) |
| 161 | 5-CH₃— | H | —O— | —NH— | 5-(2-methyl-1,3-benzothiazole) |
| 162 | 5-CH₃— | H | —NH— | —NH— | 5-(2,3-dihydroindene) |
| 163 | 6-F— | H | —O— | —NH— | 3-trifluoromethoxy-phenyl |
| 164 | 6-Cl— | H | —NH— | —NHC(O)— | 2-(3-dimethyl-aminopropyl)-methylamino-5-CF₃-phenyl |
| 165 | 4-Br— | H | —NH— | —NH— | 2-dimethylamino-5-CF₃-phenyl |
| 166 | 6-CH₃— | H | —N(CH₃)— | —S(O)₂NH— | 6-(1-acetyl-6,6-dimethyl-2,3-dihydroindole |
| 167 | 6-CH₃— | H | —O— | —NH— | 2-(3-dimethyl-aminopropyl)-methylamino-5-CF₃-phenyl |

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protecting groups may already be present in precursors and should protect the functional groups concerned against unwanted secondary reactions, such as acylations, etherifications, esterifications, oxidations, solvolysis, and similar reactions. It is a characteristic of protecting groups that they readily lend themselves, i.e. without undesired secondary reactions, to removal, typically accomplished by solvolysis, reduction, photolysis or other methods of removal such as by enzyme activity, under conditions analogous to physiological conditions. It should also be appreciated that the protecting groups should not be, present in the end-products. The specialist knows, or can easily establish, which protecting groups are suitable with the reactions described herein.

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen). For example, the $R^4$ substituent is drawn unattached to any specific atom of ring $Z^1$, and therefore each of the n number of $R^4$ substituent groups may be attached to any atom of $Z^1$.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I, II and II-A-II-C) vary with structural change, in general, activity possessed by compounds of Formulas I, II, II-A, and II-C may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit Raf kinase enzyme activity.

Biological Evaluation

The following assays can be employed to determine the degree of activity of individual compounds as Raf protein kinase inhibitors. Compounds described herein have been tested in one or more of these assays, and have shown activity. Representative compounds of the invention were tested and found to exhibit $IC_{50}$ values of at least <10 μM in any one of the described assays, thereby demonstrating and confirming the utility of the compounds of the invention as Raf kinase inhibitors and in the prophylaxis and treatment of Raf kinase mediated diseases, including, without limitation, cell-proliferative disorders and cancer.

B-raf-Homogenous Time Resolved Fluorescent (HTRF) Kinase Assay

A Homogeneous Time Resolved Fluorescence (HTRF) kinase assay was established to assay the ability of compounds to inhibit human mutant B-raf kinase activity on the substrate MEK1. The assay begins when 1 uL of a 50× compound dose curve in DMSO is added to 60 pM of recombinant HuBraf V600E in a final volume of 40 ul kinase reaction buffer. After a 60-minute incubation at room temperature, the kinase reaction is initiated with the addition of 10 ul substrate mix, resulting in a final concentration of 10 uM ATP (Km=~20 uM), 100 nM His-Avitag-MEK1 (Δ32-51, D190N kinase dead) (Km~200 nM) in a final reaction volume of 50 ul. The final concentration of the kinase reaction buffer is 50 mM Tris-HCL pH 7.5, 10 mM $MgCl_2$, 0.5% glucose, 0.5 mM DTT, 0.01% BSA. The kinase reaction proceeds for 60 minutes at room temperature until the reaction is quenched by the addition of 10 ul Stop/Detection buffer composed of kinase reaction buffer with the addition of Tween-20 (for a final concentration 0.1%), Hexokinase (0.01 unit), Streptavidin-Allophycocyanin (final 10 nM), and Europium labeled anti-Phospho-MEK1/2 (ser217/221 from Cell Signaling Technology) antibody (final 300 pM). The detection reaction proceeds for one hour and is read on a RubyStar (BMG Labtech) counter. IC50s for the test compounds are generated using Excel-XLfit software.

Of the exemplary compounds tested in the B-raf HTRF kinase assay, the data is provided in Tables I and II. Many of the exemplary compounds of the present invention have $IC_{50}$ activities for the inhibition of B-raf as measured by the HTRF assay of less than or equal to 1 uM. Many of these exemplary compounds of the present invention have $IC_{50}$ activities for the inhibition of B-raf as measured by the HTRF assay of less than or equal to 100 nM.

B-raf Cell-Based Assay

A cell-based assay was optimized to assay the ability of compounds to inhibit B-raf activity in a whole cell context. A375 cells, a human melanoma cell line having the V600E mutant B-raf is used in this assay. These cells exhibit constitutive B-raf kinase activity which signals through phospho-MEK1/2 resulting in high levels of phospho-ERK1/2 (MAPK). The cell-based assay quantifies the ratio of phospho-ERK1/2 to total ERK1/2 and can thereby assay the cellular inhibition of B-raf kinase activity. A375 cells are plated into 96 well plates and grown to confluence. The cells are then changed into starve media (DMEM/0.1% BSA) for 60 minutes. Compounds in DMSO dose curves are then diluted in starve media and added to cells. DMSO with no compound is used in one column to determine a 'High' (no inhibition) reading, and 10 uM of a potent Braf inhibitor (a control compound) is used in another column to determine a 'Low' (complete inhibition) reading. After a 60 minute incubation the cells are fixed for 20 minutes at RT in 4% formaldehyde with 0.1% Triton X-100, protease and phosphatase inhibitors in PBS. The cells are washed four times in PBS then blocked for 60 minutes using a one to one mix of Odyssey blocking buffer (Li-Cor Biosciences, Inc) and PBS. Primary antibodies (rabbit anti-phospho p42/p44 MAPK (P-ERK1/2) from Cell Signaling Technology and mouse anti-ERK2 from Santa Cruz Biotechnology) are diluted in blocking buffer, added to the cells and incubated overnight at 4° C. The cells are then washed four times in PBS/0.1% Tween-20. Secondary antibodies (anti-mouse IRDye 800CW from Rockland, Inc and anti-rabbit AlexaFlour680 from Molecular Probes) are diluted in blocking buffer/0.5% Tween and incubated on cells for 60 minutes. After 4 washes in PBS/0.1% Tween-20 the microplate is scanned on an Odyssey Infrared Imager (Li-Cor Bioscience) which can read the signal given by the two secondary antibodies on their respective channels. The ratio of P-ERK/total ERK is determined and IC50s generated using Excel-XLfit software.

Of the exemplary compounds tested in the B-raf cell based assay, the data is provided in Tables I and H. Many of the exemplary compounds of the present invention have $IC_{50}$ activities for the inhibition of B-raf as measured by the cell based assay of less than or equal to 1 uM. Many of these exemplary compounds of the present invention have $IC_{50}$ activities for the inhibition of B-raf as measured by the cell based assay of less than or equal to 100 nM.

Indications

Accordingly, compounds of the invention are useful for, but not limited to, the prevention or treatment of Raf kinase-mediated diseases and disorders including, cancer and the RAS-RAF-MEK-ERK cell signaling pathway related diseases. In one embodiment of the invention, there is provided a method of modulating a Raf kinase enzyme in a subject, the method comprising administering to the subject an effective dosage amount of a compound of any of Formulas I, II, II-A, II-B and II-C. In another embodiment, the Raf kinase is a mutant version of the naturally occurring Raf protein, such as the V600E mutant protein.

Raf-mediated disorders involve various cancers. In one embodiment, the invention provides a method of treating a Raf kinase-mediated condition selected from the group consisting of melanoma, solid tumor, ovarian cancer, pancreatic cancer, lung cancer, colon cancer and thyroid cancer. In another embodiment, the invention provides a method of treating a solid carcinoma of the lung, pancreas, thyroid, bladder or colon in a subject, the method comprising administering to the subject an effective dosage amount of a compound according to any of Formulas I, II, II-A, II-B and II-C.

Treatment of Raf-kinase mediated disease may be accomplished in combination with other oncological therapies. In one embodiment, the invention provides a method wherein administering the effective amount of the compound of Formula I, II, II-A, II-B and II-C to the subject comprises administering the compound in combination with one or more compounds selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof.

Cancers which may be treated with compounds of the invention include, without limitation, carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

Other therapeutic agents such as those described below may be employed with the inventive compounds in the present methods. In the methods of the present invention, such other therapeutic agent(s) may be administered prior to, simultaneously with or following the administration of the compound(s) of the present invention.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition or medicament comprising the compound, to a subject (i.e., an animal, preferably a mammal, most preferably a human) which may be in need of preventative treatment, such as, for example, for pain, inflammation, cancer and the like. Treatment also encompasses prophylactic administration of a compound of the invention, or a pharmaceutical salt thereof, or a pharmaceutical composition or medicament of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. In yet another embodiment, there I provided a method of manufacturing a medicament having therein a compound of Formulas I, II, II-A, II-B or II-C, comprising combining the compound with a pharmaceutically acceptable excipient. The pharmaceutical composition, or medicament (used herein synonymously with composition) of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer such as with radiation therapy or with cytostatic or cytotoxic agents.

If formulated as a fixed dose, such combination products employ the compounds of this invention within the accepted dosage ranges. Compounds of Formulas I-II may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

Currently, standard treatment of primary tumors consists of surgical excision followed by either radiation or intravenous (IV) administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula II:

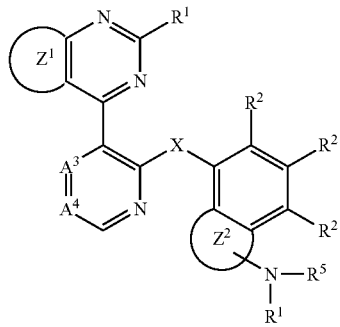

or a pharmaceutically acceptable salt thereof, wherein
each of $A^3$ and $A^4$, independently, is CH;
X is $CR^2R^2$, C(O), $NR^2$, O or $S(O)_p$ wherein p is 0, 1, or 2;
$Z^1$ is

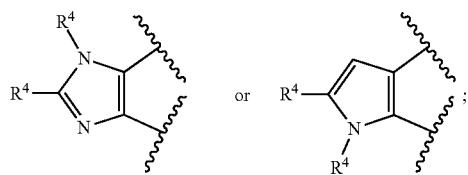

$Z^2$ is

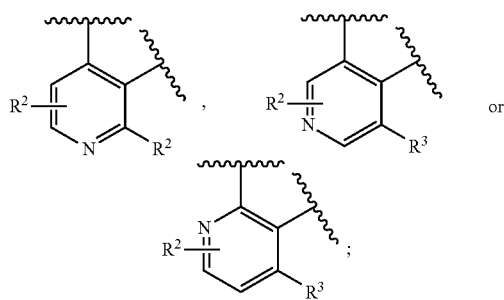

$R^1$ is H;
each $R^2$ independently, is H, halo, haloalkyl, $NO_2$, CN or $C_{1-6}$-alkyl;
$R^3$ is $NR^5R^5$, $NR^5R^6$, $OR^5$, $SR^5$, $OR^6$, $SR^6$, $C(O)R^5$, $C(S)R^5$, $C(NCN)R^5$, $C(O)R^6$, $C(S)R^6$, $C(NCN)R^6$, $OC(O)R^5$, $COOR^5$, $C(O)NR^5R^5$, $C(O)NR^5R^6$, $NR^5C(O)R^5$, $NR^5C(O)R^6$, $NR^5C(O)NR^5R^5$, $NR^5C(O)NR^5R^6$, $NR^5(COOR^5)$, $NR^5(COOR^6)$, $S(O)_2R^5$, $S(O)_2R^6$, $S(O)_2NR^5R^5$, $S(O)_2NR^5R^6$, $NR^5S(O)_2NR^5R^6$, $NR^5S(O)_2R^5$ or $NR^5S(O)_2R^6$;
each $R^4$, independently, is H, halo, haloalkyl or $C_{1-8}$-alkyl, wherein said $C_{1-8}$-alkyl is optionally substituted independently with 1-5 substituents of $R^7$;
each $R^5$ independently, is H, $C_{1-8}$-alkyl, $C_{2-8}$-alkenyl, $C_{2-8}$-alkynyl, $C_{3-6}$-cycloalkyl or $C_{4-8}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^6$ or $R^7$, $NR^6R^7$, $NR^7R^7$, $OR^6$, $SR^6$, $OR^7$, $SR^7$, $C(O)R^7$, $OC(O)R^6$, $COOR^6$, $C(O)R^7$, $OC(O)R^7$, $COOR^7$, $C(O)NR^6R^7$, $NR^7C(O)R^6$, $C(O)NR^7R^7$, $NR^7C(O)R^7$, $NR^7C(O)NR^6R^7$, $NR^7C(O)NR^7R^7$, $NR^7(COOR^6)$, $NR^7(COOR^7)$, $OC(O)NR^6R^7$, $OC(O)NR^7R^7$, $S(O)_2R^6$, $S(O)_2R^7$, $S(O)_2NR^6R^7$, $S(O)_2NR^7R^7$, $NR^7S(O)_2NR^6R^7$, $NR^7S(O)_2NR^7R^7$, $NR^7S(O)_2R^6$, $NR^7S(O)_2R^7$, $NR^7S(O)_2R^6$ or $NR^7S(O)_2R^7$;
$R^6$ is a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is optionally substituted independently with 1-5 substituents of $R^7$;
alternatively, $R^5$ and $R^6$ taken together form a partially or fully saturated or unsaturated 5-6 membered ring of carbon atoms optionally including 1-3 heteroatoms selected from O, N, or S, and the ring optionally substituted independently with 1-5 substituents of $R^7$; and
each $R^7$, independently, is H, F, Cl, Br, I, haloalkyl, CN, OH, $NO_2$, $NH_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

2. The compound of claim 1, or a pharmaceutically acceptable salt thereof, wherein $Z^2$ is

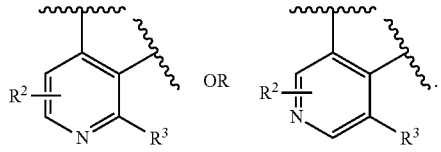

3. The compound of claim 1, or a pharmaceutically acceptable salt thereof, wherein X is $CH_2$, NH, O or S.

4. The compound of claim 1, or a pharmaceutically acceptable salt thereof, wherein $R^3$ is $NR^5R^5$, $NR^5R^6$, $NR^5C(O)R^5$, $NR^5C(O)R^6$, $NR^5S(O)_2R^5$ or $NR^5S(O)_2R^6$;
$R^5$ is H, $C_{1-6}$-alkyl or $C_{3-6}$-cycloalkyl optionally substituted with 1-3 substituents of $R^7$; and
$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoxazolyl, benzothiazolyl, benzoxadiazolyl, indolyl, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$.

5. The compound of claim 1 having a Formula II

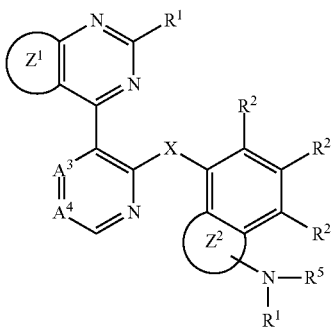

or a pharmaceutically acceptable salt thereof, wherein
each of $A^3$ and $A^4$, independently, is CH;
$X$ is $CHR^2$, NH or O;
$Z^1$ is a ring selected from

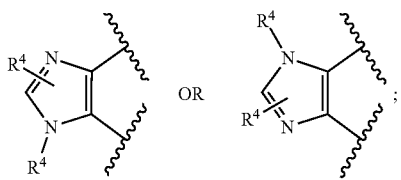

$Z^2$ is a ring selected from

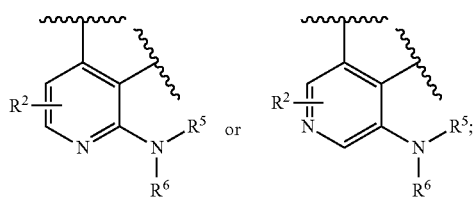

$R^1$ is H;
each $R^2$ independently, is H, halo, haloalkyl or $C_{1-6}$-alkyl;
each $R^4$, independently, is H, halo, haloalkyl or $C_{1-6}$-alkyl;
$R^5$ is H, $C_{1-6}$-alkyl or $C_{3-6}$-cycloalkyl optionally substituted with 1-3 substituents of $R^7$;
$R^6$ is phenyl, naphthyl, pyridyl, pyrimidinyl, triazinyl, pyridazinyl, thiophenyl, furyl, tetrahydrofuryl, pyrrolyl, pyrazolyl, quinolinyl, isoquinolinyl, quinazolinyl, isoquinazolinyl, phthalazinyl, thieno-pyrazolyl, imidazolyl, triazolyl, thiazolyl, thiadiazolyl, oxazolyl, oxadiazolyl, isoxazolyl, isothiazolyl, benzoisothiazolyl, benzoxazolyl, benzothiazolyl, benzoxadiazolyl, benzodioxolyl, benzodioxinyl, indolyl, 1,3-dihydroindol-2-one, quinolinone, azaindolyl, isoindolyl, indazolyl, benzofuranyl, benzothiophenyl, benzimidazolyl, pyrrolidinyl, pyrazolinyl, morpholinyl, piperidinyl or piperazinyl, each of which is optionally substituted independently with 1-5 substituents of $R^7$; and
each $R^7$, independently, is H, F, Cl, Br, I, haloalkyl, CN, OH, $NO_2$, $NH_2$, $C_{1-8}$-alkyl, —O—$C_{1-8}$-alkyl, —$C_{1-6}$-alkyl-O—$C_{1-6}$-alkyl, —S—$C_{1-8}$-alkyl, —$C_{1-6}$-alkyl-S—$C_{1-6}$-alkyl, —NH—$C_{1-8}$-alkyl, —N-di-$C_{1-8}$-alkyl, —$C_{1-6}$-alkyl-NH—$C_{1-6}$-alkyl, $C_{2-8}$-alkenyl, $C_{2-8}$-alkynyl, $C_{3-6}$-cycloalkyl, oxo, acetyl, benzyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of said $C_{1-8}$-alkyl, $C_{1-8}$-alkenyl, $C_{1-8}$-alkynyl and ring of said ring system is optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

6. The compound of claim 5, or a pharmaceutically acceptable salt thereof, wherein at least one of the three $R^2$ substitutions is other than H.

7. The compound of claim 1, or a pharmaceutically acceptable salt thereof, selected from
4-((6-methyl-5-((3-(9H-purin-6-yl)-2-pyridinyl)amino)-1-isoquinolinyl)amino)benzonitrile;
6-methyl-N-5-(3-(9H-purin-6-yl)-2-pyridinyl)-N-1-(3-(trifluoromethyl)phenyl)-1,5-isoquinolinediamine;
N-1-(2,2-difluoro-1,3-benzodioxol-5-yl)-6-methyl-N-5-(3-(9H-purin-6-yl)-2-pyridinyl)-1,5-isoquinolinediamine;
N-(4-chlorophenyl)-6-methyl-5-((3-(9H-purin-6-yl)-2-pyridinyl)oxy)-1-isoquinolinamine;
4-(5-(3-(9-(4-methoxybenzyl)-9H-purin-6-yl)pyridin-2-ylamino)-6-methylisoquinolin-1-ylamino)benzonitrile;
4-(5-(3-(9H-purin-6-yl)pyridin-2-ylamino)-6-methylisoquinolin-1-ylamino)benzonitrile;
5-(3-(9H-purin-6-yl)pyridin-2-yloxy)-N-(4-chlorophenyl)-6-methylisoquinolin-1-amine;
N-1-(4-chlorophenyl)-6-methyl-N-5-(3-(9H-purin-6-yl)-2-pyridinyl)-1,5-isoquinolinediamine;
4-((6-methyl-5-((3-(9H-purin-6-yl)-2-pyridinyl)amino)-1-isoquinolinyl)amino)benzonitrile;
N-1-(2,2-difluoro-1,3-benzodioxol-5-yl)-6-methyl-N-5-(3-(9H-purin-6-yl)-2-pyridinyl)-1,5-isoquinolinediamine;
N-(4-chlorophenyl)-6-methyl-5-((3-(9H-purin-6-yl)-2-pyridinyl)oxy)-1-isoquinolinamine;
N-5-(3-(9H-purin-6-yl)pyridin-2-yl)-N-1-((R)-1-(4-chlorophenyl)ethyl)-6-methylisoquinoline-1,5-diamine;
N-1-(4-chlorophenyl)-6-methyl-N-5-(5-(9H-purin-6-yl)-4-pyrimidinyl)-1,5-isoquinolinediamine; and
N-1-((1R)-1-(4-chlorophenyl)ethyl)-6-methyl-N-5-(3-(9H-purin-6-yl)-2-pyridinyl)-1,5-isoquinolinediamine.

8. The compound of claim 7, or a pharmaceutically acceptable salt thereof, selected from
4-((6-methyl-5-((3-(9H-purin-6-yl)-2-pyridinyl)amino)-1-isoquinolinyl)amino)benzonitrile;
6-methyl-N-5-(3-(9H-purin-6-yl)-2-pyridinyl)-N-1-(3-(trifluoromethyl)phenyl)-1,5-isoquinolinediamine;
N-(4-chlorophenyl)-6-methyl-5-((3-(9H-purin-6-yl)-2-pyridinyl)oxy)-1-isoquinolinamine;
5-(3-(9H-purin-6-yl)pyridin-2-yloxy)-N-(4-chlorophenyl)-6-methylisoquinolin-1-amine;
N-1-(4-chlorophenyl)-6-methyl-N-5-(3-(9H-purin-6-yl)-2-pyridinyl)-1,5-isoquinolinediamine;
N-1-(2,2-difluoro-1,3-benzodioxol-5-yl)-6-methyl-N-5-(3-(9H-purin-6-yl)-2-pyridinyl)-1,5-isoquinolinediamine;
N-5-(3-(9H-purin-6-yl)pyridin-2-yl)-N-1-((R)-1-(4-chlorophenyl)ethyl)-6-methylisoquinoline-1,5-diamine; and
N-1-((1R)-1-(4-chlorophenyl)ethyl)-6-methyl-N-5-(3-(9H-purin-6-yl)-2-pyridinyl)-1,5-isoquinolinediamine.

9. A pharmaceutical composition comprising a pharmaceutically acceptable excipient and a compound according to claim 8.

10. The compound of claim 8, or a pharmaceutically acceptable salt thereof, selected from
- 4-((6-methyl-5-((3-(9H-purin-6-yl)-2-pyridinyl)amino)-1-isoquinolinyl)amino)benzonitrile;
- 6-methyl-N-5-(3-(9H-purin-6-yl)-2-pyridinyl)-N-1-(3-(trifluoromethyl)phenyl)-1,5-isoquinolinediamine;
- N-(4-chlorophenyl)-6-methyl-5-((3-(9H-purin-6-yl)-2-pyridinyl)oxy)-1-isoquinolinamine;
- N-1-(4-chlorophenyl)-6-methyl-N-5-(3-(9H-purin-6-yl)-2-pyridinyl)-1,5-isoquinolinediamine; and
- N-1-((1R)-1-(4-chlorophenyl)ethyl)-6-methyl-N-5-(3-(9H-purin-6-yl)-2-pyridinyl)-1,5-isoquinolinediamine.

11. A pharmaceutical composition comprising a pharmaceutically acceptable excipient and a compound according to claim 10.

12. A pharmaceutical composition comprising a pharmaceutically acceptable excipient and a compound according to claim 1.

13. A process for synthesizing a compound of claim 1, the process comprising the step of reacting a compound of Formula A

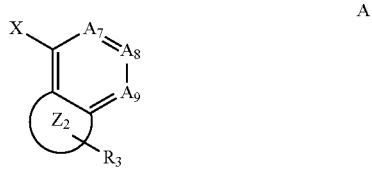

A wherein X is a nucleophilic species selected from an amine, an alcohol, a thiol and a carbanionic nucleophile, and wherein $A^{7-9}$, $Z^2$ and $R^3$ are as defined in claim 1, with a compound of Formula B

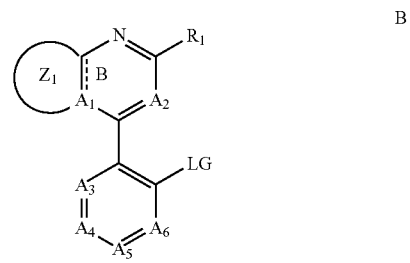

B wherein LG is a leaving group selected from a halogen, a metallic species, a boronic acid and a Grignard reagent, and wherein $A^{1-6}$, bond B, $Z^1$ and $R^1$ are as defined in claim 1, to synthesize the compound of claim 1.

* * * * *